United States Patent
Malley et al.

(10) Patent No.: US 10,766,932 B2
(45) Date of Patent: *Sep. 8, 2020

(54) MULTIPLE ANTIGEN PRESENTING IMMUNOGENIC COMPOSITION, AND METHODS AND USES THEREOF

(75) Inventors: Richard Malley, Beverly, MA (US); Yingjie Lu, West Roxbury, MA (US); Fan Zhang, West Roxbury, MA (US)

(73) Assignee: THE CHILDREN'S MEDICAL CENTER CORPORATION, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/116,402

(22) PCT Filed: May 11, 2012

(86) PCT No.: PCT/US2012/037412
§ 371 (c)(1),
(2), (4) Date: Jan. 29, 2014

(87) PCT Pub. No.: WO2012/155007
PCT Pub. Date: Nov. 15, 2012

(65) Prior Publication Data
US 2014/0154287 A1    Jun. 5, 2014

Related U.S. Application Data

(60) Provisional application No. 61/484,934, filed on May 11, 2011, provisional application No. 61/608,168, filed on Mar. 8, 2012, provisional application No. 61/609,974, filed on Mar. 13, 2012.

(51) Int. Cl.
| | |
|---|---|
| *C07K 14/31* | (2006.01) |
| *A61K 47/61* | (2017.01) |
| *A61K 47/54* | (2017.01) |
| *A61P 31/04* | (2006.01) |
| *A61K 39/09* | (2006.01) |
| *A61K 39/385* | (2006.01) |
| *A61K 39/00* | (2006.01) |

(52) U.S. Cl.
CPC ............ *C07K 14/31* (2013.01); *A61K 39/092* (2013.01); *A61K 39/385* (2013.01); *A61K 47/543* (2017.08); *A61K 47/557* (2017.08); *A61K 47/61* (2017.08); *A61P 31/04* (2018.01); *A61K 2039/55505* (2013.01); *A61K 2039/6031* (2013.01); *A61K 2039/6093* (2013.01); *A61K 2039/625* (2013.01); *A61K 2039/627* (2013.01); *A61K 2039/645* (2013.01); *A61K 2039/70* (2013.01); *C07K 2319/00* (2013.01); *C07K 2319/20* (2013.01); *Y02A 50/484* (2018.01)

(58) Field of Classification Search
None
See application file for complete search history.

(56) References Cited

U.S. PATENT DOCUMENTS

| | | |
|---|---|---|
| 6,287,568 B1 | 9/2001 | Wang et al. |
| 9,499,593 B2 | 11/2016 | Malley et al. |
| 10,017,548 B2 | 7/2018 | Malley et al. |
| 2006/0251675 A1* | 11/2006 | Hagen ............... A61K 39/39 424/203.1 |
| 2007/0128183 A1* | 6/2007 | Meinke ............... C07K 14/205 424/130.1 |
| 2008/0032340 A1 | 2/2008 | Ghosh et al. |
| 2008/0112964 A1* | 5/2008 | Kirkham ............ C07K 16/1275 424/185.1 |
| 2009/0054251 A1* | 2/2009 | O'Connor ............ A61K 35/16 506/9 |
| 2009/0148894 A1 | 6/2009 | Broedel |
| 2009/0148897 A1 | 6/2009 | Dai |
| 2010/0003266 A1 | 1/2010 | Simon |
| 2010/0020945 A1 | 1/2010 | Li et al. |
| 2010/0022401 A1 | 1/2010 | Nordlund et al. |
| 2010/0166802 A1 | 7/2010 | Caplan et al. |
| 2010/0209450 A1 | 8/2010 | Biemans et al. |
| 2013/0115230 A1* | 5/2013 | Simon ...................... 424/178.1 |
| 2014/0154286 A1 | 6/2014 | Malley et al. |
| 2014/0154287 A1 | 6/2014 | Malley et al. |

(Continued)

FOREIGN PATENT DOCUMENTS

| | | |
|---|---|---|
| EP | 1838345 | 10/2007 |
| JP | H11-502820 A | 3/1999 |

(Continued)

OTHER PUBLICATIONS

Sanabria-Valentin. Dissertation. Department of Basic Medical Sciences, New York University, 2008 at p. 8-9 describing the general structure of LPS.*
Grun et al. Analytical Biochemistry 354 (2006) 54-63.*
Elgert, Klaus D., Immunology Understanding the Immune System. John Wiley & Sons, Inc. Hoboken, New Jersey. 2009, p. 111.*
Hsu et al. The Journal of Biological Chemistry 284:34479-34489 Dec. 11, 2009.*
I. M. Rosenberg, Protein Analysis and Purification. Springer Science+Business Media New York, pp. 153-182, 1996.*
Hermanson, Greg T.. Bioconjugate Techniques, Elsevier Science, 1996. ProQuest Ebook Central, http://ebookcentral.proquest.com/lib.uspto-ebooks/detail.action?docID=307203. Created from uspto-ebooks on Sep. 6, 2017, pp. 570-592.*

(Continued)

*Primary Examiner* — Oluwatosin A Ogunbiyi
(74) *Attorney, Agent, or Firm* — Nixon Peabody, LLP; David S. Resnick

(57) ABSTRACT

The present embodiments provide for an immunogenic multiple antigen presenting system comprising a polymer to which antigens are associated by complementary affinity molecules. For example, the polymer can be a polysaccharide, or antigenic polysaccharide, to which protein or peptide antigens from the same or different pathogens are indirectly linked. The present immunogenic compositions can elicit both humoral and cellular immune responses to one or multiple antigens at the same time.

42 Claims, 21 Drawing Sheets

Specification includes a Sequence Listing.

(56) References Cited

U.S. PATENT DOCUMENTS

| | | | |
|---|---|---|---|
| 2015/0374811 A1 | 12/2015 | Malley et al. | |
| 2016/0090404 A1 | 3/2016 | Malley et al. | |
| 2019/0119335 A1 | 4/2019 | Malley et al. | |

FOREIGN PATENT DOCUMENTS

| | | |
|---|---|---|
| JP | 2007-504237 A | 3/2007 |
| JP | 2014-517835 A | 7/2014 |
| RU | 2164943 C2 | 4/2001 |
| RU | 2378008 C2 | 3/2006 |
| RU | 2006117425 A | 12/2007 |
| RU | 2407749 | 12/2010 |
| WO | 1996/029094 | 9/1996 |
| WO | 98/47530 A2 | 10/1998 |
| WO | 2003/094960 | 11/2003 |
| WO | 2005/037190 A2 | 4/2005 |
| WO | 2005/039501 A2 | 5/2005 |
| WO | 2006/017929 A1 | 2/2006 |
| WO | 2006/067632 | 6/2006 |
| WO | 2007026249 A1 | 3/2007 |
| WO | 2007/081583 | 7/2007 |
| WO | 2007/150020 A1 | 12/2007 |
| WO | 2008/094986 A2 | 8/2008 |
| WO | 2008/152448 A2 | 12/2008 |
| WO | 2009/021548 A1 | 2/2009 |
| WO | 2009/029831 | 3/2009 |
| WO | 2010/053559 | 5/2010 |
| WO | 2010/071986 A1 | 7/2010 |
| WO | 2011/008548 A1 | 1/2011 |
| WO | 2012/155007 A1 | 11/2012 |
| WO | 2012/155053 A1 | 11/2012 |

OTHER PUBLICATIONS

Sano et al. In Methods in Enzymology, vol. 326, pp. 305-307.*

Zhang et al., "Multiple antigen-presenting system (MAPS) to induce comprehensive B- and T-cell immunity" Proceedings of the National Academy of Sciences 110(33):13564-13569 (2013).

EP Communication dated Apr. 9, 2015 in corresponding EP Application No. 12781636.1.

Cortajarena et al., "A receptor-binding region in *Escherichia coli* alpha-haemolysin." J Biol Chem, 278(21):19159-19163 (2003).

Database, UniProt KB/TrEMBL, B3Q265_RHIE6, Sep. 2, 2008.

Database, UnitProt KB/TrEMBL, F2AA21_RHIET, May 31, 2011.

Database, UniProt KB/TrEMBL, Q8KKW2_RHIEC, Oct. 1, 2002.

Helppolainen et al., "Bradavidin II from Bradyrhizobium japoconium: A new avidin-like biotin-binding protein", Biochimica et Biphysica Acta 1784(7-8):1002-1010 (2008).

Hytonen et al., "Efficient production of active chicken avidin using a bacterial signal peptide in *Escherichia*", Biochem. J. 385-390 (2004).

Izard et al., "Signal peptides: exquisitely designed transport promoters", Molecular Microbiology 13(5):765-773 (1994).

Takakura et al., "Tamavidin, a versatile affinity tag for protein purification and immobilization", J Biotechnol. 145(4):317-322 (2010).

Wardenburg et al., "Vaccine protection against *Staphylococcus aureus* pneumonia", JEM 205(2):287-294 (2008).

Insel et al., "Response to Oligosaccharide-Protein Conjugate Vaccine against Hemophilus influenzae b in Two Patients with IgG2 Deficiency Unresponsive to Capsular Polysaccharide Vaccine", N Engl J Med 315:499-503, 1986.

Jin et al., "Conjugates of group A and W135 capsular polysaccharides of neisseria meningitidis bound to recombinant *Staphylococcus aureus* enterotoxin C1: preparation, physicochemical characterization, and immunological properties in mice", Infect Immun 73(12):7887-7893, 2005.

Sen et al., "In vivo humoral immune responses to isolated pneumococcal polysaccharides are dependent on the presence of associated TLR ligands", J Immunol 175(5): 3084-3091, 2005.

Scott et al., "Immunogenicity of biotinylated hapten-avidin complexes", Mol Immunol 21(11):1055-1060, 1984.

Thermo Scientific Avidin-Biotin Technical Handbook 16-17 (2009). Web. https://www.thermofisher.com/content/dam/LifeTech/Images/integration/1601675_AvBi_HB_INTL.pdf.

International Search Report for PCT/US2012/037412 (Multiple Antigen Presenting Immunogenic Composition, and Methods and Uses Thereof, filed May 11, 2012), issued by ISA/FIPS, 3 pages (dated Aug. 23, 2012).

International Search Report for PCT/US2012/037541 (Modified Biotin-Binding Protein, Fusion Proteins Thereof and Applications, filed May 11, 2012), issued by ISA/FIPS, 4 pages (dated Aug. 30, 2012).

Written Opinion for PCT/US2012/037412 (Multiple Antigen Presenting Immunogenic Composition, and Methods and Uses Thereof, filed May 11, 2012), issued by ISA/FIPS, 4 pages (dated Aug. 23, 2012).

Written Opinion for PCT/US2012/037541 (Modified Biotin-Binding Protein, Fusion Proteins Thereof and Applications, filed May 11, 2012), issued by ISA/FIPS, 3 pages (dated Aug. 30, 2012).

Avci et al., "A mechanism for glycoconjugate vaccine activation of the adaptive immune system and its implications for vaccine design", Nature Medicine 17(12) 1602-1609 (Dec. 2001) doi:10.1038/nm.2535.

Colono et al., "Noncovalent Association of Protein and Capsular Polysaccharide on Bacteria-Sized Latex Beads as a Model for Polysaccharide-Specific Humoral Immunity to Intact Gram-Positive Extracellular Bacteria", J. of Immun. at:https://www.jimmunol.org/cji/doi/10.4049/jimmunol.1300722.

Fauvart, M. et al, Genome Sequence of Rhizobium etli CNPAF512, a Nitrogen-Fixing Symbiont Isolated from Bean Root Nodules in Brazil, Journal of Bacteriology, 193(12): 3158-3159 (2011).

González, V. et al, The mosaic structure of the symbiotic plasmid of Rhizobium etli CFN42 and its relation to other symbiotic genome compartments, Genome Biol., 4(6): R36 (2003).

Colino, J. et al, Parameters Underlying Distinct T Cell-Dependent Polysaccharide-Specific IgG Responses to an Intact Gram-Positive Bacterium versus a Soluble Conjugate Vaccine, Journal of Immunology, 183: 1551-1559 (2009).

Dagan et al., Vaccine, 28(34):5513-5523 (2010) "Glycoconjugate vaccines and immune interference: A review".

Gaj et al., 56 Prot Express Purif, 54-61 (2007) "The AviD-tag, a NeutrAvidin/avidin specific peptide affinity tag for the immobilization and purification of recombinant proteins".

Helppolainen et al., Biochemical Journal, 405:397-405 (2007) "Rhizavidin from Rhizobium etli: the first natural dimer in the avidin protein family".

Huang et al., mBio, 1(3):e00164-10 (2010) "Robust stimulation of humoral and cellular immune responses following vaccination with antigen-loaded beta-glucan particles".

Lees et al., Vaccine, 12(13):1160-1166 (1994) "Enhanced immunogenicity of protein-dextran conjugates. 1. Rapid stimulation of enhanced antibody-responses to poorly immunogenic molecules."

Pollabauer et al., Vaccine, 27(11):1674-1679 (2009) "The influence of carrier protein on the immunogenicity of simultaneously administered conjugate vaccines in infants".

* cited by examiner

MKKIWLALAGLVLAFSASA AQDP Rhavi (45-179) GGGGSSSVDKLAAALEHHHHHH
MKKIWLALAGLVLAFSASA AQDP Rhavi (45-179) GGGGSSS Antigen X LEHHHHHH
Figure 3A
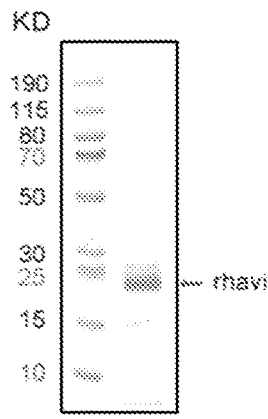
Figure 3B
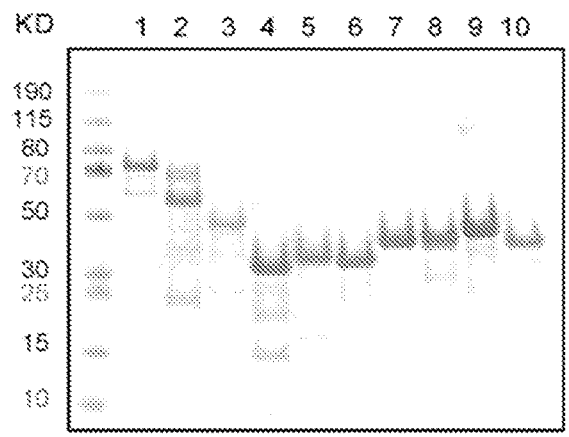
Figure 3C
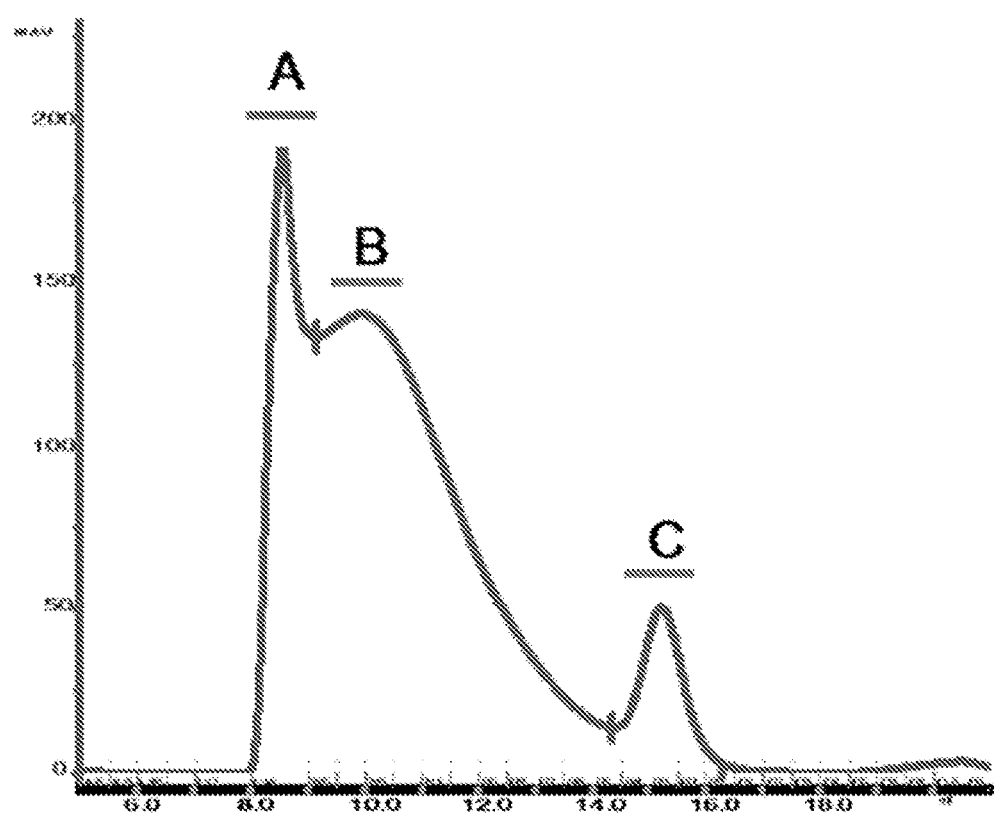
Figure 4A Figure 13A                              Figure 13B

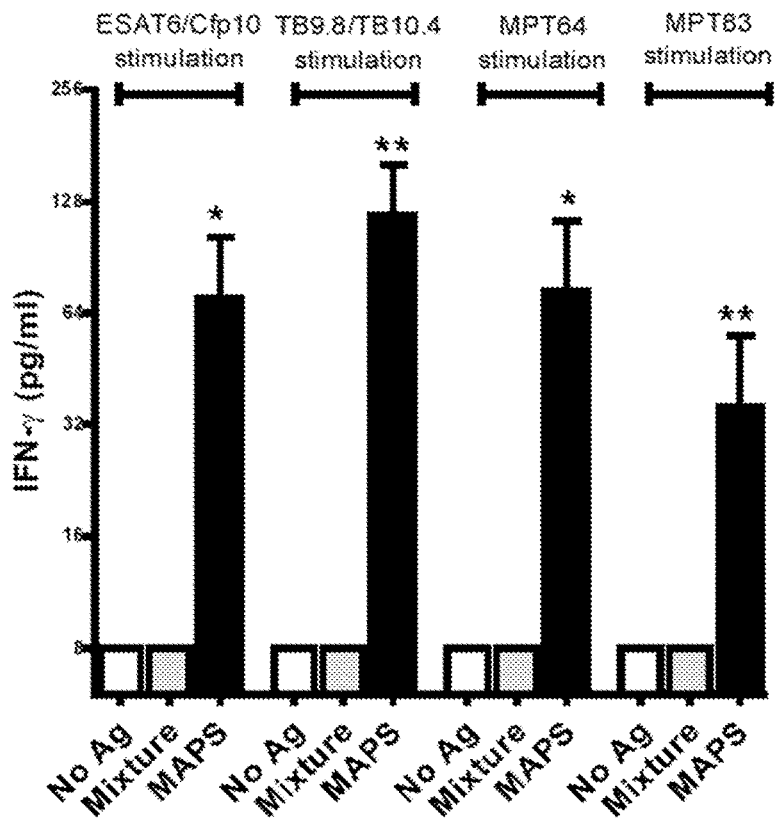
Figure 15F
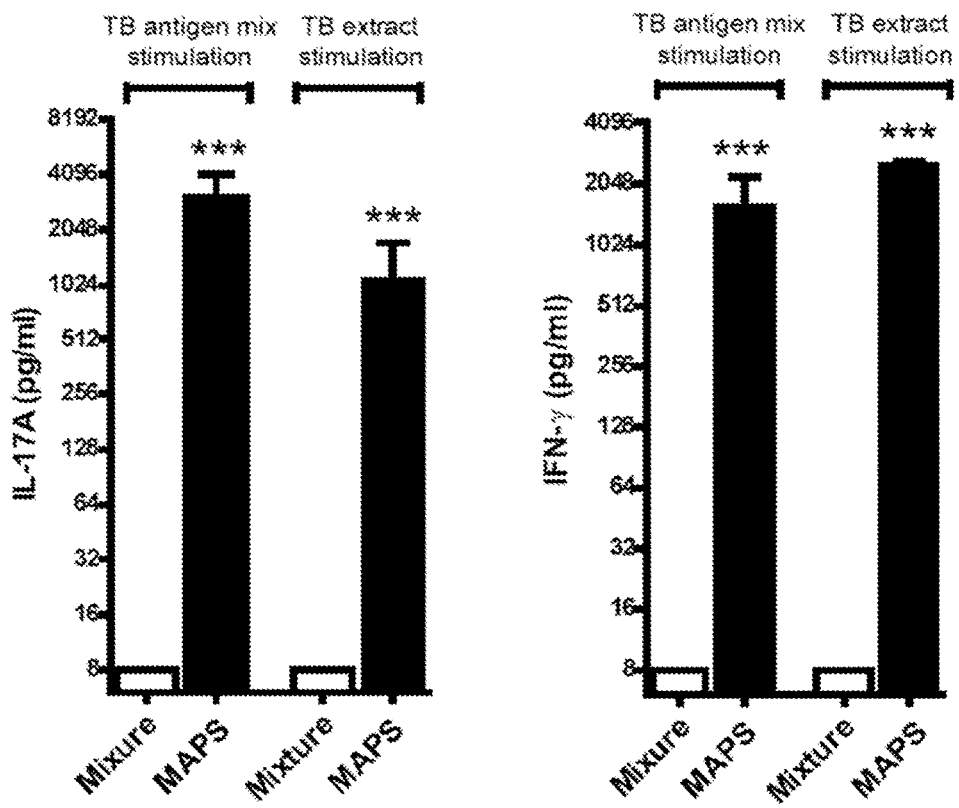
Figure 15G
Figure 15H

MULTIPLE ANTIGEN PRESENTING IMMUNOGENIC COMPOSITION, AND METHODS AND USES THEREOF

CROSS REFERENCE TO RELATED APPLICATIONS

The present application is a 35 U.S.C. § 371 National Phase Entry Application of International Application No. PCT/US2012/037412 filed May 11, 2012, which designates the U.S., and which claims benefit under 35 U.S.C. § 119(e) of U.S. Provisional Application No. 61/484,934 filed May 11, 2011, of U.S. Provisional Application No. 61/608,168 filed Mar. 8, 2012, and of U.S. Provisional Application No. 61/609,974 filed Mar. 13, 2012, the contents of each of which are incorporated fully herein by reference in their entireties.

GOVERNMENT SUPPORT

This invention was made with government support under grant numbers AI067737 and AI051526 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Nov. 18, 2013, is named 701039-069664-US_SL.txt and is 9,177 bytes in size.

FIELD OF THE INVENTION

The present invention relates to molecular genetics, immunology, and microbiology. The present application is generally directed to compositions and methods for preparation of immunogenic compositions. More specifically, an embodiment of the present invention provides for an immunogenic macro-complex comprising at least one protein or peptide antigen attached to a polymer, such as a polysaccharide, which may also be an antigen. In some embodiments, this complex can be used as an immunogenic composition, such as a vaccine, to confer a synergistic humoral and cellular immune response; and in some embodiments, elicits synergistic antibody- and cell-mediated protection against pathogens, e.g., lethal infection and the mucosal carriage of such pathogens.

BACKGROUND OF INVENTION

Vaccines provide prevention of and treatment for a variety of diseases, including microorganism infection, viral infection, and cancers. Current polysaccharide based vaccines, however, are not always effective in the most vulnerable populations. For example, *Streptococcus pneumonia* (pneumococcus) and *Salmonella typhi* infections are two major diseases for children in developing countries. For typhoid fever, licensed Vi polysaccharide vaccines are ineffective in children under two-years-old. Nevertheless, the success of polysaccharide-based vaccines and passive immunization for the prevention of colonization or disease has demonstrated the importance of capsular antibodies, in particular in controlling disease caused by *S. pneumoniae*. Further, studies in both animals and humans demonstrate that antibodies elicited from pneumococcal vaccination can protect against nasopharyngeal (NP) pneumococcal colonization, which precedes pneumococcal disease.

A limitation of the current polysaccharide pneumococcal vaccines is that protection by anticapsular antibody is limited by its serotype specificity. For example, although the 7-valent pneumococcal conjugate vaccine (PCV7) has significantly reduced the incidence of invasive pneumococcal disease due to vaccine-type (VT) strains, recent studies have shown that non-VT serotypes are gradually replacing VT pneumococcal populations, potentially limiting the usefulness of the vaccine. This has led to the evaluation of whether pneumococcal colonization can be prevented by immunization with conserved antigens. In particular, several pneumococcal proteins have been evaluated as vaccine candidates in animal models of pneumococcal colonization. Mucosal immunization with some of these proteins has been shown to elicit systemic and mucosal antibodies and to confer protection against pneumococcal disease and colonization. There remains a need for an immunogenic composition that includes both pneumococcal polysaccharides and proteins, capable of raising both robust cellular and humoral immune responses to all pneumococcal serotypes.

Additionally, the innate immune response provides rapid and usually effective defense against microbial pathogens. This response involves cellular recognition of pathogen-associated molecules, triggering production and release of inflammatory mediators, recruitment of leukocytes, and activation of antimicrobial effectors. The Toll-like receptors (TLRs), of which at least eleven have been described for mammals, are capable of discriminating among a wide variety of pathogen-associated molecules and eliciting protective responses. For example, TLR4 recognizes many microbial products, including those from gram-negative bacteria, the F protein of respiratory syncytial virus, and cholesterol-dependent cytolysins (CDC) of gram-positive bacteria. Additionally, TLR2 recognizes a large number of microbial and synthetic compounds. Thus, inclusion of such TLR agonists may enhance the immune response to vaccines. There remains a need to improve the efficacy of vaccines by eliciting an innate immune response (TLR-mediated or other) against infections such as pneumococcal colonization and disease.

SUMMARY OF THE INVENTION

The present invention provides for an immunogenic multiple antigen presenting system (MAPS), useful for the production of immunogenic compositions, such as those useful in vaccines. In particular, the present invention relates to compositions comprising an immunogenic complex comprising at least one type of polymer, e.g., a polysaccharide, that can, optionally, be antigenic; at least one antigenic protein or peptide; and at least one complementary affinity-molecule pair comprising (i) a first affinity molecule that associates with the polymer, and (ii) a complementary affinity molecule that associates with the protein or peptide; such that the first and complementary affinity molecules serve as an indirect link between the polymer with the antigenic protein or peptide. Accordingly, the polymer can attach at least 1, or at least 2, or a plurality of the same or different protein or peptide antigens. In some embodiments, the polymer is antigenic, e.g., the polymer is a pneumococcal capsular polysaccharide. In some embodiments, the protein or peptide antigens are recombinant protein or peptide antigens.

The immunogenic compositions as disclosed herein can elicit both humoral and cellular responses to one or multiple antigens at the same time. The immunogenic compositions provide for a long-lasting memory response, potentially protecting a subject from future infection. This allows for a single immunogenic composition that raises a high titer of functional anti-polysaccharide antibody, and is similar or compares favorably with the antibody level induced by conventional conjugate vaccine. Moreover, there is no restriction to specific carrier protein, and various antigen proteins can be used in MAPS construct to generate a robust anti-polysaccharide antibody response. Additionally, the strong antibody response and Th17/Th1 responses are specific to multiple protein antigens presented via the MAPS composition. This presents a major advantage, as a means for eliciting two forms of immunity with one construct. In addition to a more conventional immune response to an antigenic polysaccharide conjugated to a protein carrier, the present invention provides for a T-cell response and, more specifically, Th17 and Th1 responses to proteins injected systemically. Moreover, the present immunogenic composition can incorporate ligands onto the polymer backbone. This provides a potential to enhance specific B-cell or T-cell responses by modifying protein/polymer ratio, complex size, or by incorporating specific co-stimulatory factor, such as TLR2/4 ligands, etc., into the composition.

Compared with typical conjugation technology, which involves harsh treatment of proteins, the present methods avoid risk of denaturation of other modification of the peptide antigen. This provides a substantial advantage of preserving the antigenicity of the included proteins and increases the probability that the protein itself will serve as an antigen (rather than just a carrier). Similarly, the present methods avoid unnecessary modification/damage of the polysaccharide backbone, because there is no heavy chemical cross-linking: biotinylation can be precisely controlled to react with specific functional groups of the polysaccharide, and the biotinylation level can be easily adjusted. This is advantageous in avoiding the typical process of conjugation, that results in damage to critical side chains or epitopes, which may cause reduced immunogenicity and protection.

The present the affinity-based assembly provides easy and highly flexible preparation of the immunogenic composition. It is highly specific and stable; it can remain in the cold for months and retain its potency. The assembly process is simple enough to ensure high reproducibility; there are only a few steps required, which reduces the risk of lot-to-lot variation, of great industrial advantage. The MAPS assembly is highly efficient (over 95%), even at low concentrations of protein and polysaccharide (such as 0.1 mg/ml); this is a major advantage, because inefficiencies in conjugate manufacture (typically efficiencies are in the <50% range) represent a major hurdle and reason for the high cost of vaccines. For formulation: it is easy to adjust the composition and physical properties of the final product. The protein:polymer ratio in the complex is adjustable; with moderate biotinylation of polymer, protein:polymer can be 10:1 (w/w) or more; conversely, the ratio can be 1:10 or less if such is the interest based on immunological goals. Additionally, the size of the immunogenic MAPS composition can be adjusted by the choice of polymer size. The methods of making the MAPS provide for ease in combining proteins and polymers with little modification. The possible multivalency of final product by loading multiple protein antigens, from the same or different pathogens (e.g., pneumococcus and tuberculosis), in single immunogenic construct, provides for a composition that can be used to decrease the number of vaccines required to immunize a subject against more than one disease. Moreover, the MAPS composition is highly stable; becoming dissociated only upon boiling and maintaining immunogenicity even after many months at 4° C. The immunogenicity of the MAPS complex may be limited by the stability of the antigenic protein or peptide component, which stability may be extended by inclusion in the MAPS complex. The specific antigens used herein exhibited stability at room temperature and after at least one freeze-thaw cycle. This provides an important advantage over current vaccines that are compromised if the "cold chain" is not maintained carefully.

Accordingly, one aspect of the present invention relates to an immunogenic composition comprising a polymer, at least one protein or peptide antigen, and at least one complementary affinity-molecule pair, where the complementary affinity-molecule pair comprises a first affinity molecule that associates with the polymer and a complementary affinity molecule that associates with the protein or peptide antigen, so that when the first affinity molecule associates with the complementary affinity molecule, it indirectly links the antigen to the polymer.

In some embodiments, the first affinity molecule is cross-linked to the polymer with a cross-linking reagent, for example, a cross-linking reagent selected from CDAP(1-cyano-4-dimethylaminopyridinium tetrafluoroborate), EDC (1-Ethyl-3-[3-dimethylaminopropyl]carbodiimide hydrochloride), sodium cyanoborohydride; cyanogen bromide; or ammonium bicarbonate/iodoacetic acid. In some embodiments, the first affinity molecule is cross-linked to carboxyl, hydroxyl, amino, phenoxyl, hemiacetal, and mecapto functional groups of the polymer. In some embodiments, the first affinity molecule is covalently bonded to the polymer.

In some embodiments, the first affinity molecule is biotin or a derivative thereof, or a molecule with similar structure or physical property as biotin, for example, an amine-PEG3-biotin ((+)-biotinylation-3-6,9-trixaundecanediamine) or derivative thereof.

In some embodiments, the protein or peptide antigen of the immunogenic composition is a fusion protein comprising the antigenic protein or peptide fused to the complementary affinity binding molecule. The fusion can be a genetic construct, i.e., a recombinant fusion peptide or protein. In some embodiments, an antigen can be covalently attached as a fusion protein to the complementary affinity molecule. In alternative embodiments, the antigen is non-covalently attached to the complementary affinity molecule.

In some embodiments, the complementary affinity molecule is a biotin-binding protein or a derivative or a functional portion thereof. In some embodiments, a complementary affinity molecule is an avidin-like protein or a derivative or a functional portion thereof, for example but not limited to, rhizavidin or a derivative thereof. In some embodiments, a complementary affinity molecule is avidin or streptavidin or a derivative or a functional portion thereof.

In some embodiments, a secretion signal peptide is located at the N-terminus of the avidin-like protein. Any signal sequence known to persons of ordinary skill in the art can be used; and in some embodiments, the signal sequence is MKKIWLALAGLVLAFSASA (SEQ ID NO:1) or a derivative or functional portion thereof. In some embodiments, the antigen can be fused to a complementary affinity molecule via a flexible linker peptide, where the flexible linker peptide attaches the antigen to the complementary affinity molecule.

In some embodiments, the polymer component of the immunogen comprises a polymer derived from a living organism, e.g., a polysaccharide. In some embodiments, a polymer can be purified and isolated from a natural source, or is can be synthesized as with a natural composition/structure, or it can be a synthetic (e.g., with an artificial composition/structure) polymer. In some embodiments, a polymer is derived from an organism selected from the group consisting of: bacteria, archaea, or eukaryotic cells like fungi, insect, plant, or chimeras thereof. In some embodiments, the polymer is a polysaccharide derived from a pathogenic bacterium. In specific embodiments the polysaccharide is a pneumococcal capsular polysaccharide, a pneumococcal cell-wall polysaccharide, or a *Salmonella typhi* Vi polysaccharide.

In some embodiments, a polymer of the immunogenic composition as disclosed herein is branched chain polymer, e.g., a branched polysaccharide, or alternatively, can be a straight chain polymer, e.g., a single chain polymer, e.g., polysaccharide. In some embodiments, the polymer is a polysaccharide, for example, dextran or a derivative thereof. In some embodiments, a polymer, e.g., dextran polysaccharide can be of average molecular weight of 425kD-500 kDa, inclusive, or in some embodiments, greater than 500 kDa. In some embodiments, a polymer, e.g., dextran polysaccharide can be of average molecular weight of 60kD-90 kDa, inclusive, or in some embodiments, smaller than 70 kDa. The dextran polymer can be derived from a bacterium, such as *Leuconostoc mesenteroides*.

In some embodiments, an immunogenic composition as disclosed herein comprises at least 2 antigens, or at 3 least antigens, or at least 5 antigens, or between 2-10 antigens, or between 10-15 antigens, or between 15-20 antigens, or between 20-50 antigens, or between 50-100 antigens, or more than 100 antigens, inclusive. In some embodiments, where an immunogenic composition as disclosed herein comprises at least 2 antigens, the antigens can be the same antigen or at least 2 different antigens. In some embodiments, the antigens can be from the same or different pathogens, or can be different epitopes or parts of the same antigenic protein, or can be the same antigen which is specific to different serotypes or seasonal variations of the same pathogen (e.g., influenza virus A, B, and C).

In some embodiments, an immunogenic composition as disclosed herein comprises an antigen from a pathogenic organism or an abnormal tissue. In some embodiments, the antigen is a tumor antigen. In some embodiments, an antigen can be at least one antigen selected from antigens of pathogens or parasites, such as antigens of *Streptococcus pneumoniae, Mycobacterium tuberculosis* or *M. tetanus, Bacillus anthracis*, HIV, seasonal or epidemic influenza antigens (such as H1N1 or H5N1), *Bordetella pertussis, Staphylococcus aureus, Neisseria meningitides* or *N. gonorrhoeae*, HPV, *Chlamydia trachomatis*, HSV or other herpes viruses, or *Plasmodia* sp. These antigens may include peptides, proteins, glycoproteins, or polysaccharides. In some embodiments, the antigen is a toxoid or portion of a toxin.

In some embodiments, an immunogenic composition as disclosed herein comprises an antigenic polysaccharide, for example, such as Vi antigen (*Salmonella typhi* capsular polysaccharide), pneumococcal capsular polysaccharides, pneumococcal cell wall polysaccharide, Hib (*Haemophilus influenzae* type B) capsular polysaccharide, meningococcal capsular polysaccharides, the polysaccharide of *Bacillus anthracis* (the causative agent of anthrax), and other bacterial capsular or cell wall polysaccharides, or any combinations thereof. The polysaccharide may have a protein component, e.g., a glycoprotein such as those from viruses.

In some embodiments, an immunogenic composition as disclosed herein further comprises at least one co-stimulation factor associated with the polymer or polysaccharide, where the co-stimulation factor can be associated directly or indirectly. For example, in some embodiment, a co-stimulation factor can be covalently attached to the polymer. For example, in some embodiments, a co-stimulation factor can be covalently attached to the first affinity molecule, which is then cross-linked to the polymer. For example, in some embodiments, a co-stimulation factor can be attached to a complementary affinity molecule, which associates with a first affinity molecule to link the co-stimulation factor to the polymer. In some embodiments, a co-stimulation factor is an adjuvant. In alternative embodiments, a co-stimulatory factor can be any known to one of ordinary skill in the art, and includes any combination, for example, without limitation, Toll like receptor agonists (agonists for TLR2, 3, 4, 5, 7, 8, 9, etc.), NOD agonists, or agonists of the inflammasome.

Another aspect of the present invention relates to the use of the immunogenic composition as disclosed herein to be administered to a subject to elicit an immune response in the subject. In some embodiments, the immune response is an antibody/B cell response, a $CD4^+$ T-cell response (including Th1, Th2 and Th17 cells) and/or a $CD8^+$ T-cell response. In some embodiments, at least one adjuvant is administered in conjunction with the immunogenic composition.

Another aspect of the present invention relates to a method for inducing an immune response in a subject to at least one antigen, comprising administering to the subject the immunogenic composition as disclosed herein.

Another aspect of the present invention relates to a method of vaccinating an animal, e.g., a bird, a mammal or a human, against at least one antigen comprising administering a vaccine composition comprising the immunogenic composition as disclosed herein.

In all aspects as disclosed herein, an animal or a subject can be a human. In some embodiments, the subject can be an agricultural or non-domestic animal, or a domestic animal. In some embodiments, a vaccine composition comprising the immunogenic composition as disclosed herein can be administered via subcutaneous, intranasal, oral, sublingual, vaginal, rectal, intradermal, intraperitoneal, intra muscular injection, or via skin-patch for transcutaneous immunization.

In all aspects as disclosed herein, an immune response is an antibody/B-cell response, a $CD4^+$ T-cell response (including Th1, Th2 and Th17 responses) or a CD8+ T-cell response against protein/peptide antigen(s). In some embodiments, an immune response is an antibody/B-cell response against the polymer, e.g., a pneumococcal polysaccharide. In some embodiments, at least one adjuvant is administered in conjunction with the immunogenic composition.

Another aspect of the present invention relates to the use of the immunogenic composition as disclosed herein for use in a diagnostic for exposure to a pathogen or immunogenic agent.

Another aspect of the present invention relates to kits for preparing an immunogenic composition as disclosed herein. For example, such kits can comprise any one or more of the following materials: a container comprising a polymer, e.g., a polysaccharide, cross-linked with a plurality of first affinity molecules; and a container comprising a complementary affinity molecule which associates with the first affinity molecule, wherein the complementary affinity molecule associates with an antigen.

In another embodiment, the kit can comprise a container comprising a polymer, e.g., a polysaccharide; a container comprising a plurality of first affinity molecules; and a container comprising a cross-linking molecule for crosslinking the first affinity molecules to the polymer. In some embodiments, the kit can comprise at least one co-stimulation factor which can be added to the polymer. In some embodiments, the kit comprises a cross-linking reagent, for example, but not limited to, CDAP(1-cyano-4-dimethylaminopyridinium tetrafluoroborate), EDC (1-Ethyl-3-[3-dimethylaminopropyl]carbodiimide hydrochloride), sodium cyanoborohydride; cyanogen bromide; ammonium bicarbonate/iodoacetic acid for linking the co-factor to the polymer or polysaccharide. In some embodiments, the kit further comprises a means to attach the complementary affinity molecule to the protein or peptide antigen, where the means can be by a cross-linking reagent or by some intermediary fusion protein.

In some embodiments, the kit can comprise a container comprising an expression vector for expressing a protein or peptide antigen-affinity molecule fusion protein, for example, an expression vector for expressing the protein or peptide antigen as a fusion protein with the complementary affinity molecule. In some embodiments, the vector can optionally comprise a sequence for a linker peptide, wherein the expression vector can expresses an antigen-complementary affinity molecule fusion protein comprising a linker peptide located between the antigen and the affinity molecule.

In some embodiments, the kit can optionally comprise a container comprising a complementary affinity molecule which associates with the first affinity molecule, wherein the complementary affinity molecule associates with a peptide/protein antigen. In some embodiments, the kit can additionally further comprise a means to attach the complementary affinity molecule to the antigen, e.g., using a cross-linking regent as disclosed herein or other intermediately protein, such as a divalent antibody or antibody fragment.

Provided herein also is a method of vaccinating a subject, e.g., a mammal, e.g., a human with the immunogenic compositions as disclosed herein, the method comprising administering a vaccine composition as disclosed herein to the subject.

DESCRIPTION OF THE DRAWINGS

FIGS. 3A-3C show an embodiment of a recombinant rhizavidin and rhizavidin-antigen fusion protein. FIG. 3A shows a schematic of the construction of modified rhizavidin (upper (SEQ ID NOS 29-30, respectively, in order of appearance)) and rhizavidin-antigen fusion protein (lower (SEQ ID NOS 29, 27 and 31, respectively, in order of appearance)). All constructs were cloned into PET21b vector and transformed into E. coli BL21 (DE3) strain for expression. FIG. 3B shows SDS-PAGE of purified recombinant rhizavidin (rRhavi). FIG. 3C shows SDS-PAGE of purified rhavi-antigen fusion proteins. Lane 1, rhavi-Pdt; lane 2, rhavi-PsaA; lane 3, rhavi-sp1733; lane 4, rhavi-sp1534; lane 5, rhavi-sp0435; lane 6, rhavi-sp1458; lane 7, rhavi-ESAT-6/Cfp10; lane8, rhavi-TB9.8/TB10.4; lane 9, rhavi-MPT64; lane 10, rhavi-MPT83.

FIGS. 4A-4C show the elution profile of an assembled example MAPS. FIG. 4A MAPS was assembled by incubating 0.5 mg of purified rRhavi with 1 mg of biotinylated dextran 90 (BD90, average MW 60-90 KD) at 4° C. overnight and then applied to a superdex-200 column. Peak A and Peak B indicated the eluted fractions containing MAPS complex, Peak C indicated the eluted fractions containing free rRhavi. FIG. 4B shows SDS-PAGE of peak fractions. All samples were boiled in SDS sample buffer with 10 mM DTT. FIG. 4C shows the stability of MAPS complex. Equal amounts of sample were treated and then applied to SDS-PAGE. MAPS complex remains intact even after treatment of SDS sample buffer containing reducing reagent (lane 1) and can only be broken after boiling, attesting to the stability of the association. Lane 1, MAPS treated with SDS sample buffer containing 10 mM DTT, room temperature for 10 min; lane 2, MAPS treated with SDS sample buffer without DTT, boiled for 10 min; lane 3, MAPS treated with SDS sample buffer containing 10 mM DTT, boiled for 10 min.

FIG. 5 shows assembly of MAPS complex at different temperature and at different concentration of PS and protein antigen. MAPS complex can be effectively assembled at a wide range of concentrations of polysaccharide (PS) or protein antigen (as low as 0.1 mg/ml). The assembly can be done by overnight incubation at 4° C.

FIG. 8A shows MAPS assembly with two antigens at different ratios. Bivalent MAPS complex were prepared by incubating biotinylated *S. pneumoniae* (SP) serotype 14 capsular polysaccharide with two different pneumococcal fusion antigens rhavi-1652 and rhavi-0757 mixed at a molar ratio of 1:4, 1:2, 1:1, 2:1, or 4:1. SDS-PAGE showed that the amounts of each antigen incorporated into the MAPS complex were well correlated to the input ratios. FIGS. 8B-8D show multivalent MAPS complex that were made with biotinylated polysaccharide (dextran, or serotype 3 pneumococcal capsular polysaccharide) connecting two (2V, FIG. 8B), three (3V, FIG. 8C) or five (5V, FIG. 8D) different pneumococcal and/or tuberculosis antigens. SDS-PAGE showed the antigens incorporated into MAPS complex. All samples were boiled in SDS sample buffer with 10 mM DTT.

FIG. 11 shows that the anti-PS antibodies generated by immunization with MAPS complex facilitate the killing of the target pathogens in vitro. FIGS. 11B-11D: Serum from mice immunized with Alum (dashed line); PCV13 (black line); or MAPS (gray line).

FIG. 12A shows the results of serum IgG antibodies measured against PsaA or Pdt 2 weeks after the last immunization. Mice immunized with MAPS complex made significantly higher titer of anti-Pdt and anti-PsaA antibodies than mice that received the mixture. Antigen specific T-cell responses were evaluated by in vitro stimulation of the whole blood of immunized animals. IL-17A (FIG. 12B) and IFN-γ (FIG. 12C) production in vitro was measured in blood samples incubated 6 days with either purified PsaA, Pdt, or pneumococcal whole-cell antigen (WCA). Compared to the mice immunized with the mixture, the animals that received MAPS complex showed significantly stronger IL-17A and IFN-γ response. FIG. 12D shows a correlation of IL-17A and IFN-γ production by stimulation of WCA. For all panels, bars represent means with standard deviation and statistical analysis was performed using Mann-Whitney test, or using Spearman R for correlation.

FIG. 15D shows the antibody responses to different TB protein antigens. FIGS. 15E-15F show strong IL-17A (FIG. 15E) and IFN-γ (FIG. 15F) associated T cell responses in whole blood sample from MAPS immunized mice after in vitro stimulation with purified TB protein antigens. FIGS. 15G and 15H show the IL-17A (FIG. 15G) and IFN-γ (FIG. 15H) associated T-cell responses of splenocytes from MAPS immunized animals to the mixture of purified TB protein antigens or to the TB whole cell extract. FIGS. 15I and 15J provide further data regarding the TB-specific memory/effector T-cells induced by immunization with MAPS. The results showed that depletion of CD4+ T-cells but not CD8+ T cells had a significant impact on the TB antigen specific cytokine production, indicating that immunization with MAPS vaccine had primed mainly a CD4+ T-cell (T helper cell) immune response.

DETAILED DESCRIPTION OF THE INVENTION

Figure 1:
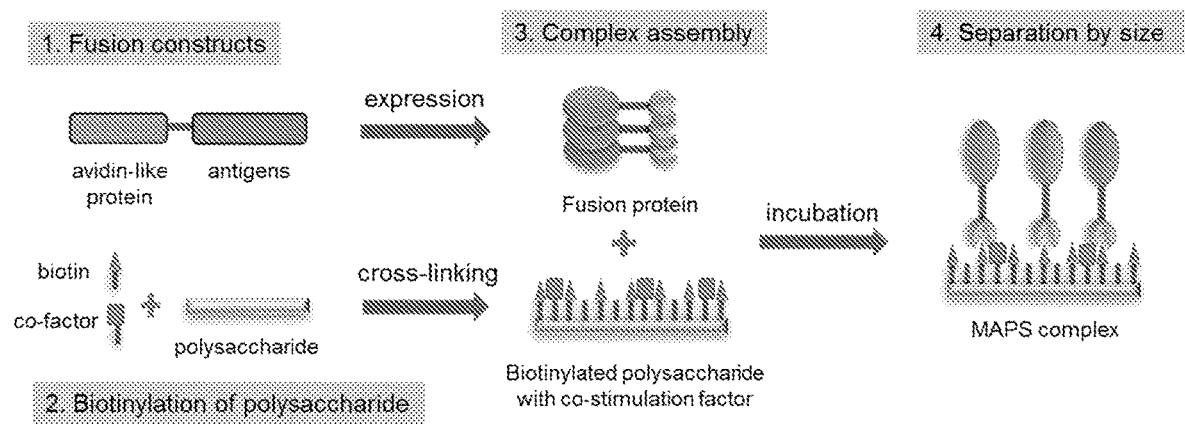
FIG. 1 is a schematic diagram of multiple antigen presenting system (MAPS). MAPS represents a novel platform of a complex immunogenic composition, that is made by attaching a number of protein antigens to a polysaccharide or polysaccharide antigen via a stable interaction of an affinity pair, such as avidin-biotin pair. In one embodiment of the MAPS complex, the protein antigens from one or different pathogens are recombinantly fused to an avidin-like protein and expressed in E. coli. The polysaccharide backbone, which may be chosen from a variety of pathogens, is biotinylated and/or cross-linked with or without co-stimulation factors using 1-Cyano-4-dimethylaminopyridinium tetrafluoroborate (CDAP) or 1-ethyl-3-[3-dimethyl-aminopropyl]carbodiimide hydrochloride (EDC) as an activating reagent. A MAPS complex can be assembled readily by just mixing and incubating the purified fusion antigens, one or multiple, at the desired ratio, with biotinylated polysaccharide. Assembled MAPS complex can be purified/separated according to size by gel filtration chromatography.
Figure 2:
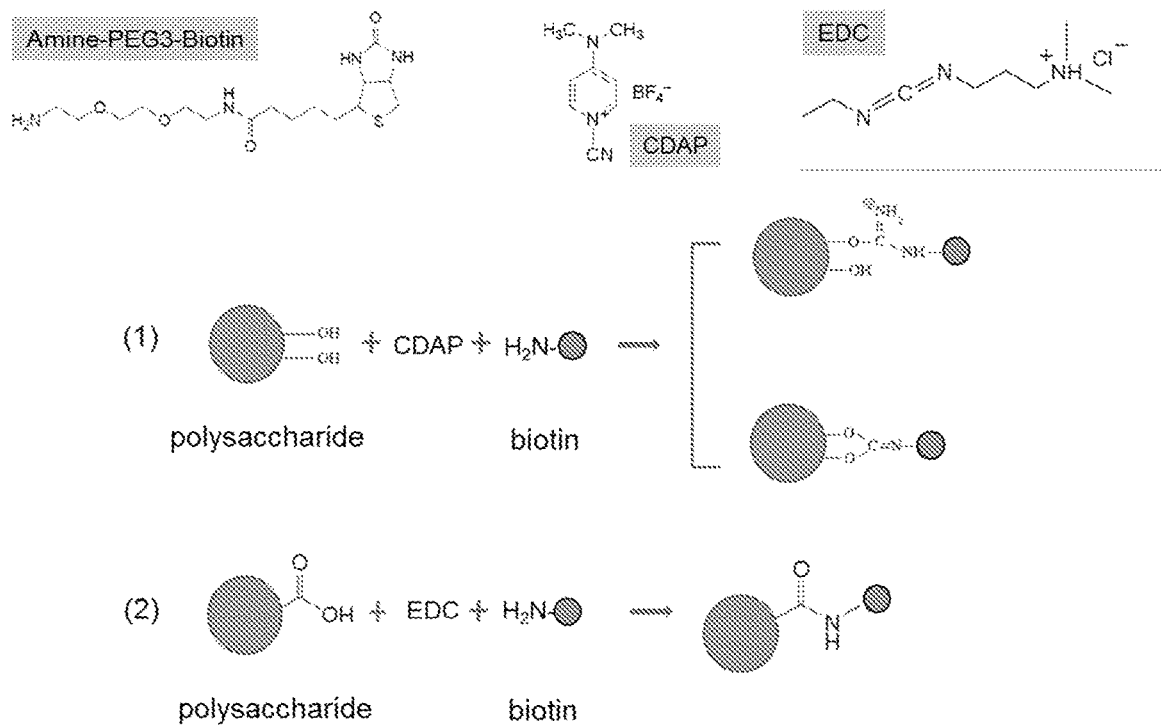
FIG. 2 shows exemplary examples of biotinylation of polysaccharide: the structures of the biotin derivative, amine-PEG3-biotin (also known as (+)-biotinylation-3-6,9-trixaundecanediamine); the structure of CDAP; and the structure of EDC. Figure also shows a schematic for the method of biotinylation of polysaccharides using CDAP as the activating reagent, process (1) or using EDC as the activating reagent, process (2). Other procedures for biotinylation are encompassed in the methods of the invention.
Figure 4B:
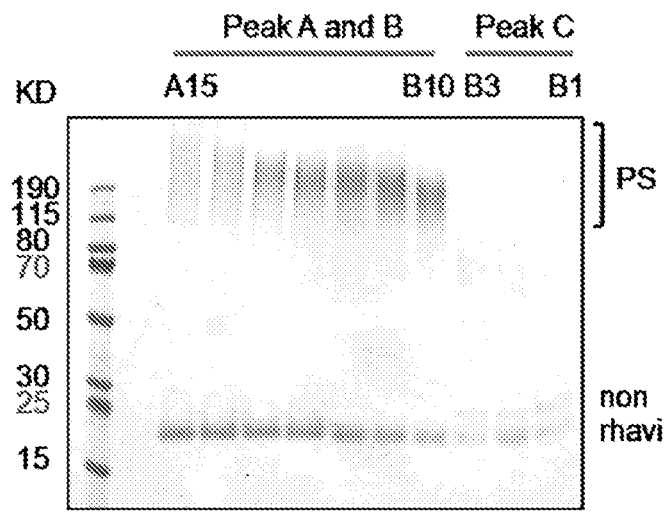
Figure 4C:
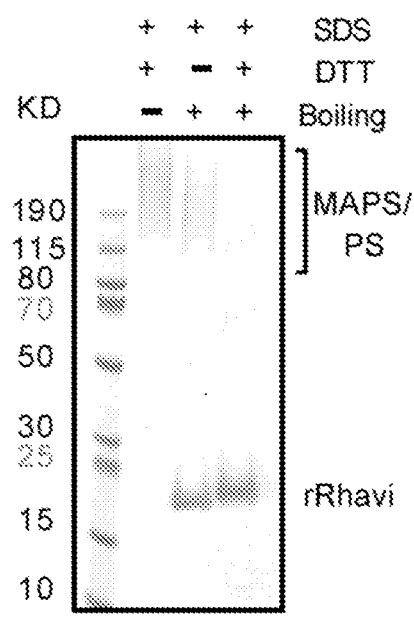
Figure 5A:
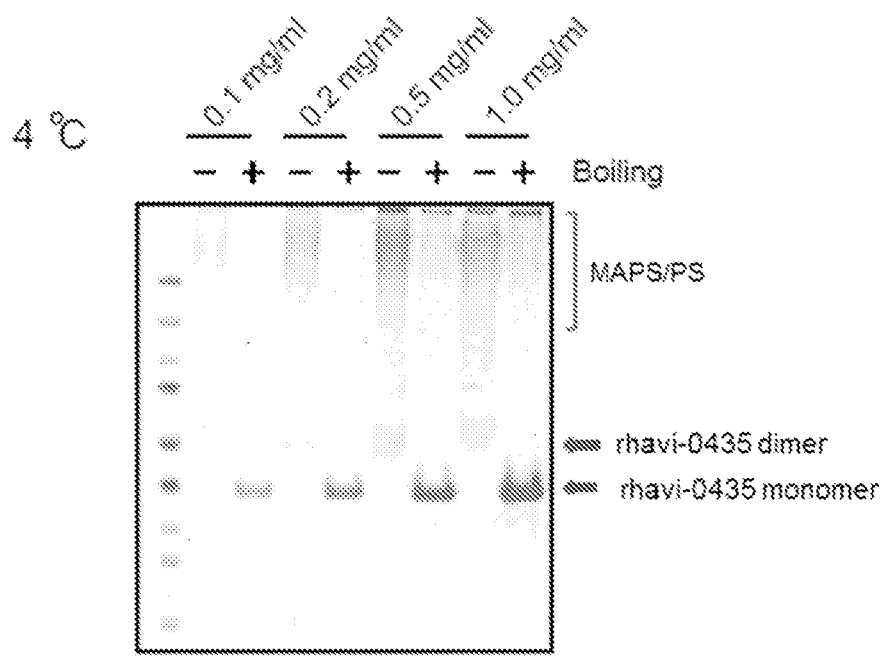
(FIG. 5A) or at 25° C.
Figure 5B:
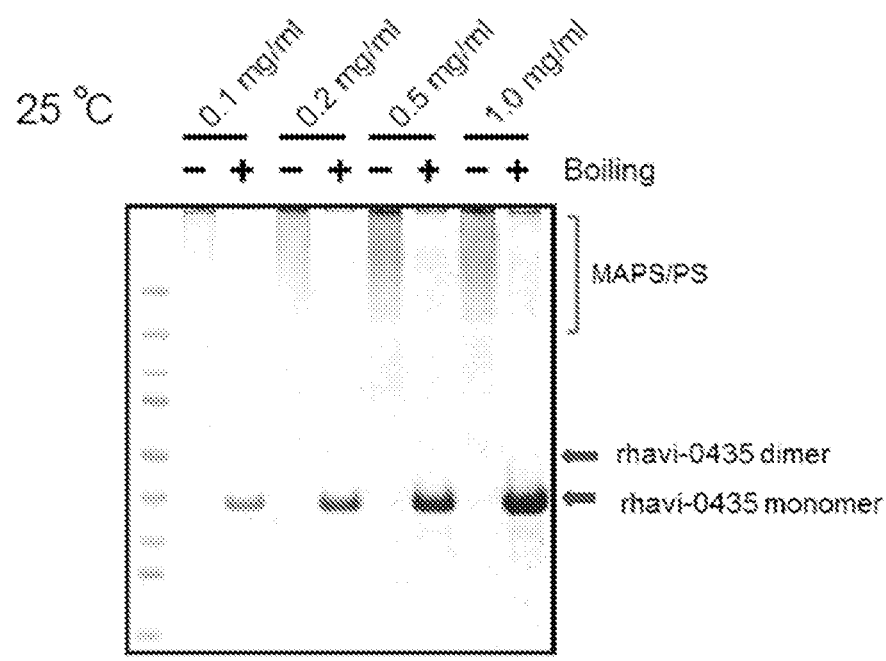
(FIG. 5B), depending on the stability of the antigens. The assembly efficiency of MAPS complex can be estimated by running the assembling mixture through SDS-PAGE, with or without boiling the sample beforehand. Without boiling treatment, the protein antigens that were incorporated into MAPS complex stay on the PS and thus show up as bands of very large molecular weight on the gel (MAPS/PS); only the unbound proteins would run lower on the gel and detected at the expected molecular weight of the antigen (monomer or dimer position). By comparison of the protein antigen band before and after boiling, the percentage of the antigens assembled into MAPS complex could be estimated. In general, the assembling efficiency at 4° C. is greater than 85%, and at 25° C., it is close to 95%-99%.
Figure 6:
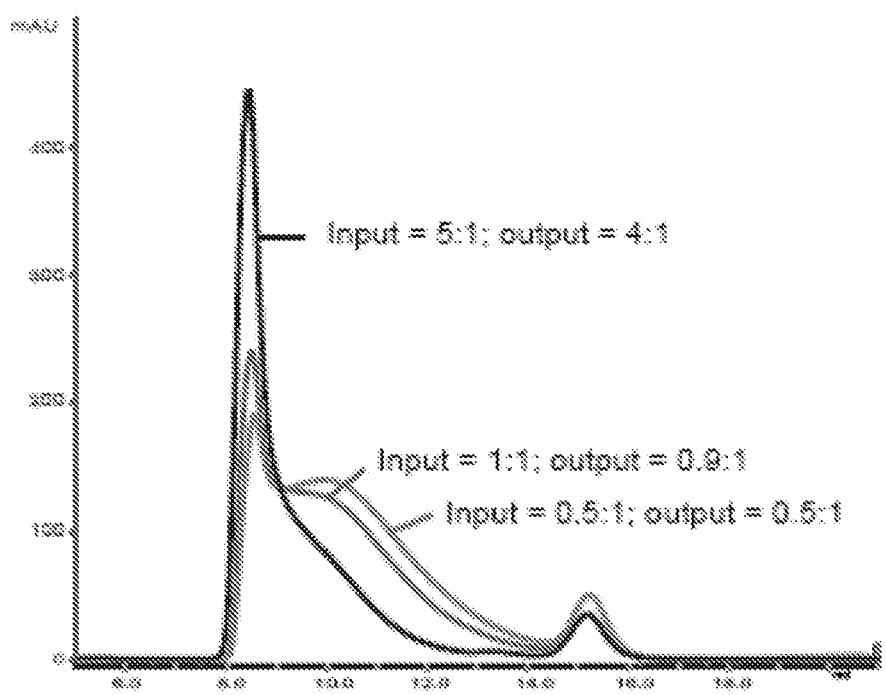
FIG. 6 shows elution profiles of MAPS assembled with different ratios of protein vs. polysaccharide. 0.5 mg of purified rRhavi was incubated overnight with either 1 mg, 0.5 mg or 0.1 mg of BD90, respectively, and then applied to gel filtration chromatography using superdex 200 column. The MAPS complex assembled at higher ratio of protein vs. polysaccharide appeared to have higher molecular weight than the one assembled at lower ratio. Peak fractions containing MAPS complex for each sample (indicated by arrows) were collected. The ratio of protein vs. polysaccharide in the purified MAPS complex was measured and showed good correlation to the input ratio.
Figure 7:
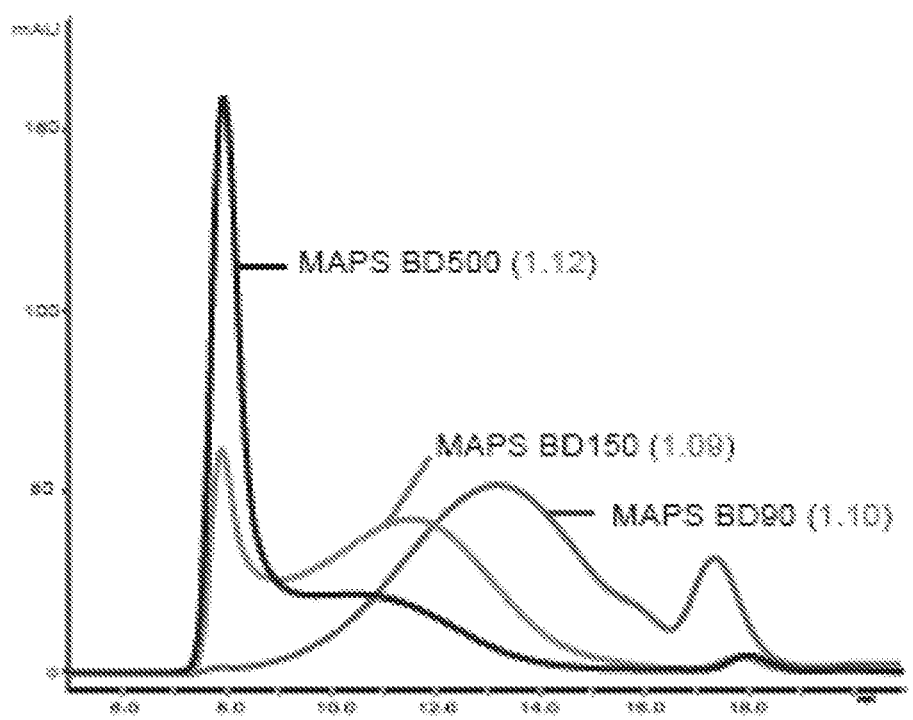
FIG. 7 shows elution profiles of MAPS assembled with various sizes of polysaccharide. 0.5 mg of fusion antigen was incubated with 0.25 mg biotinylated dextran with an average molecular weight of 425-500 KD (BD500), 150 KD (BD150) or 60-90 KD (BD90). The MAPS complex was separated using Superpose 6 column; the chromatography profile showed that the complex assembled with a bigger polysaccharide had a larger size.
Figure 8A:
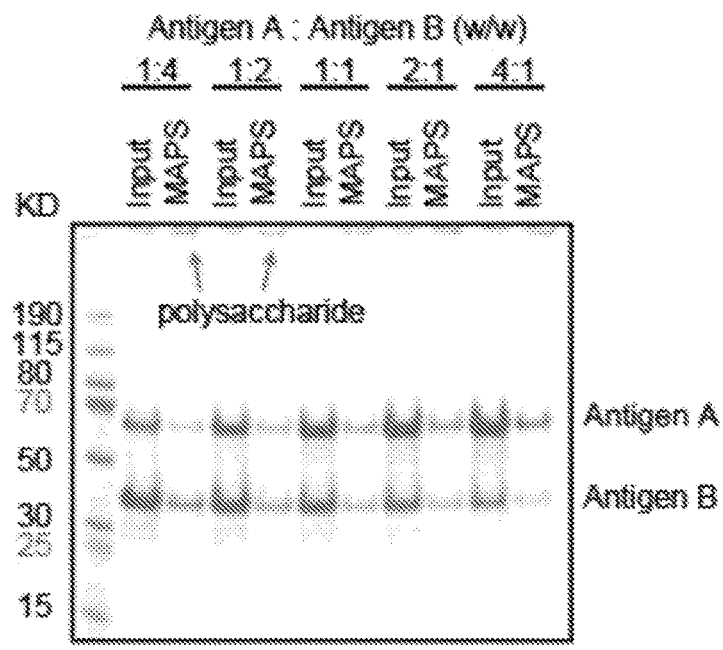
FIG. 8A-8D shows MAPS assembly with multiple antigens.
Figures 8B, 8C, 8D:
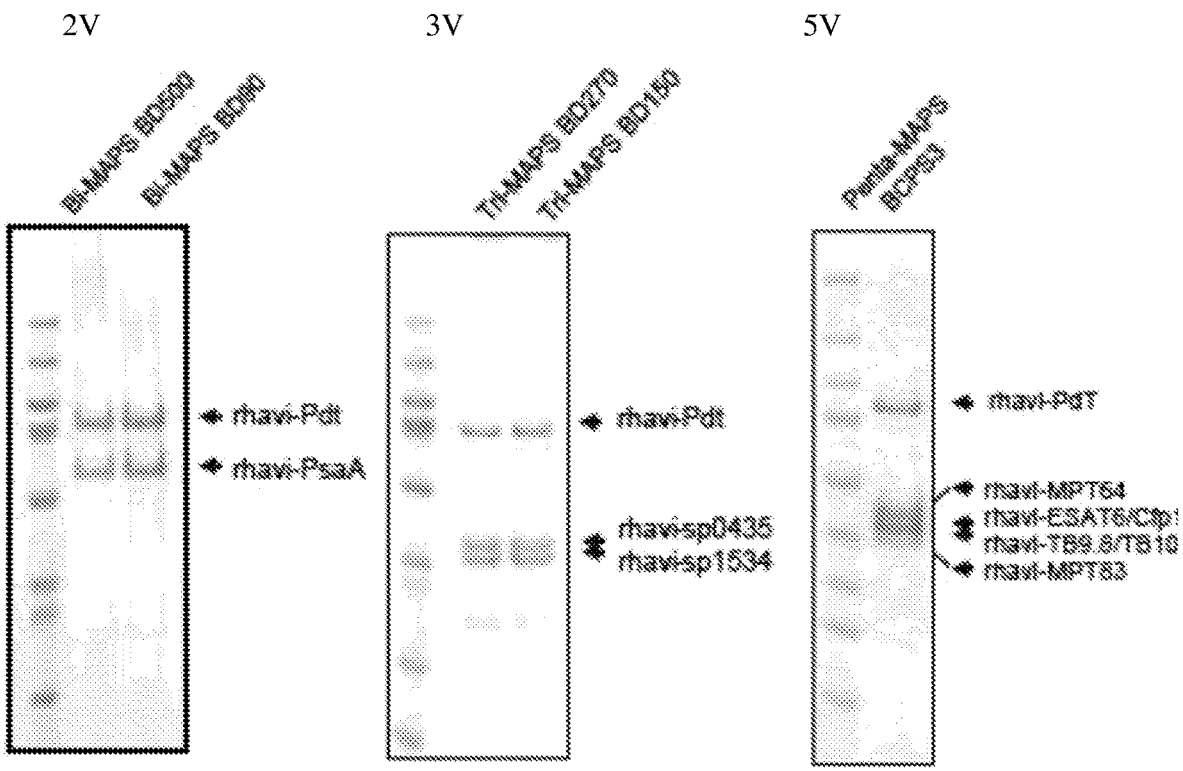
Figure 9A:
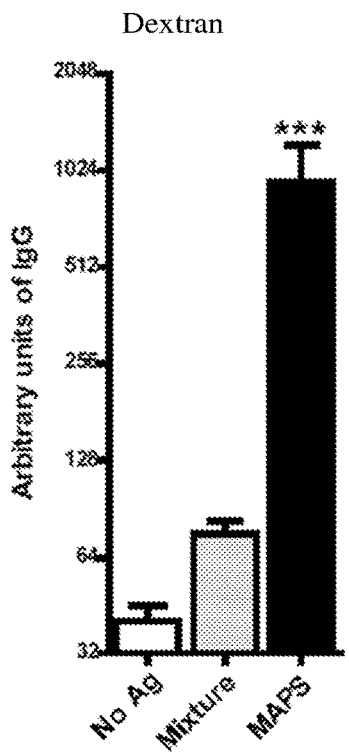
FIG. 9 shows that immunization with a MAPS complex induced a strong antibody response against polysaccharide antigens. Mice that were immunized with MAPS complex made from biotinylated dextran (9A), Vi polysaccharide (9B), or pneumococcal cell wall polysaccharide (CWPS) (9C) made a significant higher amount of anti-polysaccharide antibodies compared to the animal groups that received adjuvant alone (no Ag) or a mixture of uncoupled polysaccharide and proteins (Mixture).
FIGS. 9D-9F show that MAPS complex compares favorably with conventional conjugate vaccine in generating anti-PS Ab. MAPS complexes were made from SP serotype 1, 5, 14 capsular polysaccharide (CPS), loaded with five protein antigens. Mice were subcutaneously immunized with MAPS or Prevnar 13® (Pneumococcal 13-valent Conjugate Vaccine [Diphtheria CRM197 Protein]; Wyeth/Pfizer) (PCV13) twice, 2 weeks apart, and the serum IgG antibody against vaccinated serotype CPS was analyzed 2 weeks after the second immunization by ELISA. The titer of anti-CPS IgG in PCV13 immunized mice was arbitrarily set at 1200 units for comparison. For all tested serotypes, immunization with MAPS complex generated either similar level (serotype 5) or much greater level of anti-CPS IgG antibody (serotype 1 and serotype 14) than what generated by vaccination with PCV13. Serotype 1 (FIG. 9D); Serotype 5 (FIG. 9E); Serotype 14 (FIG. 9F).
Figure 9B:
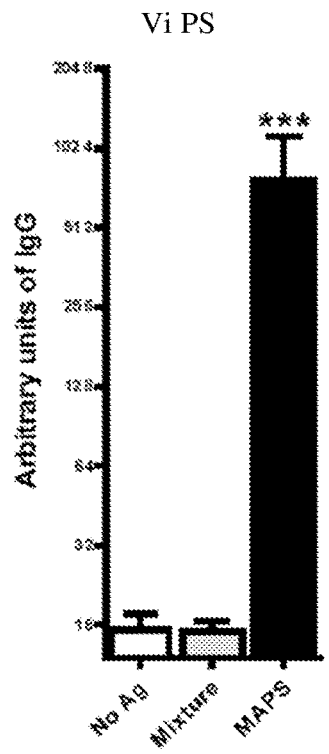
Figure 9C:
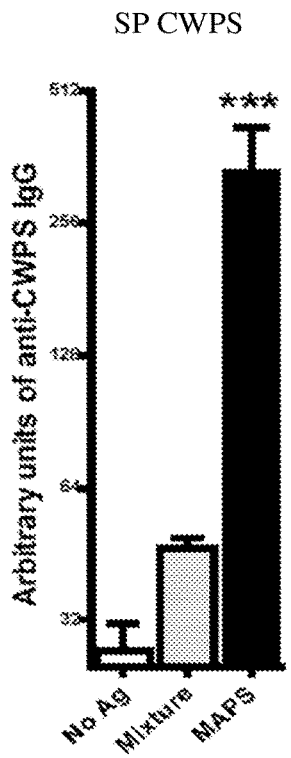
Figure 9D:
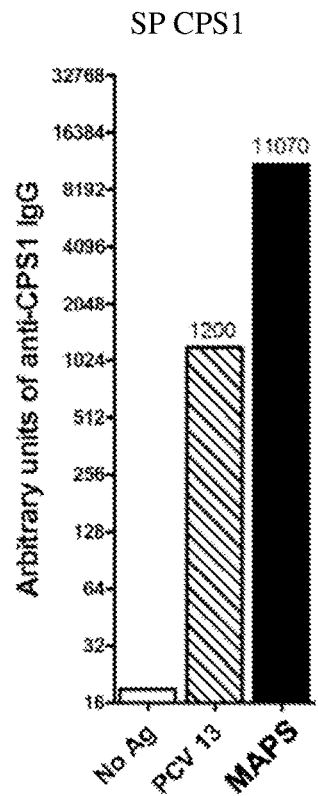
Figure 9E:
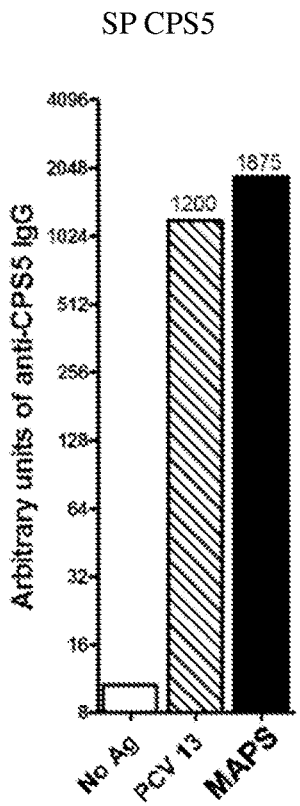
Figure 9F:
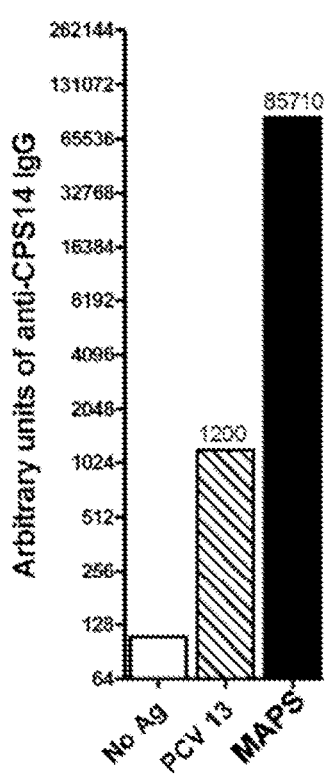
Figure 10:
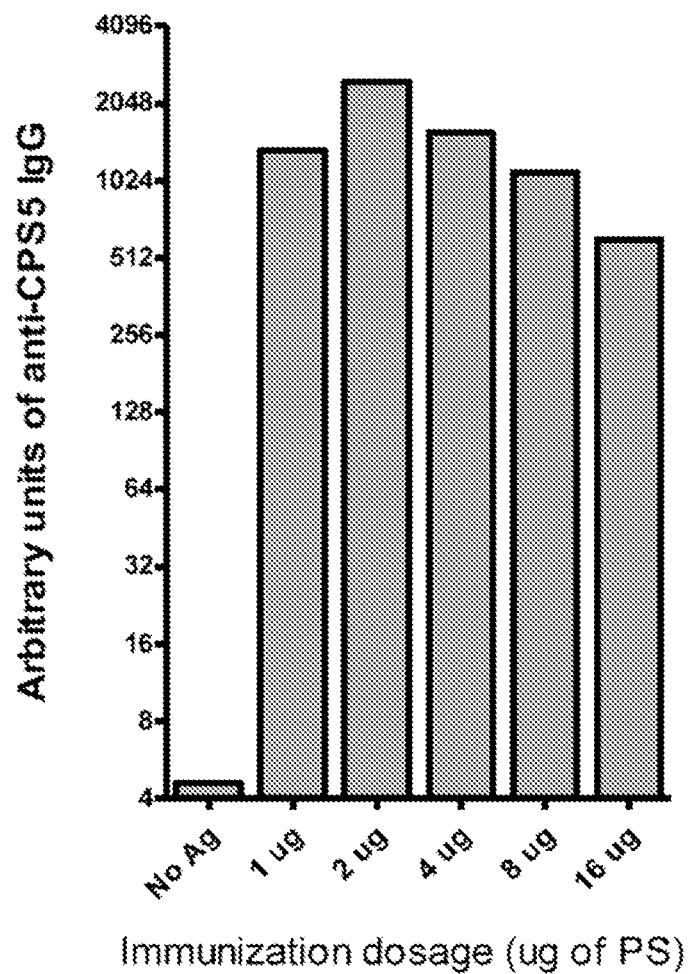
FIG. 10 compares anti-PS antibody induced by MAPS at different immunization dosages. MAPS complex was made from serotype 5 SP CPS loading with five protein antigens. Mice were given with MAPS complex at 1 µg-16 µg of PS content per dose, for two immunizations, two weeks apart. Serum antibody against serotype 5 CPS was measured and compared between different immunization groups two weeks after the second immunization. At all dosages, immunization with MAPS induced robust IgG antibody against serotype 5 CPS. Giving 2 µg of PS per dose generated the highest antibody titer, and increasing PS dosage to 16 µg reduced the antibody titer about 4-fold.
Figure 11A:
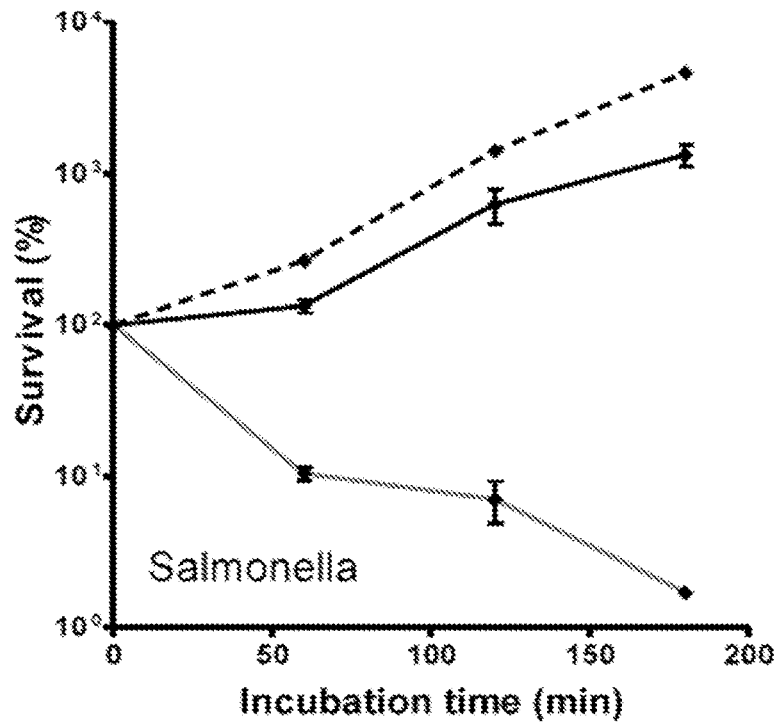
FIG. 11A demonstrates the antibody-mediated killing of the Vi-expressing bacterium. The serum from the animals immunized with MAPS complex (using Vi as the backbone), but not from the two other groups, showed potent killing of the Vi-expressing strain (more than 90% killing) within 1 hour of incubation. Serum from mice immunized with Alum (dashed line); Mixture (black line); or MAPS (gray line).
Figure 11B:
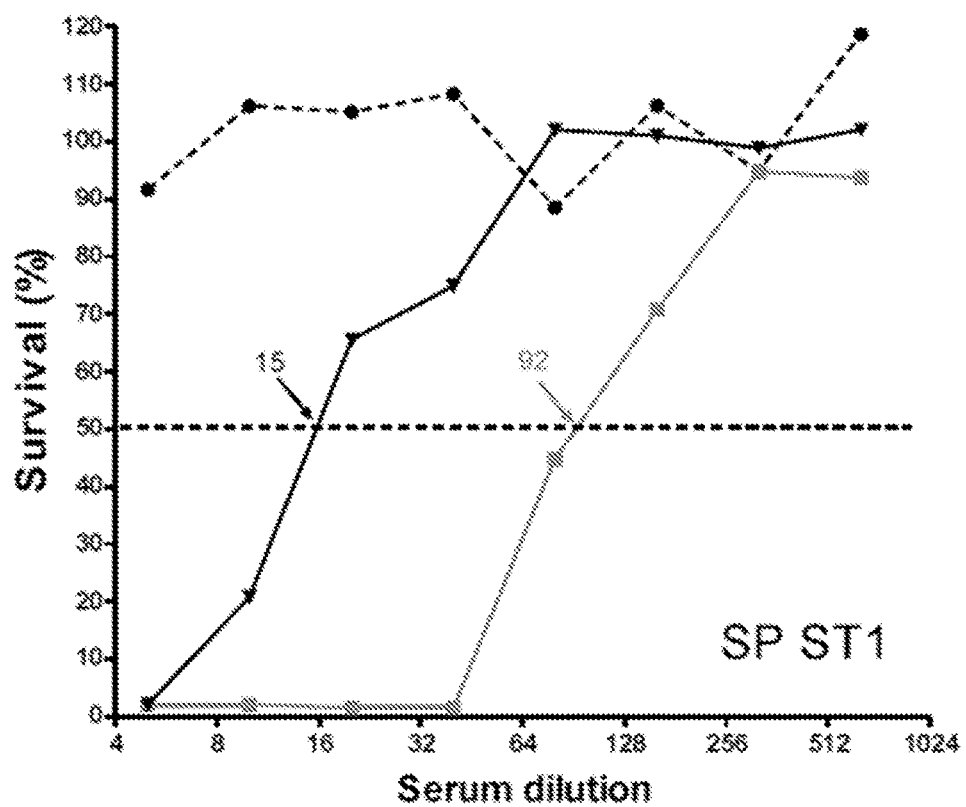
FIGS. 11B-11D demonstrate that opsonophagocytic killing activity of serum from MAPS-immunized mice compares favorably to the killing activity of serum from mice immunized with licensed vaccine PCV13. The ability of the serum from PCV13- or MAPS-immunized mice in mediating in vitro opsonophagocytic killing of pneumococcus by neutrophils was analyzed and compared. Human neutrophils were differentiated from cells in the HL-60 cell line. The opsonophagocytic killing was done by incubating the serum, in different dilutions, with serotype 1 (FIG. 11B), serotype 5 (FIG. 11C) or serotype 13 (FIG. 11D), pneumococcus and differentiated HL-60 cells at 37° C. for 1 hour (in the presence of baby rabbit complement). An aliquot of the mixture was plated after incubation for counting of the survival bacteria. The opsonophagocytic killing unit was defined as the fold dilution of the serum which 50% killing of the bacteria is observed. For all tested serotypes, serum from MAPS immunized mice showed at least 4 times higher killing activity (OPA titer) than serum from PCV13 immunized mice.
Figure 11C:
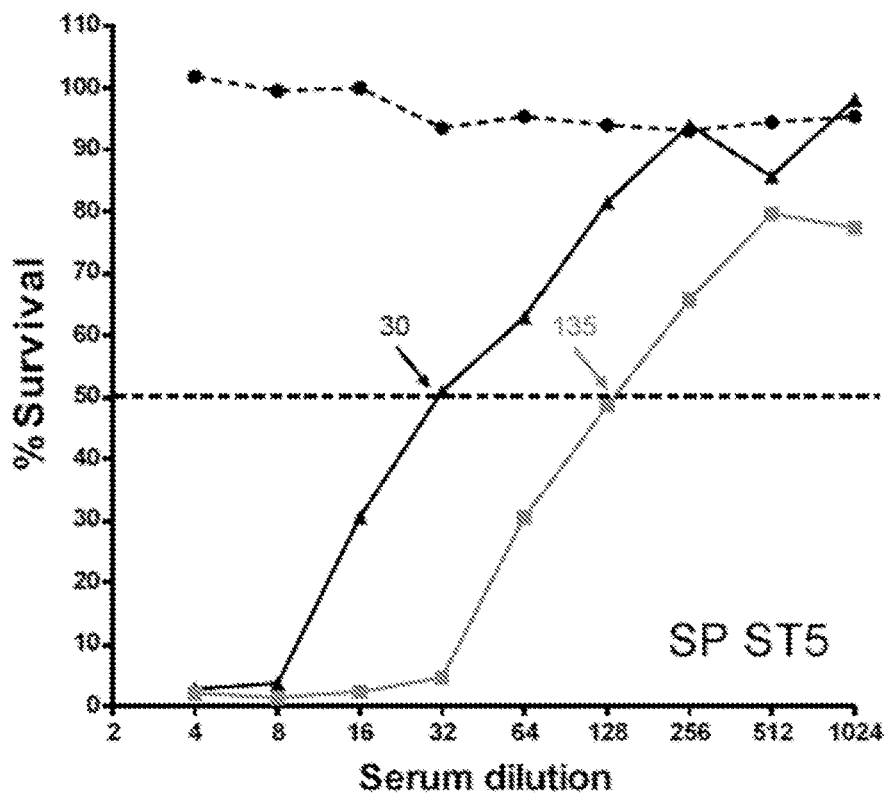
Figure 11D:
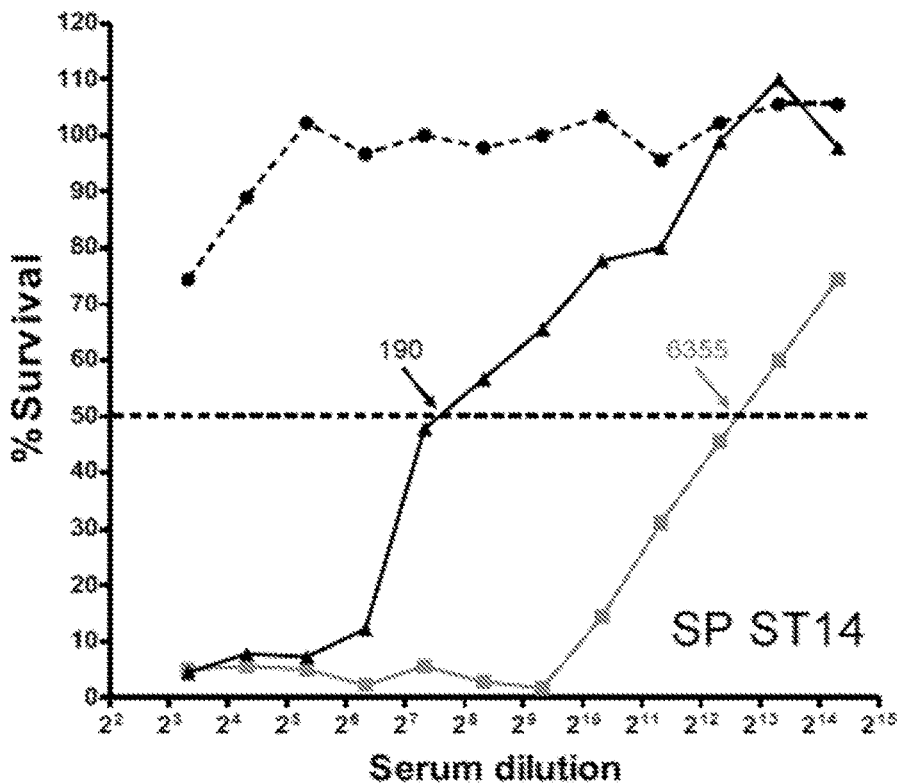
Figure 12A:
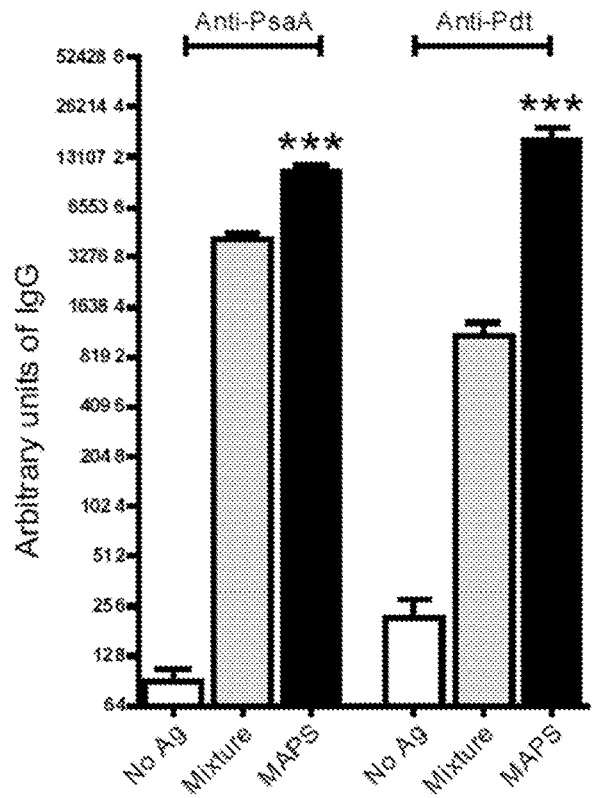
FIGS. 12A-12D demonstrate that immunization with a MAPS complex induces robust antibody and cellular response against protein antigens. Bivalent MAPS complex was made from biotinylated dextran (BD500) and two pneumococcal antigens, rhavi-Pdt and rhavi-PsaA. Subcutaneous vaccinations were given biweekly, three times.
Figure 12B:
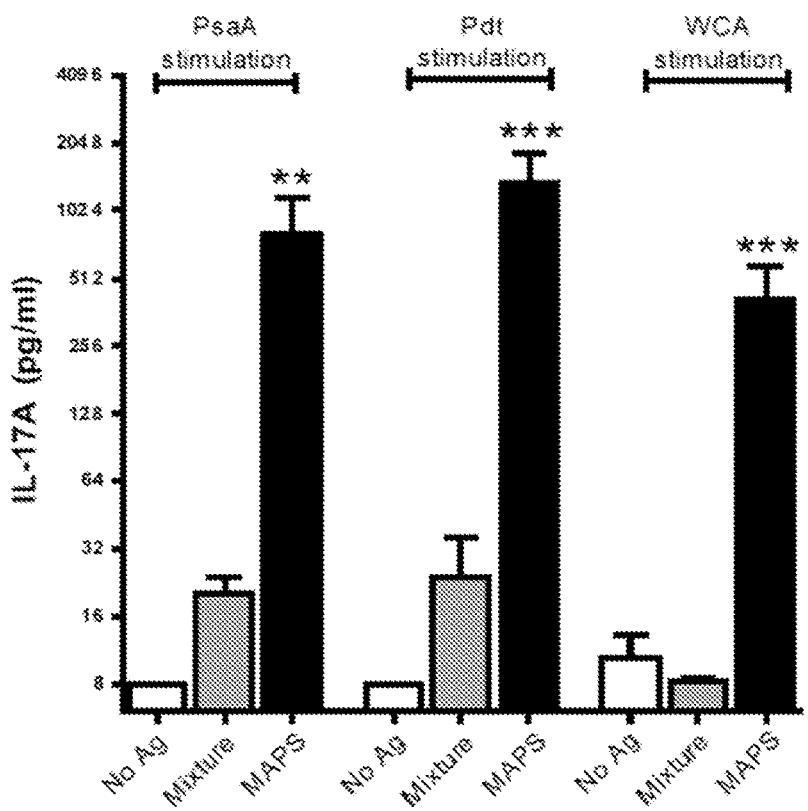
Figure 12C:
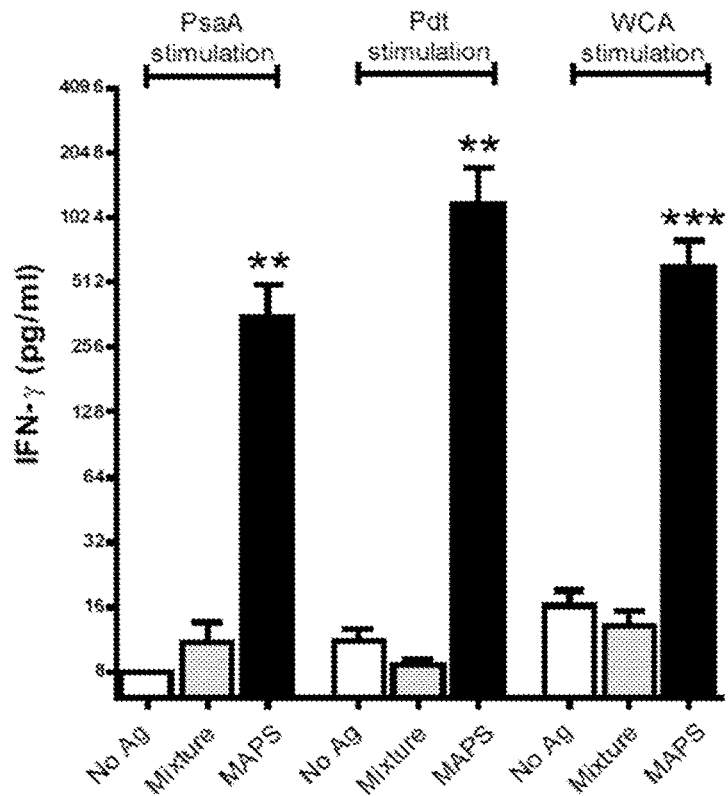
Figure 12D:
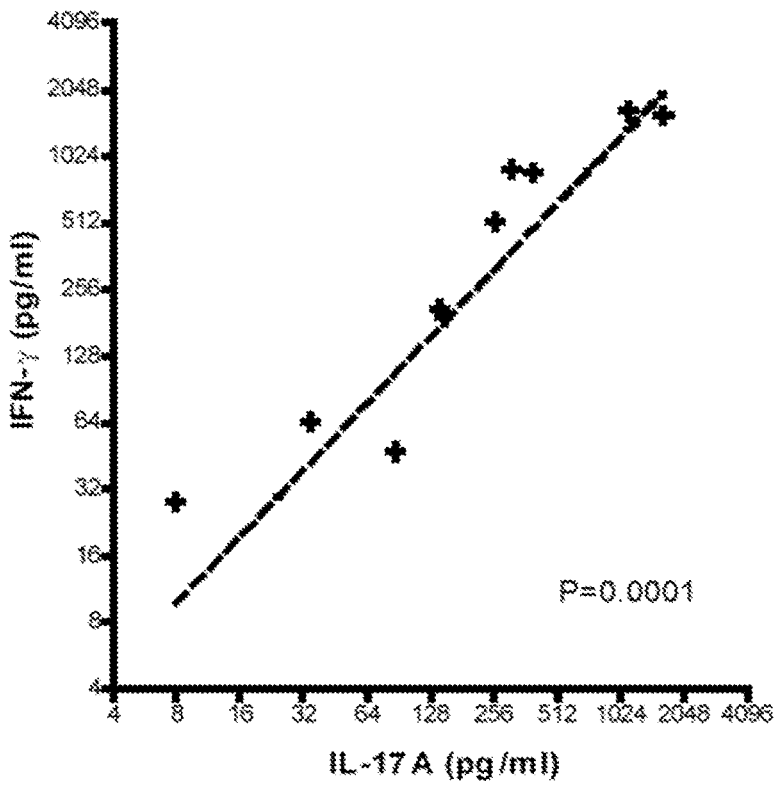
Figure 13C:
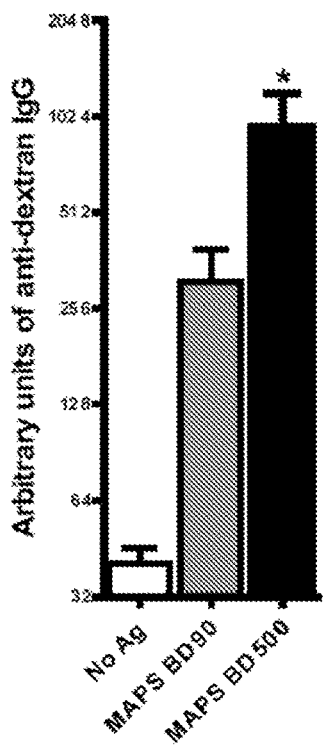
FIG. 13 shows the evaluation of the immunogenicity of MAPS complex in different sizes. MAPS complexes were made from two pneumococcal fusion antigens, rhavi-PsaA and rhavi-Pdt, and using dextran in different length as backbone (BD500, Mw of 425-500 kDa; BD90, Mw of 60-90 kDa). The antibody responses to dextran, and to two protein antigens PdT and PsaA, as well as the antigen specific T cell responses were measured and compared after 3 immunizations. As shown, mice that were immunized with the bigger complex (MAPS BD500) generated the similar level of anti-PsaA and anti-Pdt antibodies (FIG. 13B), but the significantly higher titer of anti-dextran antibody (FIG. 13A) as well as the IL-17A associated T cell response (FIG. 13C) than animals received the smaller complex (MAPS BD90).
Figure 13C:
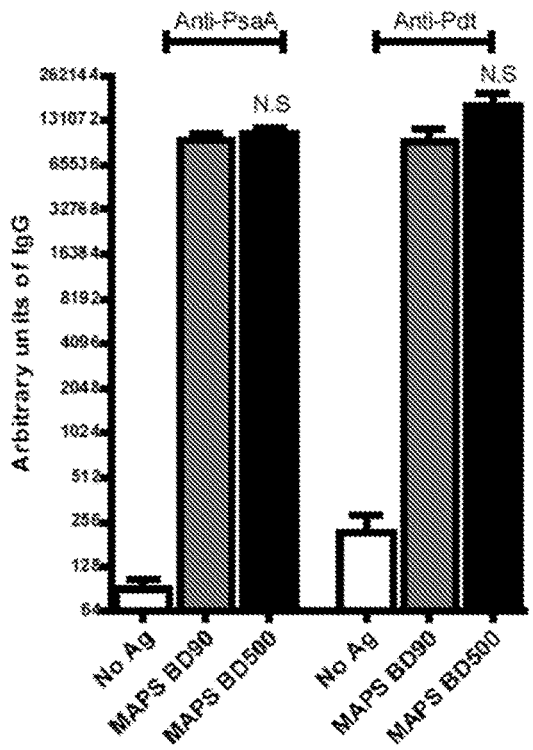
Figure 13C:
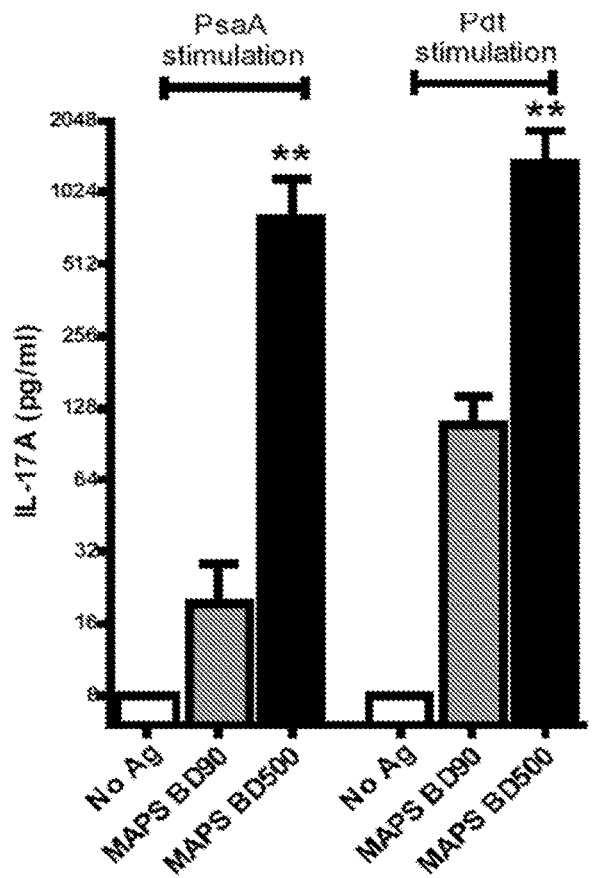
Figure 14A:
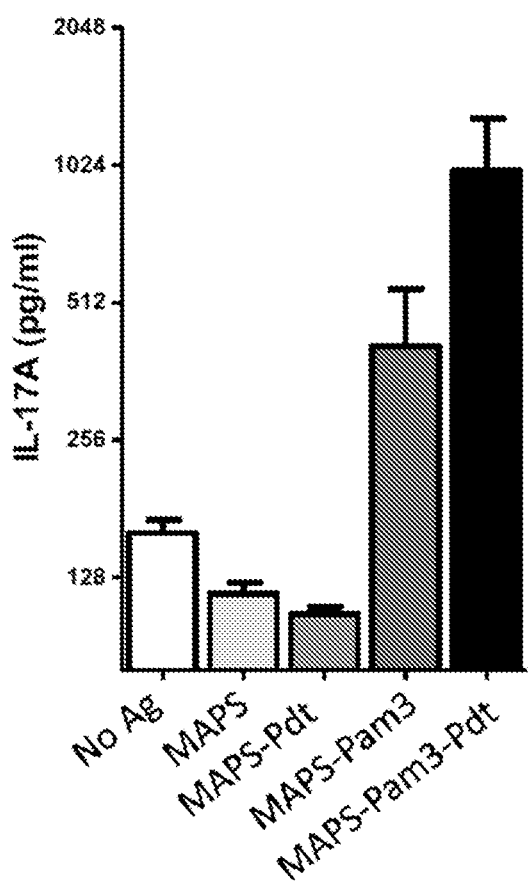
FIG. 14 shows that addition of co-stimulatory factors (TLR ligands) to the MAPS complex facilitates the IL-17A and IFN-γ associated T cell responses. MAPS complexes were made from biotinylated dextran and one pneumococcal protein antigen, rhavi-0435, with or without the additional TLR ligand/agonist: rhavi-Pdt, TLR4 ligand; Pam3CSK4, TLR2 agonist. The incorporation of rhavi-Pdt is via affinity interaction between rhavi and biotin, whereas Pam3CSK4 is covalently linked to the dextran backbone. Immunization was given subcutaneously for three times, and the T cell responses against 0435 protein were measured and compared. It showed that addition of TLR2 agonist or a combination of TLR4 and TLR2 ligands significantly enhanced the IL-17A and IFN-γ associated T cell responses to the protein antigen.
Figure 14B:
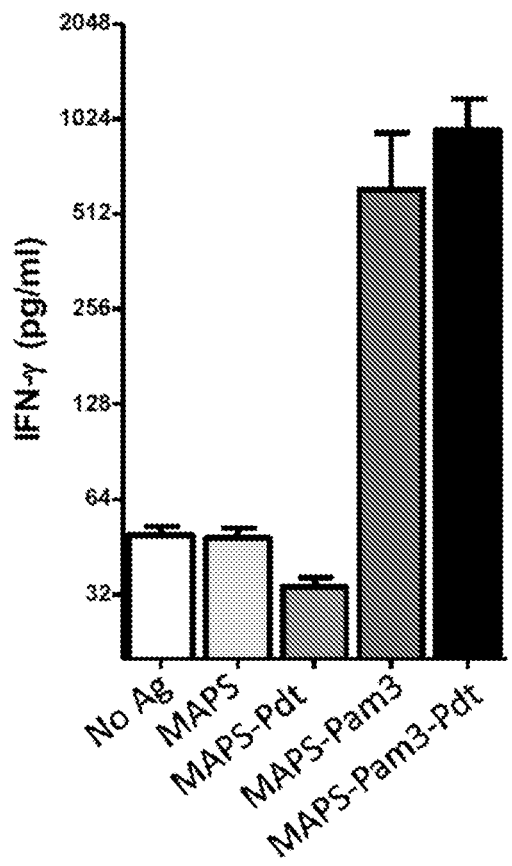
Figure 15A:
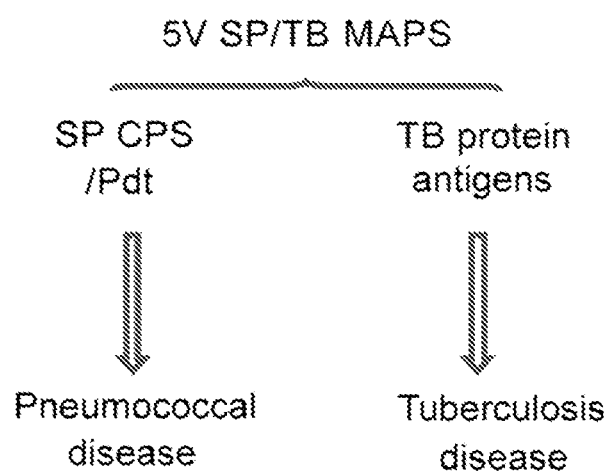
FIG. 15 shows an example of multivalent pneumococci/ *mycobacterium tuberculosis* (TB) combination vaccine. Multivalent SP/TB combination MAPS vaccine was prepared by using SP serotype 3 and loading one SP protein (pneumolysin toxoid, Pdt) and six TB proteins (in four fusion constructs) (FIG. 15A). Immunization of mice with SP/TB MAPS induced a great titer of IgG antibody to type 3 CPS (FIG. 15B, left panel), as well as to Pdt (FIG. 15B, right panel), and led to 100% protection of mice from fatal lung infection of serotype 3 pneumococcus (FIG. 15C).
FIGS. 15D-15J show the B-cell and T-cell immunity B antigens induced by vaccination with SP/TB MAPS.
Figure 15B:
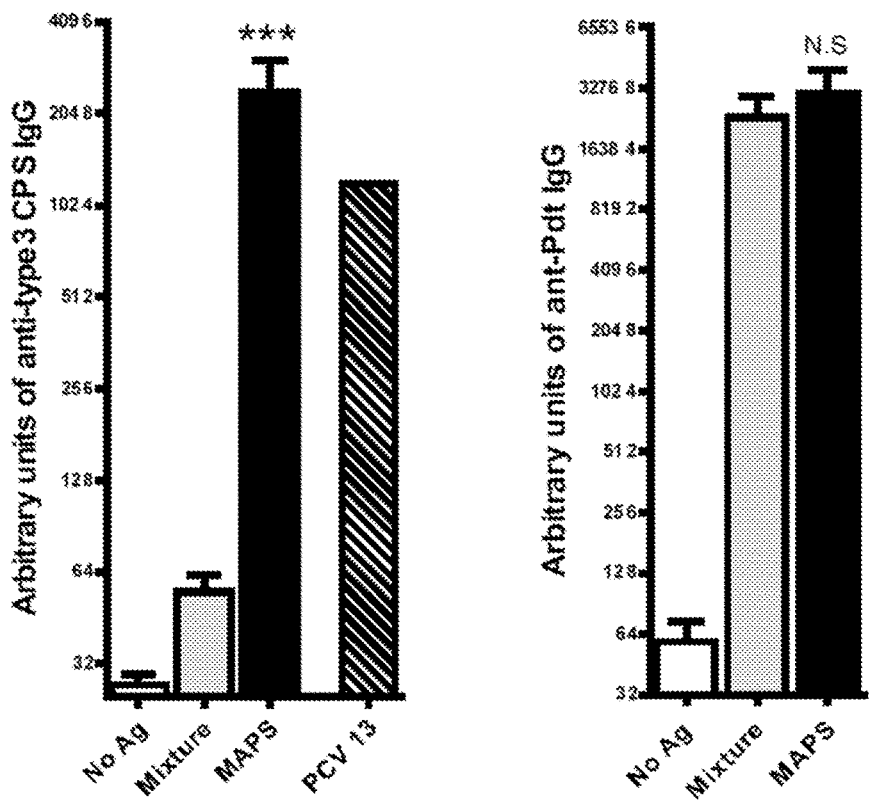
Figure 15C:
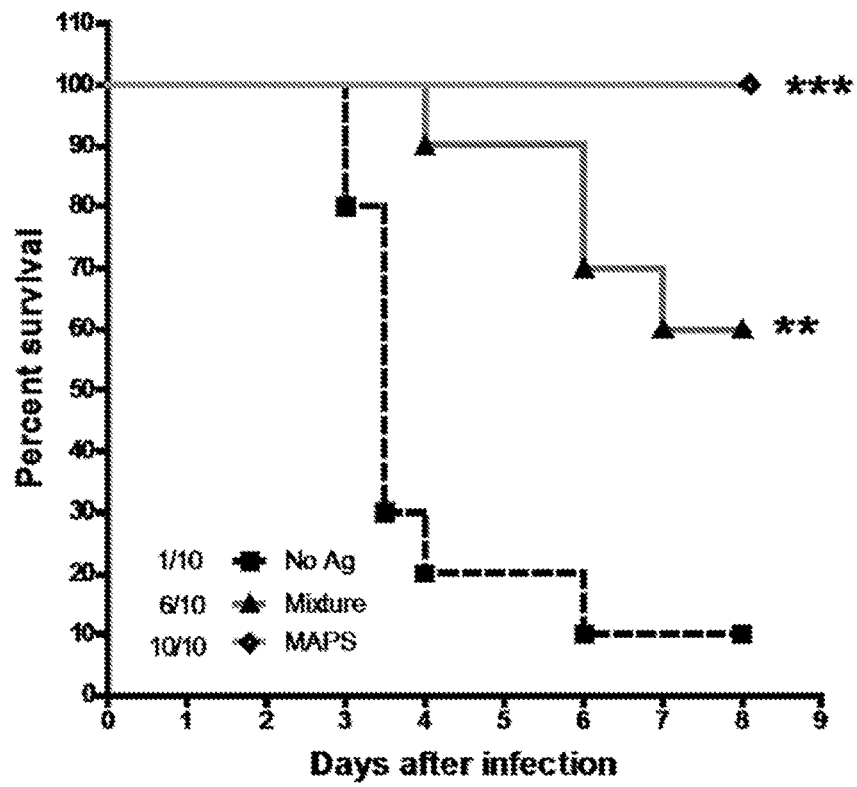
Figure 15D:
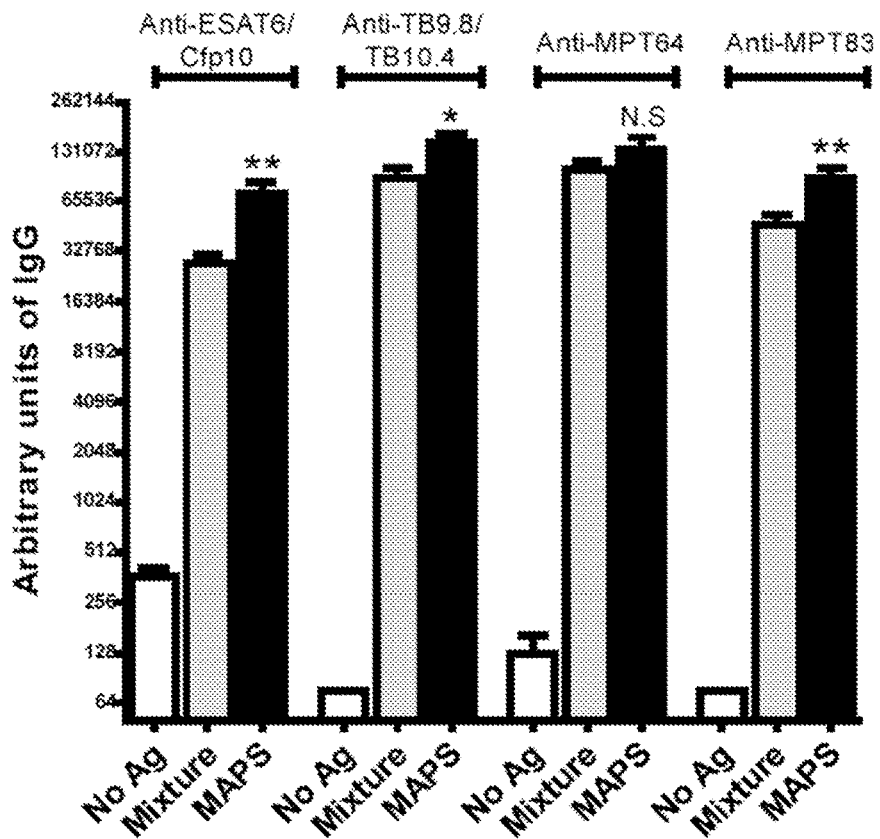
Figure 15E:
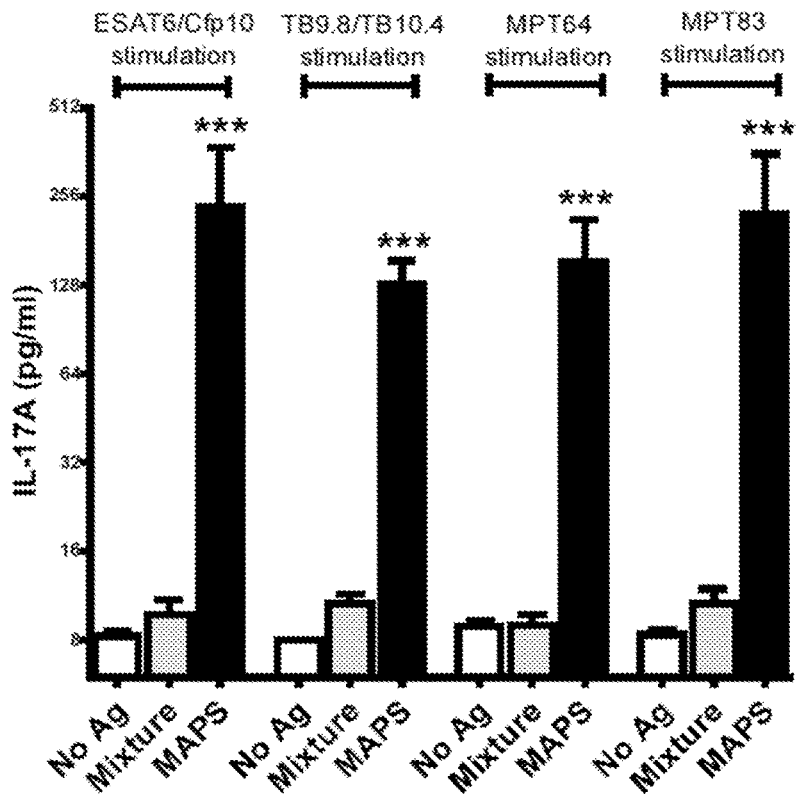
Figure 15I:
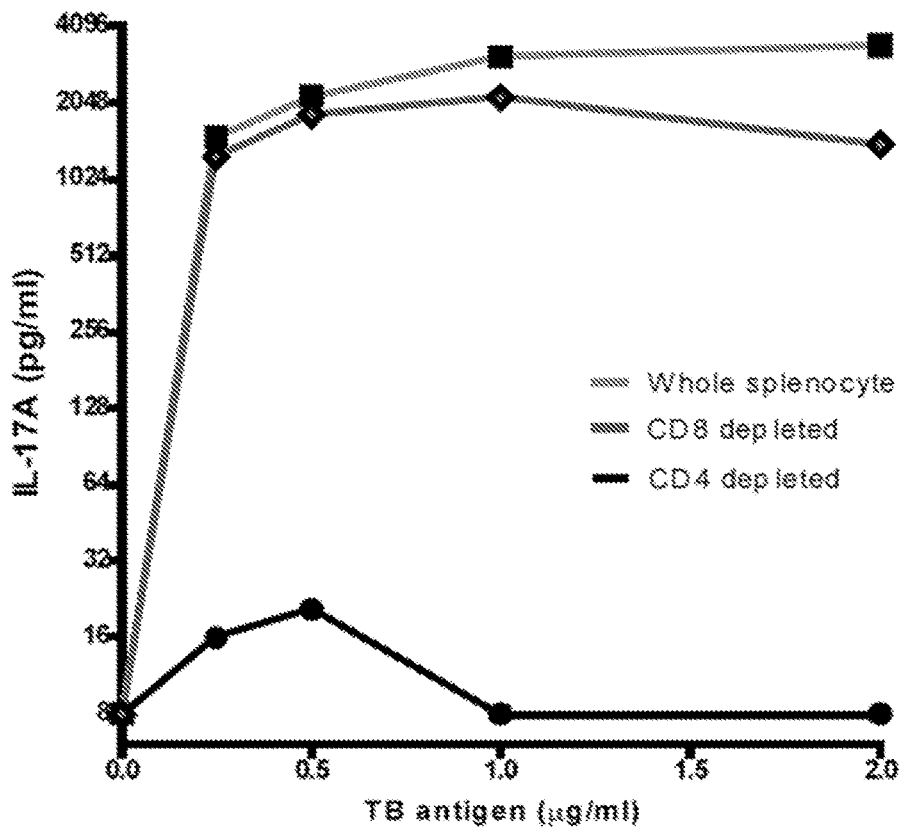
Figure 15J:
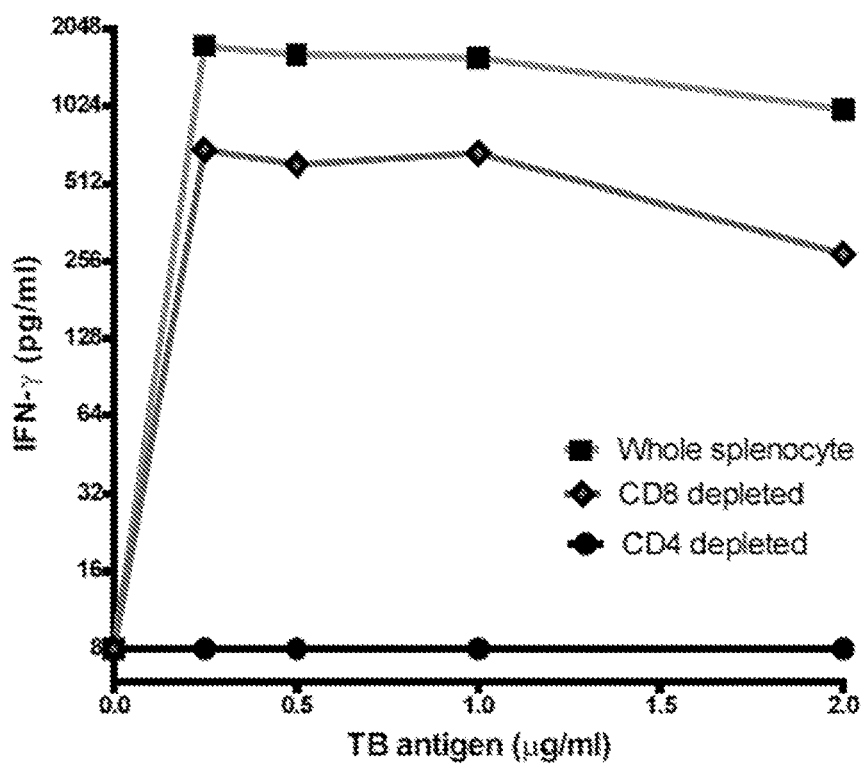
Figure 16A:
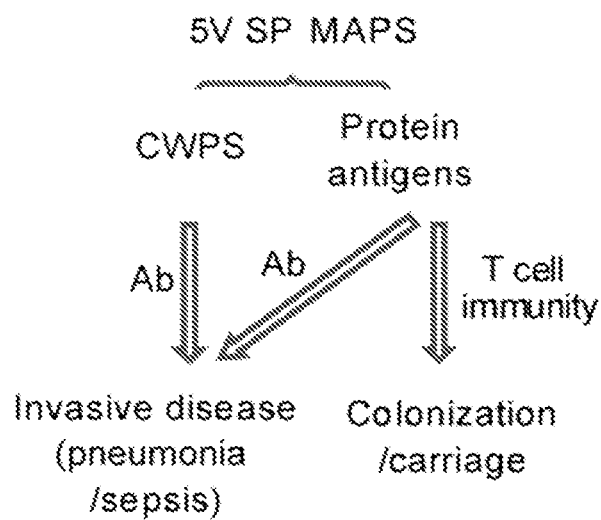
FIG. 16 demonstrates that a prototype MAPS-based multivalent immunogenic composition prevents invasive infection and nasopharyngeal colonization of pneumococcus. Multivalent SP MAPS was made using SP cell wall polysaccharide (CWPS) as the backbone and loaded with five pneumococcal protein antigens (FIG. 16A). Mice were immunized with this SP MAPS three times, two weeks apart, and the serum antibodies and specific T-cell responses against pneumococcus were analyzed two weeks after the last immunization.
FIG. 16B shows serum IgG antibody against CWPS (left panel) or against pneumococcal whole cell antigen (WCA) (right panel). Mice immunized with SP MAPS made significant higher titer of antibodies to either CWPS or WCA than mice in the control groups that received adjuvant alone (No Ag) or uncoupled PS/protein mixture (Mixture).
FIGS. 16C and 16D show SP-specific T-cell responses induced by vaccination with SP MAPS. Peripheral blood from mice of different immunization groups were stimulated with either purified pneumococcal proteins (antigen mix) or WCA. Cells from MAPS vaccinated mice but not from the control groups responded to the SP antigens greatly and gave robust production of IL-17A (FIG. 16C) and IFN-γ (FIG. 16D).
FIGS. 16E and 16F show that vaccination with MAPS complex protects mice from invasive infection as well as nasopharyngeal colonization of pneumococcus. Mice of different immunization groups were challenged either with SP serotype 3 strain WU2 in a lung aspiration model (FIG. 16E), or with serotype 6 pneumococcal strain 603 in a nasal colonization model (FIG. 16F). Protection against sepsis or colonization was only observed in MAPS-immunized mice.
Figure 16B:
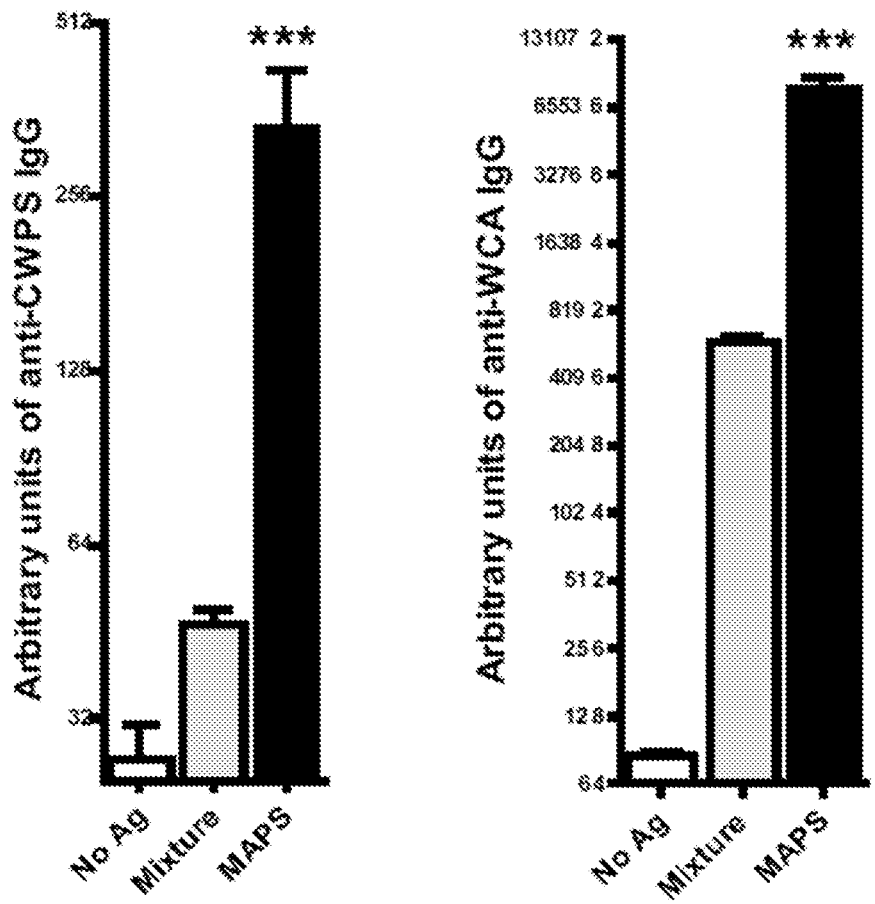
Figure 16C:
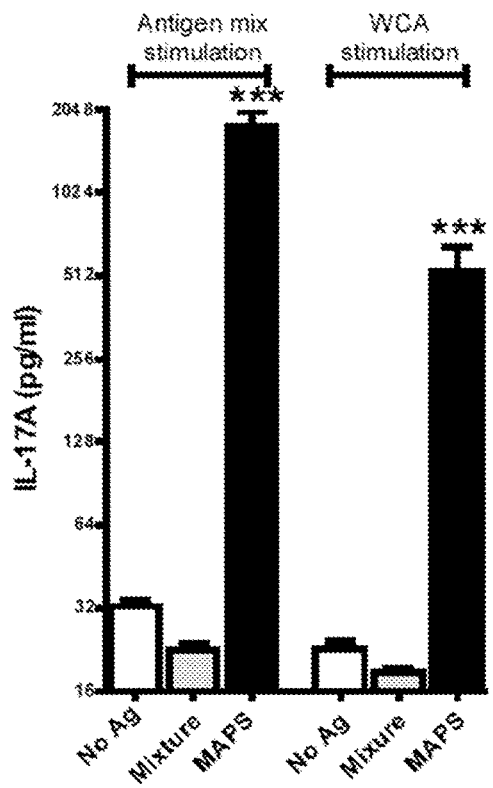
Figure 16D:
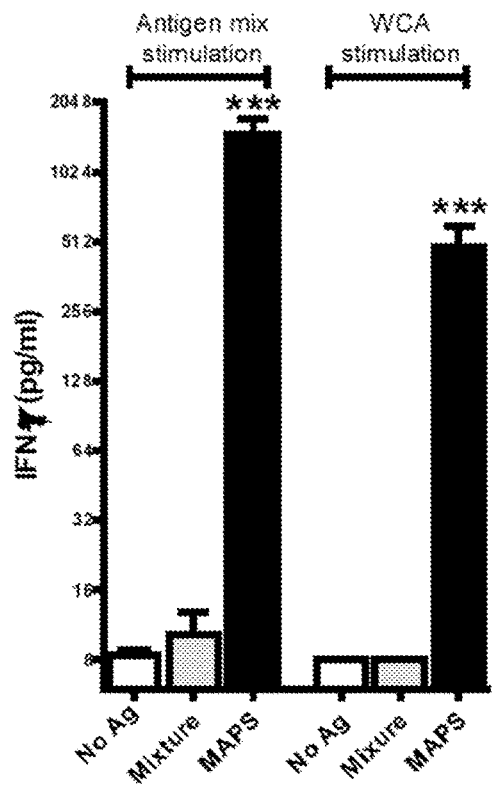
Figure 16E:
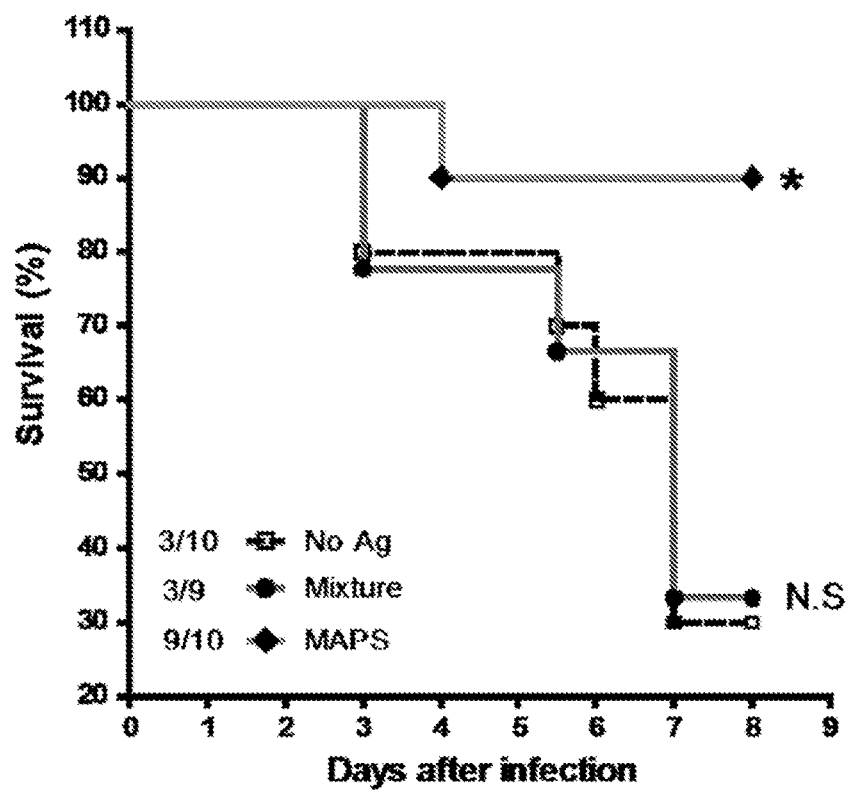
Figure 16F:
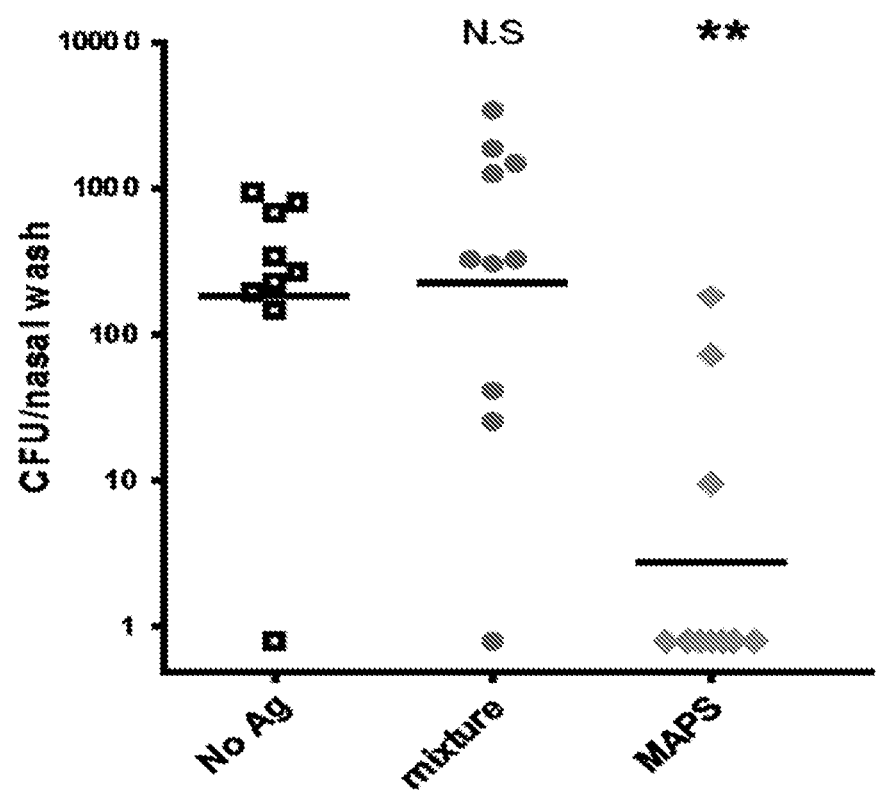

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. The term "or" is inclusive unless modified, for example, by "either." Other than in the operating examples, or where otherwise indicated, all numbers expressing quantities of ingredients or reaction conditions used herein should be understood as modified in all instances by the term "about." It is further to be understood that all base sizes or amino acid sizes, and all molecular weight or molecular mass values, given for nucleic acids or polypeptides are approximate, and are provided for description.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

The present invention relates immunogenic compositions and compositions comprising an immunogenic complex that comprises at least one antigen, or multiple antigens, attached to a polymer scaffold for use in eliciting an immune response to each of the antigens attached to the polymer, and optionally to the polymer itself, when administered to a subject. This multiple antigen presenting system (MAPS), stimulates a humoral and cellular immune response: it can generate anti-polysaccharide antibody and the B-cell/Th1/Th17 responses to multiple protein antigens using single MAPS immunogenic construct. A combination of B- and T-cell immunity to the organism might represent an optimal vaccine strategy against many diseases, including pneumococcal disease associated invasive infection and nasopharyngeal carriage. In some embodiments, the immunogenic composition is a vaccine or is included in a vaccine.

Accordingly, one aspect of the present invention relates to an immunogenic composition (multiple antigen presenting system, or MAPS) comprising at least one polymer, e.g., one polysaccharide, at least one protein or peptide antigen, and at least one complementary affinity-molecule pair comprising (i) a first affinity molecule associated with the polymer, and (ii) a complementary affinity molecule associated with the antigen, which serves to indirectly attach the antigen to the polymer (e.g., the first affinity molecule associates with the complementary affinity molecule to link the antigen to the polymer). Accordingly, as the polymer can be used as a scaffold to attach at least 1, or at least 2, or a more (e.g., a plurality) of the same or different antigens. The immunogenic compositions as disclosed herein can be used to elicit both humoral and cellular immunity to multiple antigens at the same time.

Accordingly, the embodiments herein provide for an immunogenic composition and methods useful for raising an immune response in a subject, which can be used on its own or in conjunction or admixture with essentially any existing vaccine approaches.

DEFINITIONS

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

The term "immunogenic composition" used herein is defined as a composition capable of eliciting an immune response, such as an antibody or cellular immune response, when administered to a subject. The immunogenic compositions of the present invention may or may not be immunoprotective or therapeutic. When the immunogenic compositions of the present invention prevent, ameliorate, palliate or eliminate disease from the subject, then the immunogenic composition may optionally be referred to as a vaccine. As used herein, however, the term immunogenic composition is not intended to be limited to vaccines.

As used herein, the term "antigen" refers to any substance that prompts an immune response directed against the substance. In some embodiments, an antigen is a peptide or a polypeptide, and in other embodiments, it can be any chemical or moiety, e.g., a carbohydrate, that elicits an immune response directed against the substance.

The term "associates" as used herein refers to the linkage of two or more molecules by non-covalent or covalent bonds. In some embodiments, where linking of two or more molecules occurs by a covalent bond, the two or more molecules can be fused together, or cross-linked together. In some embodiments, where linking of two or more molecules occurs by a non-covalent bond, the two or more molecules can form a complex.

The term "complex" as used herein refers to a collection of two or more molecules, connected spatially by means other than a covalent interaction; for example they can be connected by electrostatic interactions, hydrogen bound or by hydrophobic interactions (i.e., van der Waals forces).

The term "cross-linked" as used herein refers to a covalent bond formed between a polymer chain and a second molecule. The term "cross-linking reagent" refers to an entity or agent which is an intermediate molecule to catalyze the covalent linkage of a polymer with an entity, e.g., first affinity molecule or co-stimulatory factor.

As used herein, the term "fused" means that at least one protein or peptide is physically associated with a second protein or peptide. In some embodiments, fusion is typically a covalent linkage, however, other types of linkages are encompassed in the term "fused" include, for example, linkage via an electrostatic interaction, or a hydrophobic interaction and the like. Covalent linkage can encompass linkage as a fusion protein or chemically coupled linkage, for example via a disulfide bound formed between two cysteine residues.

As used herein, the term "fusion polypeptide" or "fusion protein" means a protein created by joining two or more polypeptide sequences together. The fusion polypeptides encompassed in this invention include translation products of a chimeric gene construct that joins the DNA sequences encoding one or more antigens, or fragments or mutants thereof, with the DNA sequence encoding a second polypeptide to form a single open-reading frame. In other words, a "fusion polypeptide" or "fusion protein" is a recombinant protein of two or more proteins which are joined by a peptide bond or via several peptides. In some embodiments, the second protein to which the antigens are fused to is a complementary affinity molecule which is capable of interacting with a first affinity molecule of the complementary affinity pair.

The terms "polypeptide" and "protein" may be used interchangeably to refer to a polymer of amino acid residues linked by peptide bonds, and for the purposes of the claimed invention, have a typical minimum length of at least 25 amino acids. The term "polypeptide" and "protein" can encompass a multimeric protein, e.g., a protein containing more than one domain or subunit. The term "peptide" as used herein refers to a sequence of peptide bond-linked amino acids containing less than 25 amino acids, e.g., between about 4 amino acids and 25 amino acids in length. Proteins and peptides can be composed of linearly arranged amino acids linked by peptide bonds, whether produced biologically, recombinantly, or synthetically and whether composed of naturally occurring or non-naturally occurring amino acids, are included within this definition. Both full-length proteins and fragments thereof greater than 25 amino acids are encompassed by the definition of protein. The terms also include polypeptides that have co-translational (e.g., signal peptide cleavage) and post-translational modifications of the polypeptide, such as, for example, disulfide-bond formation, glycosylation, acetylation, phosphorylation, lipidation, proteolytic cleavage (e.g., cleavage by metalloproteases), and the like. Furthermore, as used herein, a "polypeptide" refers to a protein that includes modifications, such as deletions, additions, and substitutions (generally conservative in nature as would be known to a person in the art) to the native sequence, as long as the protein maintains the desired activity. These modifications can be deliberate, as through site-directed mutagenesis, or can be accidental, such as through mutations of hosts that produce the proteins, or errors due to PCR amplification or other recombinant DNA methods.

By "signal sequence" is meant a nucleic acid sequence which, when operably linked to a nucleic acid molecule, facilitates secretion of the product (e.g., protein or peptide) encoded by the nucleic acid molecule. In some embodiments, the signal sequence is preferably located 5' to the nucleic acid molecule.

As used herein, the term "N-glycosylated" or "N-glycosylation" refers to the covalent attachment of a sugar moiety to asparagine residues in a polypeptide. Sugar moieties can include but are not limited to glucose, mannose, and N-acetylglucosamine. Modifications of the glycans are also included, e.g., siaylation.

An "antigen presenting cell" or "APC" is a cell that expresses the Major Histocompatibility complex (MHC) molecules and can display foreign antigen complexed with MHC on its surface. Examples of antigen presenting cells are dendritic cells, macrophages, B-cells, fibroblasts (skin), thymic epithelial cells, thyroid epithelial cells, glial cells (brain), pancreatic beta cells, and vascular endothelial cells.

The term "functional portion" or "functional fragment" as used in the context of a "functional portion of an antigen" refers to a portion of the antigen or antigen polypeptide that mediates the same effect as the full antigen moiety, e.g., elicits an immune response in a subject, or mediates an association with other molecule, e.g., comprises at least on epitope.

A "portion" of a target antigen as that term is used herein will be at least 3 amino acids in length, and can be, for example, at least 6, at least 8, at least 10, at least 14, at least 16, at least 17, at least 18, at least 19, at least 20 or at least 25 amino acids or greater, inclusive.

The terms "Cytotoxic T Lymphocyte" or "CTL" refers to lymphocytes which induce death via apoptosis or other mechanisms in targeted cells. CTLs form antigen-specific conjugates with target cells via interaction of TCRs with processed antigen (Ag) on target cell surfaces, resulting in apoptosis of the targeted cell. Apoptotic bodies are eliminated by macrophages. The term "CTL response" is used to refer to the primary immune response mediated by CTL cells.

The term "cell mediated immunity" or "CMI" as used herein refers to an immune response that does not involve antibodies or complement but rather involves the activation of, for example, macrophages, natural killer cells (NK), antigen-specific cytotoxic T-lymphocytes (T-cells), T-helper cells, neutrophils, and the release of various cytokines in response to a target antigen. Stated another way, CMI refers to immune cells (such as T cells and other lymphocytes) which bind to the surface of other cells that display a target antigen (such as antigen presenting cells (APC)) and trigger a response. The response may involve either other lymphocytes and/or any of the other white blood cells (leukocytes) and the release of cytokines. Cellular immunity protects the body by: (i) activating antigen-specific cytotoxic T-lymphocytes (CTLs) that are able to destroy body cells displaying epitopes of foreign antigen on their surface, such as virus-infected cells and cells with intracellular bacteria; (2) activating macrophages and NK cells, enabling them to destroy intracellular pathogens; and (3) stimulating cells to secrete a variety of cytokines or chemokines that influence the function of other cells such as T cells, macrophages or neutrophils involved in adaptive immune responses and innate immune responses.

The term "immune cell" as used herein refers to any cell which can release a cytokine, chemokine or antibody in response to a direct or indirect antigenic stimulation. Included in the term "immune cells" herein are lymphocytes, including natural killer (NK) cells, T-cells (CD4+ and/or CD8+ cells), B-cells, macrophages; leukocytes; dendritic cells; mast cells; monocytes; and any other cell which is capable of producing a cytokine or chemokine molecule in response to direct or indirect antigen stimulation. Typically, an immune cell is a lymphocyte, for example a T-cell lymphocyte.

The term "cytokine" as used herein refers to a molecule released from an immune cell in response to stimulation with an antigen. Examples of such cytokines include, but are not limited to: GM-CSF; IL-1α; IL-1β; IL-2; IL-3; IL-4; IL-5; IL-6; IL-7; IL-8; IL-10; IL-12; IL-17A, IL-17F or other members of the IL-17 family, IL-22, IL-23, IFN-α; IFN-β; IFN-γ; MIP-1α; MIP-1β; TGF-β; TNFα, or TNFβ. The term "cytokine" does not include antibodies The term "subject" as used herein refers to any animal in which it is useful to elicit an immune response. The subject can be a wild, domestic, commercial or companion animal such as a bird or mammal. The subject can be a human. Although in one embodiment of the invention it is contemplated that the immunogenic compositions as disclosed herein can also be suitable for the therapeutic or preventative treatment in humans, it is also applicable to warm-blooded vertebrates, e.g., mammals, such as non-human primates, (particularly higher primates), sheep, dog, rodent (e.g., mouse or rat), guinea pig, goat, pig, cat, rabbits, cows, and non-mammals such as chickens, ducks, or turkeys. In another embodiment, the subject is a wild animal, for example a bird such as for the diagnosis of avian flu. In some embodiments, the subject is an experimental animal or animal substitute as a disease model. The subject may be a subject in need of veterinary treatment, where eliciting an immune response to an antigen is useful to prevent a disease and/or to control the spread of a disease, for example SIV, STL1, SFV, or in the case of live-stock, hoof and mouth disease, or in the case of birds Marek's disease or avian influenza, and other such diseases.

As used herein, the term "pathogen" refers to an organism or molecule that causes a disease or disorder in a subject. For example, pathogens include but are not limited to viruses, fungi, bacteria, parasites, and other infectious organisms or molecules therefrom, as well as taxonomically related macroscopic organisms within the categories algae, fungi, yeast, protozoa, or the like.

A "cancer cell" refers to a cancerous, pre-cancerous, or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage independence, malignancy, loss of contact inhibition and density limitation of growth, growth factor or serum independence, tumor specific markers, invasiveness or metastasis, and tumor growth in suitable animal hosts such as nude mice. See, e.g., Freshney, CULTURE ANIMAL CELLS: MANUAL BASIC TECH. (3rd ed., 1994).

The term "wild type" refers to the naturally-occurring, normal polynucleotide sequence encoding a protein, or a portion thereof, or protein sequence, or portion thereof, respectively, as it normally exists in vivo.

The term "mutant" refers to an organism or cell with any change in its genetic material, in particular a change (i.e., deletion, substitution, addition, or alteration) relative to a wild-type polynucleotide sequence or any change relative to a wild-type protein sequence. The term "variant" may be used interchangeably with "mutant". Although it is often assumed that a change in the genetic material results in a change of the function of the protein, the terms "mutant" and "variant" refer to a change in the sequence of a wild-type protein regardless of whether that change alters the function of the protein (e.g., increases, decreases, imparts a new function), or whether that change has no effect on the function of the protein (e.g., the mutation or variation is silent).

The term "pharmaceutically acceptable" refers to compounds and compositions which may be administered to mammals without undue toxicity. The term "pharmaceutically acceptable carriers" excludes tissue culture medium. Exemplary pharmaceutically acceptable salts include but are not limited to mineral acid salts such as hydrochlorides, hydrobromides, phosphates, sulfates, and the like, and the salts of organic acids such as acetates, propionates, malonates, benzoates, and the like. Pharmaceutically acceptable carriers are well-known in the art.

It will be appreciated that proteins or polypeptides often contain amino acids other than the 20 amino acids commonly referred to as the 20 naturally occurring amino acids, and that many amino acids, including the terminal amino acids, can be modified in a given polypeptide, either by natural processes such as glycosylation and other post-translational modifications, or by chemical modification techniques which are well known in the art. Known modifications which can be present in polypeptides of the present invention include, but are not limited to, acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formulation, gamma-carboxylation, glycation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

As used herein, the terms "homologous" or "homologues" are used interchangeably, and when used to describe a polynucleotide or polypeptide, indicate that two polynucleotides or polypeptides, or designated sequences thereof, when optimally aligned and compared, for example using BLAST, version 2.2.14 with default parameters for an alignment are identical, with appropriate nucleotide insertions or deletions or amino-acid insertions or deletions, typically in at least 70% of the nucleotides of the nucleotides for high homology. For a polypeptide, there should be at least 30% of amino acid identity in the polypeptide, or at least 50% for higher homology. The term "homolog" or "homologous" as used herein also refers to homology with respect to structure. Determination of homologs of genes or polypeptides can be easily ascertained by the skilled artisan. When in the context with a defined percentage, the defined percentage homology means at least that percentage of amino acid similarity. For example, 85% homology refers to at least 85% of amino acid similarity.

As used herein, the term "heterologous" reference to nucleic acid sequences, proteins or polypeptides mean that these molecules are not naturally occurring in that cell. For example, the nucleic acid sequence coding for a fusion antigen polypeptide described herein that is inserted into a cell, e.g. in the context of a protein expression vector, is a heterologous nucleic acid sequence.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Where necessary or desired, optimal alignment of sequences for comparison can be conducted by any variety of approaches, as these are well-known in the art.

The term "variant" as used herein may refer to a polypeptide or nucleic acid that differs from the naturally occurring polypeptide or nucleic acid by one or more amino acid or nucleic acid deletions, additions, substitutions or side-chain modifications, yet retains one or more specific functions or biological activities of the naturally occurring molecule. Amino acid substitutions include alterations in which an amino acid is replaced with a different naturally-occurring or a non-conventional amino acid residue. Such substitutions may be classified as "conservative," in which case an amino acid residue contained in a polypeptide is replaced with another naturally occurring amino acid of similar character either in relation to polarity, side chain functionality or size. Substitutions encompassed by variants as described herein may also be "non conservative," in which an amino acid residue which is present in a peptide is substituted with an amino acid having different properties (e.g., substituting a charged or hydrophobic amino acid with alanine), or alternatively, in which a naturally-occurring amino acid is substituted with a non-conventional amino acid. Also encompassed within the term "variant," when used with reference to a polynucleotide or polypeptide, are variations in primary, secondary, or tertiary structure, as compared to a reference polynucleotide or polypeptide, respectively (e.g., as compared to a wild-type polynucleotide or polypeptide).

The term "substantially similar," when used in reference to a variant of an antigen or a functional derivative of an antigen as compared to the original antigen means that a particular subject sequence varies from the sequence of the antigen polypeptide by one or more substitutions, deletions, or additions, but retains at least 50%, or higher, e.g., at least 60%, 70%, 80%, 90% or more, inclusive, of the function of the antigen to elicit an immune response in a subject. In determining polynucleotide sequences, all subject polynucleotide sequences capable of encoding substantially similar amino acid sequences are considered to be substantially similar to a reference polynucleotide sequence, regardless of differences in codon sequence. A nucleotide sequence is "substantially similar" to a given antigen nucleic acid sequence if: (a) the nucleotide sequence hybridizes to the coding regions of the native antigen sequence, or (b) the nucleotide sequence is capable of hybridization to nucleotide sequence of the native antigen under moderately stringent conditions and has biological activity similar to the native antigen protein; or (c) the nucleotide sequences are degenerate as a result of the genetic code relative to the nucleotide sequences defined in (a) or (b). Substantially similar proteins will typically be greater than about 80% similar to the corresponding sequence of the native protein.

Variants can include conservative or non-conservative amino acid changes, as described below. Polynucleotide changes can result in amino acid substitutions, additions, deletions, fusions and truncations in the polypeptide encoded by the reference sequence. Variants can also include insertions, deletions or substitutions of amino acids, including insertions and substitutions of amino acids and other molecules) that do not normally occur in the peptide sequence that is the basis of the variant, for example but not limited to insertion of ornithine which do not normally occur in human proteins. "Conservative amino acid substitutions" result from replacing one amino acid with another that has similar structural and/or chemical properties. Conservative substitution tables providing functionally similar amino acids are well known in the art. For example, the following six groups each contain amino acids that are conservative substitutions for one another: (1) Alanine (A), Serine (S), Threonine (T); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); and (6) Phenylalanine (F), Tyrosine (Y), Tryptophan (W). See, e.g., Creighton, PROTEINS (W.H. Freeman & Co., 1984).

The choice of conservative amino acids may be selected based on the location of the amino acid to be substituted in the peptide, for example if the amino acid is on the exterior of the peptide and exposed to solvents, or on the interior and not exposed to solvents. Selection of such conservative amino acid substitutions is within the skill of one of ordinary skill in the art. Accordingly, one can select conservative amino acid substitutions suitable for amino acids on the exterior of a protein or peptide (i.e. amino acids exposed to a solvent). These substitutions include, but are not limited to the following: substitution of Y with F, T with S or K, P with A, E with D or Q, N with D or G, R with K, G with N or A, T with S or K, D with N or E, I with L or V, F with Y, S with T or A, R with K, G with N or A, K with R, A with S, K or P.

Alternatively, one can also select conservative amino acid substitutions suitable for amino acids on the interior of a protein or peptide (i.e., the amino acids are not exposed to a solvent). For example, one can use the following conservative substitutions: where Y is substituted with F, T with A or S, I with L or V, W with Y, M with L, N with D, G with A, T with A or S, D with N, I with L or V, F with Y or L, S with A or T and A with S, G, T or V. In some embodiments, LF polypeptides including non-conservative amino acid substitutions are also encompassed within the term "variants." As used herein, the term "non-conservative" substitution refers to substituting an amino acid residue for a different amino acid residue that has different chemical properties. Non-limiting examples of non-conservative substitutions include aspartic acid (D) being replaced with glycine (G); asparagine (N) being replaced with lysine (K); and alanine (A) being replaced with arginine (R).

The term "derivative" as used herein refers to proteins or peptides which have been chemically modified, for example by ubiquitination, labeling, pegylation (derivatization with polyethylene glycol) or addition of other molecules. A molecule is also a "derivative" of another molecule when it contains additional chemical moieties not normally a part of the molecule. Such moieties can improve the molecule's solubility, absorption, biological half-life, etc. The moieties can alternatively decrease the toxicity of the molecule, or eliminate or attenuate an undesirable side effect of the molecule, etc. Moieties capable of mediating such effects are disclosed in Remington's Pharmaceutical Sciences (21st ed., Tory, ed., Lippincott Williams & Wilkins, Baltimore, Md., 2006).

The term "functional" when used in conjunction with "derivative" or "variant" refers to a protein molecule which possesses a biological activity that is substantially similar to a biological activity of the entity or molecule of which it is a derivative or variant. "Substantially similar" in this context means that the biological activity, e.g., antigenicity of a polypeptide, is at least 50% as active as a reference, e.g., a corresponding wild-type polypeptide, e.g., at least 60% as active, 70% as active, 80% as active, 90% as active, 95% as active, 100% as active or even higher (i.e., the variant or derivative has greater activity than the wild-type), e.g., 110% as active, 120% as active, or more, inclusive.

The term "recombinant" when used to describe a nucleic acid molecule, means a polynucleotide of genomic, cDNA, viral, semisynthetic, and/or synthetic origin, which, by virtue of its origin or manipulation, is not associated with all or a portion of the polynucleotide sequences with which it is associated in nature. The term recombinant as used with respect to a peptide, polypeptide, protein, or recombinant fusion protein, means a polypeptide produced by expression from a recombinant polynucleotide. The term recombinant as used with respect to a host cell means a host cell into which a recombinant polynucleotide has been introduced. Recombinant is also used herein to refer to, with reference to material (e.g., a cell, a nucleic acid, a protein, or a vector) that the material has been modified by the introduction of a heterologous material (e.g., a cell, a nucleic acid, a protein, or a vector).

The term "vectors" refers to a nucleic acid molecule capable of transporting or mediating expression of a heterologous nucleic acid to which it has been linked to a host cell; a plasmid is a species of the genus encompassed by the term "vector." The term "vector" typically refers to a nucleic acid sequence containing an origin of replication and other entities necessary for replication and/or maintenance in a host cell. Vectors capable of directing the expression of genes and/or nucleic acid sequence to which they are operatively linked are referred to herein as "expression vectors". In general, expression vectors of utility are often in the form of "plasmids" which refer to circular double stranded DNA molecules which, in their vector form are not bound to the chromosome, and typically comprise entities for stable or transient expression or the encoded DNA. Other expression vectors that can be used in the methods as disclosed herein include, but are not limited to plasmids, episomes, bacterial artificial chromosomes, yeast artificial chromosomes, bacteriophages or viral vectors, and such vectors can integrate into the host's genome or replicate autonomously in the particular cell. A vector can be a DNA or RNA vector. Other forms of expression vectors known by those skilled in the art which serve the equivalent functions can also be used, for example self replicating extrachromosomal vectors or vectors which integrates into a host genome. Preferred vectors are those capable of autonomous replication and/or expression of nucleic acids to which they are linked.

The term "reduced" or "reduce" or "decrease" as used herein generally means a decrease by a statistically significant amount relative to a reference. For avoidance of doubt, "reduced" means statistically significant decrease of at least 10% as compared to a reference level, for example a decrease by at least 20%, at least 30%, at least 40%, at least t 50%, or least 60%, or least 70%, or least 80%, at least 90% or more, up to and including a 100% decrease (i.e., absent level as compared to a reference sample), or any decrease between 10-100% as compared to a reference level, as that term is defined herein.

The term "low" as used herein generally means lower by a statically significant amount; for the avoidance of doubt, "low" means a statistically significant value at least 10% lower than a reference level, for example a value at least 20% lower than a reference level, at least 30% lower than a reference level, at least 40% lower than a reference level, at least 50% lower than a reference level, at least 60% lower than a reference level, at least 70% lower than a reference level, at least 80% lower than a reference level, at least 90% lower than a reference level, up to and including 100% lower than a reference level (i.e., absent level as compared to a reference sample).

The terms "increased" or "increase" as used herein generally mean an increase by a statically significant amount; such as a statistically significant increase of at least 10% as compared to a reference level, including an increase of at least 20%, at least 30%, at least 40%, at least 50%, at least 60%, at least 70%, at least 80%, at least 90%, at least 100% or more, inclusive, including, for example at least 2-fold, at least 3-fold, at least 4-fold, at least 5-fold, at least 10-fold increase or greater as compared to a reference level, as that term is defined herein.

The term "high" as used herein generally means a higher by a statically significant amount relative to a reference; such as a statistically significant value at least 10% higher than a reference level, for example at least 20% higher, at least 30% higher, at least 40% higher, at least 50% higher, at least 60% higher, at least 70% higher, at least 80% higher, at least 90% higher, at least 100% higher, inclusive, such as at least 2-fold higher, at least 3-fold higher, at least 4-fold higher, at least 5-fold higher, at least 10-fold higher or more, as compared to a reference level.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment of the invention.

The present invention provides for a flexible and versatile composition that can be designed and manufactured to elicit a particular, broad spectrum, or variety of antigenic targets. Table 1 provides a simple example guide for envisioning the flexibility of MAPS embodiments:

Polymers

One component of MAP consists of a "backbone," typically a polymer. The polymer may be antigenic or non-antigenic. It can be made of a wide variety on substances, as described herein, with the caveat that the polymer serves as a means of presenting the associated antigen(s) to the immune system in immunogenic fashion. In some embodiments, the polymer is a synthetic polymer. In some embodiments, the polymer is a naturally occurring polymer, e.g., a polysaccharide derived or purified from bacterial cells. In some embodiments, the polysaccharide is derived or purified from eukaryotic cells, e.g., fungi, insect or plant cells. In yet other embodiments, the polymer is derived from mammalian cells, such as virus-infected cells or cancer cells. In general, such polymers are well known in the art and are encompassed for use in the methods and compositions as disclosed herein.

In some embodiments, a polymer is a polysaccharide selected from any of the following, dextran, Vi polysaccharide of *Salmonella typhi*, pneumococcal capsular polysaccharide, pneumococcal cell wall polysaccharide (CWPS), meningococcal polysaccharide, *Haemophilus influenzae* type b polysaccharide, or any another polysaccharide of viral, prokaryotic, or eukaryotic origin.

In some embodiments, the polysaccharide consists of or comprises an antigenic sugar moiety. For example, in some embodiments, a polysaccharide for use in the methods and immunogenic compositions as disclosed herein is a Vi polysaccharide of *Salmonella typhi*. The Vi capsular polysaccharide has been developed against bacterial enteric infections, such as typhoid fever. Robbins et al., 150 J. Infect. Dis. 436 (1984); Levine et al., 7 Baillieres Clin. Gastroenterol. 501 (1993). Vi is a polymer of α-1→4-galacturonic acid with an N acetyl at position C-2 and variable O-acetylation at C-3. The virulence of *S. typhi* correlates with the expression of this molecule. Sharma et al., 101 PNAS 17492 (2004). The Vi polysaccharide vaccine of *S. typhi* has several advantages: Side effects are infrequent and mild, a single dose yields consistent immunogenicity and efficacy. Vi polysaccharide may be reliably standardized by physicochemical methods verified for other polysaccharide vaccines, Vi is stable at room temperature and it may be

TABLE 1

Versatility of the MAPS platform

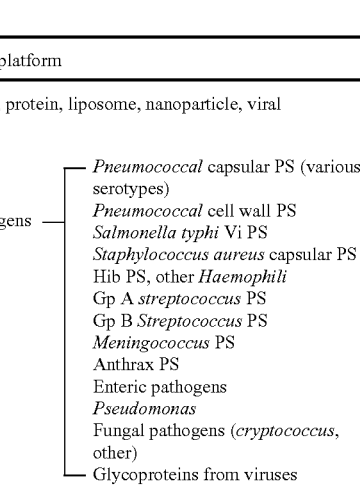

administered simultaneously with other vaccines without affecting immunogenicity and tolerability. Azze et al., 21 Vaccine 2758 (2003).

Thus, the Vi polysaccharide of *S. typhi* may be cross-linked to a first affinity molecule as disclosed herein, for attaching at least one antigen to the polysaccharide. In some embodiments, the antigen can be from the same or from another organism, such that the resulting immunogenic composition confers at least some level of immunity against one pathogen, or two different pathogens: if the antigen confers protection against pneumococcus, an immunogenic composition where the polymer scaffold is a Vi polysaccharide can raise an immunogenic response against both *S. typhi* and pneumococci. Other examples include combining sugars from encapsulated bacteria (such as meningococcus, *S. aureus*, pneumococcus, Hib, etc.) and tuberculosis antigens, to provide an immunogenic composition that raises an immune response against two different pathogens.

Other polysaccharide (PS) moieties that may be used in the present invention in alternative to dextran, bacterial cell wall polysaccharides (CWPS), etc., include carbohydrate antigens of cancers.

Further in regard to pneumococcal polysaccharides, the polysaccharide can be derived from any of the over 93 serotypes of pneumococcus that have been identified to date, for example, including but not limited to serotypes 1, 2, 3, 4, 5, 6A, 6B, 6C, 6D, 7F, 8, 9N, 9V, 10A, 11A, 12F, 14, 15B, 17F, 18C, 19A, 19F, 20, 22F, 23F, and 33F. Additional serotypes may be identified and included in the present immunogenic composition as described herein. More than one pneumococcal polysaccharide can be included as the polymer backbone of the present immunogenic compositions or in a vaccine comprising the present MAPS compositions.

The polysaccharide can also be derived from the invention, the immunogenic composition comprises *N. meningitidis* capsular polysaccharides from at least one, two, three or four of the serogroups A, C, W, W135, or Y.

A further embodiment comprises the Type 5, Type 8, or any of the polysaccharides or oligosaccharides of *Staphylococcus aureus*.

In some embodiments, the polymer is chimeric polymer comprising more than one type of polymer. For example a polymer of the immunogenic composition as disclosed herein can comprise a portion of polymer A, and the remaining portion of polymer B. There is no limit to the amount of different types of polymers which can be used in a single MAPS backbone entity. In some embodiments, where the polymer is a branched polymer, the chain polymer can be polymer A, and the branches can be at least 1 or at least 2 or at least 3 or more different polymers.

In some embodiments, the polymer is a branched polymer. In some embodiments, the polymer is a single chain polymer.

In some embodiments, the polymer is a polysaccharide comprising at least 10 carbohydrate repeating units, or at least 20, or at least 50, or at least 75, or at least 100, or at least 150, or at least 200, or at least 250, or at least 300, or at least 350, or at least 400, or at least 450, or at least 500, or more than 500 repeating units, inclusive.

In one aspect of the invention, the polysaccharide (PS) can have a molecular mass of <500 kDa or >500 kDa. In another aspect of the invention, the PS has a molecular mass of <70 kDa.

In some embodiments, a polymer is a large molecular weight polymer, e.g., a polymer can be of an average molecular weight of between about 425-500 kDa, inclusive, for example, at least 300 kDa, or at least 350 kDa, or at least 400 kDa, or at least 425 kDa, or at least 450 kDa, or at least 500 kDa or greater than 500 kDa, inclusive, but typically less than 500 kDa.

In some embodiments, a polymer can be a small molecular weight polymer, e.g., a polymer can be of an average molecular weight of between about 60kDA to about 90 kDa, for example, at least 50 kDa, or at least 60 kDa, or at least 70 kDa, or at least 80 kDa, or at least 90 kDa, or at least 100 kDa, or greater than 100 kDa, inclusive, but generally less than about 120 kDa.

In some embodiments, the polymer is harvested and purified from a natural source; and in other embodiments, the polymer is synthetic. Methods to produce synthetic polymers, including synthetic polysaccharides, are known to persons of ordinary skill and are encompassed in the compositions and methods as disclosed herein.

Just a few of the polysaccharide polymers that can serve as a backbone for one or more antigens or antigen types are exemplified in Table 2:

TABLE 2

Example polysaccharide polymer MAPS backbone and associated example antigens

| Polysaccharide | | Protein Antigens | |
| --- | --- | --- | --- |
| | | Number of antigens | Antigen origins |
| Dextran | D90 (60-90 KD) | two | pneumococcus |
| | D150 (150 KD) | three | pneumococcus |
| | D270 (270 KD) | three | pneumococcus |
| | D500 (425-575 KD) | two; three; six | pneumococcus |
| Pneumococcal capsular polysaccharide | Serotype 1 | one, two, three, five | pneumococcus, tuberculosis, staphylococcus |
| | Serotype 3 | five | pneumococcus, tuberculosis |
| | Serotype 5 | one; two; three; five | pneumococcus, tuberculosis |
| | Serotype 6B | two | pneumococcus |
| | Serotype 7 | three | pneumococcus |
| | Serotype 14 | one; two; three; five | pneumococcus, tuberculosis |
| | Serotype 19 | three | pneumococcus |
| Pneumococcal cell wall polysaccharide | | five | pneumococcus |
| *S. typhi* Vi polysaccharide | | five | pneumococcus |

Additional polymers that can be used in the immunogenic MAPS compositions described herein include polyethylene glycol-based polymers, poly(ortho ester) polymers, polyacryl carriers, PLGA, polyethylenimine (PEI), polyamidoamine (PAMAM) dendrimers, β-amino ester polymers, polyphosphoester (PPE), liposomes, polymerosomes, nucleic acids, phosphorothioated oligonucleotides, chitosan, silk, polymeric micelles, protein polymers, virus particles, virus-like-particles (VLPs) or other micro-particles. See, e.g., El-Sayed et al., *Smart Polymer Carriers for Enhanced Intracellular Delivery of Therapeutic Molecules*, 5 Exp. Op. Biol. Therapy, 23 (2005). Biocompatible polymers developed for nucleic acid delivery may be adapted for use as a backbone herein. See, e.g., BIOCOMPATIBLE POL. NUCL. ACID. DELIV. (Domb et al., eds., John Wiley & Sons, Inc. Hoboken, N.J., 2011).

For example, VLPs resemble viruses, but are non-infectious because they do not contain any viral genetic material. The expression, including recombinant expression, of viral structural proteins, such as envelope or capsid components, can result in the self-assembly of VLPs. VLPs have been produced from components of a wide variety of virus families including Parvoviridae (e.g., adeno-associated virus), Retroviridae (e.g., HIV), and Flaviviridae (e.g., Hepatitis B or C viruses). VLPs can be produced in a variety of cell culture systems including mammalian cell lines, insect cell lines, yeast, and plant cells. Recombinant VLPs are particularly advantageous because the viral component can be fused to recombinant antigens as described herein.

Antigens

The immunogenic compositions as disclosed herein can comprise any antigen that elicits an immune response in a subject. In some embodiments, at least one or more antigens are associated with the polymer of the composition. In some embodiments, at least 2, or at least 3, or at least 5, or at least 10, or at least 15, or at least 20, or at least 50, or at least 100, or more than 100 antigens can be associated with the polymer as disclosed herein. In some embodiments, where the immunogenic composition comprises more than one antigen, the antigens can be the same antigen or they can be a variety of different antigens associated with the polymer. In some embodiments, where the immunogenic composition comprises more than one antigen, the antigens can be antigens from the same pathogen or from different pathogens, or alternatively, can be different antigens from the same pathogen, or similar antigens from different serotypes of pathogens.

An antigen for use in the immunogenic compositions and methods described herein can be any antigen, including, but not limited to pathogenic peptides, toxins, toxoids, subunits thereof, or combinations thereof (e.g., cholera toxin, tetanus toxoid).

In some embodiments, an antigen, which can be fused to the complementary affinity molecule, can be any antigen associated with an infectious disease, or cancer or immune disease. In some embodiments, an antigen can be an antigen expressed by any of a variety of infectious agents, including virus, bacterium, fungus or parasite.

In some embodiments, an antigen is derived (e.g., obtained) from a pathogenic organism. In some embodiments, the antigen is a cancer or tumor antigen, e.g., an antigen derived from a tumor or cancer cell.

In some embodiments, an antigen derived from a pathogenic organism is an antigen associated with an infectious disease; it can be derived from any of a variety of infectious agents, including virus, bacterium, fungus or parasite.

In some embodiments, a target antigen is any antigen associated with a pathology, for example an infectious disease or pathogen, or cancer or an immune disease such as an autoimmune disease. In some embodiments, an antigen can be expressed by any of a variety of infectious agents, including virus, bacterium, fungus or parasite. A target antigen for use in the methods and compositions as disclosed herein can also include, for example, pathogenic peptides, toxins, toxoids, subunits thereof, or combinations thereof (e.g., cholera toxin, tetanus toxoid).

Non-limiting examples of infectious viruses include: Retroviridae; Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bungaviridae (for example, Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and HSV-2, varicella zoster virus, cytomegalovirus (CMV), Marek's disease virus, herpes viruses); Poxviridae (variola viruses, vaccinia viruses, pox viruses); and Iridoviridae (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses). The compositions and methods described herein are contemplated for use in treating infections with these viral agents.

Examples of fungal infections that may be addressed by inclusion of antigens in the present embodiments include aspergillosis; thrush (caused by *Candida albicans*); cryptococcosis (caused by *Cryptococcus*); and histoplasmosis. Thus, examples of infectious fungi include, but are not limited to, *Cryptococcus neoformans, Histoplasma capsulatum, Coccidioides immitis, Blastomyces dermatitidis, Chlamydia trachomatis, Candida albicans*. Components of these organisms can be included as antigens in the MAPS described herein.

In one aspect of the invention, an antigen is derived from an infectious microbe such as *Bordatella pertussis, Brucella, Enterococci* sp., *Neisseria meningitidis, Neisseria gonorrheae, Moraxella*, typeable or nontypeable *Haemophilus, Pseudomonas, Salmonella, Shigella, Enterobacter, Citrobacter, Klebsiella, E. coli, Helicobacter pylori, Clostridia, Bacteroides, Chlamydiaceae, Vibrio cholera, Mycoplasma, Treponemes, Borelia burgdorferi, Legionella pneumophilia, Mycobacteria* sps (such as *M. tuberculosis, M. avium, M. intracellulare, M. kansaii, M. gordonae, M. leprae*), *Staphylococcus aureus, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Leptospira* sps., *Pasturella multocida, Bacteroides* sp., *Fusobacterium nucleatum, Streptobacillus moniliformis, Treponema pallidium, Treponema pertenue*, and *Actinomyces israelli*. The compositions and methods described herein are contemplated for use in treating or preventing infections against these bacterial agents.

Additional parasite pathogens from which antigens can be derived include, for example: *Entamoeba histolytica, Plasmodium falciparum, Leishmania* sp., *Toxoplasma gondii, Rickettsia*, and the *Helminths*.

In another aspect of the invention, an antigen is a truncated pneumococcal PsaA protein, pneumolysin toxoid pneumococcal serine/threonine protein kinase (StkP), pneumococcal serine/threonine protein kinase repeating unit (StkPR), pneumococcal PcsB protein, staphylococcal alpha hemolysin, *Mycobacterium tuberculosis* mtb protein ESAT-6, *M. tuberculosis* cell wall core antigen, *Chlamydia* CT144, CT242 or CT812 polypeptides or fragments of these, *Chlamydia* DNA gyrase subunit B, *Chlamydia* sulfite synthesis/biphosphate phosphatase, *Chlamydia* cell division protein FtsY, *Chlamydia* methionyl-tRNA synthetase, *Chlamydia* DNA helicase (uvrD), *Chlamydia* ATP synthase subunit I (atpl), or *Chlamydia* metal dependent hydrolase.

An embodiment of the present invention provides for an immunogenic composition targeting the pathogen *Myocobacterium tuberculosis* (TB), an intracellular bacterial parasite. One example of a TB antigen is TbH9 (also known as Mtb 39A). Other TB antigens include, but are not limited to, DPV (also known as Mtb8.4), 381, Mtb41, Mtb40, Mtb32A, Mtb64, Mtb83, Mtb9.9A, Mtb9.8, Mtb16, Mtb72f, Mtb59f, Mtb88f, Mtb71f, Mtb46f and Mtb31f, wherein "f" indicates that it is a fusion or two or more proteins.

As noted above, an antigen can be derived from a *Chlamydia* species for use in the immunogenic compositions of the present invention. *Chlamydiaceae* (consisting of *Chlamydiae* and *Chlamydophila*), are obligate intracellular gram-negative bacteria. *Chlamydia trachomatis* infections are among the most prevalent bacterial sexually transmitted infections, and perhaps 89 million new cases of genital chlamydial infection occur each year. The *Chlamydia* of the present invention include, for example, *C. trachomatis*, *Chlamydophila pneumoniae*, *C. muridarum*, *C. suis*, *Chlamydophila abortus*, *Chlamydophila psittaci*, *Chlamydophila caviae*, *Chlamydophila felis*, *Chlamydophila pecorum*, and *C. pneumoniae*. Animal models of chlamydial infection have established that T-cells play a critical role both in the clearance of the initial infection and in protection from re-infection of susceptible hosts. Hence, the immunogenic compositions as disclosed herein can be used to provide particular value by eliciting cellular immune responses against chlamydial infection.

More specifically, Chlamydial antigens useful in the present invention include DNA gyrase subunit B, sulfite synthesis/biphosphate phosphatase, cell division protein FtsY, methionyl-tRNA synthetase, DNA helicase (uvrD); ATP synthase subunit I (atpl) or a metal-dependent hydrolase (U.S. Patent Application Pub. No. 20090028891). Additional *Chlamyidia trachomatis* antigens include CT144 polypeptide, a peptide having amino acid residues 67-86 of CT144, a peptide having amino acid residues 77-96 of CT144, CT242 protein, a peptide having amino acids 109-117 of CT242, a peptide having amino acids 112-120 of CT242 polypeptide, CT812 protein (from the pmpD gene), a peptide having amino acid residues 103-111 of the CT812 protein; and several other antigenic peptides from *C. trachomatis*: NVTQDLTSSTAKLECTQDLI (SEQ ID NO:2), AKLECTQDLIAQGKLIVTNP (SEQ ID NO:3), SNLKRMQKI (SEQ ID NO:4), AALYSTEDL (SEQ ID NO:5), FQEKDADTL (SEQ ID NO:6), QSVNELVYV (SEQ ID NO:7), LEFASCSSL (SEQ ID NO:8), SQAEGQYRL (SEQ ID NO:9), GQSVNELVY (SEQ ID NO:10), and QAVLLLDQI (SEQ ID NO:11). See WO 2009/020553. Additionally, *Chlamydia pneumoniae* antigens including homologues of the foregoing polypeptides (see U.S. Pat. No. 6,919,187), can be used an antigens in the immunogenic compositions and methods as disclosed herein.

Fungal antigens can be derived from *Candida* species and other yeast; or other fungi (aspergillus, other environmental fungi). Regarding other parasites, malaria as well as worms and amoebae may provide the antigenic antigen for use in the in the immunogenic compositions and methods as disclosed herein.

In some embodiments, where the antigen is to generate an anti-influenza immunogen, the surface glycoproteins hemagglutinin (HA) and neuraminidase (NA) are generally the antigens of choice. Both nucleoprotein (NP) polypeptide and matrix (M) are internal viral proteins and therefore not usually considered in vaccine design for antibody-based immunity. Influenza vaccines are used routinely in humans, and include vaccines derived from inactivated whole influenza virus, live attenuated influenza virus, or purified and inactivated materials from viral strains. For example, a traditional influenza vaccine can be manufactured using three potentially threatening strains of flu virus. These strains are usually grown in fertilized chicken eggs, which requires extensive processing including egg inoculation and incubation, egg harvest, virus purification and inactivation, processing and pooling the virus or viral components to the final vaccine formulation, and aseptic filling in the appropriate containers. Typically, this egg-based production cycle takes over 70 weeks. In the event of a major influenza epidemic, the availability of a potent and safe vaccine is a major concern. Additionally, there are risks associated with impurities in eggs, such as antibiotics and contaminants, that negatively impact vaccine sterility. Moreover, egg-derived flu vaccines are contraindicated for those with severe allergies to egg proteins and people with a history of Guillain-Barré syndrome. The present invention provides an alternative to the egg-based influenza vaccines, not only be avoiding egg-related selequae, but be providing a platform for the use of multiple influenza antigens in a highly controlled platform.

In some embodiments, an antigen for use in the immunogenic compositions as disclosed herein can also include those used in biological warfare, such as ricin, which may provoke a CMI response.

Additionally, the present invention also provides immunogenic compositions comprising antigens which raise an immune response against cancer. In these conjugates, an antigen is an antigen expressed by a cancer or tumor, or derived from a tumor. In some embodiments, such antigens are referred to herein as a "cancer antigen" and are typically a protein expressed predominantly on the cancer cells, such that the conjugate elicits both potent humoral and potent cellular immunity to this protein. A large number of cancer-associated antigens have been identified, several of which are now being used to make experimental cancer treatment vaccines and are thus suitable for use in the present embodiments. Antigens associated with more than one type of cancer include Carcinoembryonic antigen (CEA); Cancer/testis antigens, such as NY-ESO-1; Mucin-1 (MUC1) such as Sialyl Tn (STn); Gangliosides, such as GM3 and GD2; p53 protein; and HER2/neu protein (also known as ERBB2). Antigens unique to a specific type of cancer include a mutant form of the epidermal growth factor receptor, called EGFRvIII; Melanocyte/melanoma differentiation antigens, such as tyrosinase, MART1, gp100, the lineage related cancer-testis group (MAGE) and tyrosinase-related antigens; Prostate-specific antigen; Leukaemia-associated antigens (LAAs), such as the fusion protein BCR-ABL, Wilms' tumour protein and proteinase 3; and Idiotype (Id) antibodies. See, e.g., Mitchell, 3 Curr. Opin. Investig. Drugs 150 (2002); Dao & Scheinberg, 21 Best Pract. Res. Clin. Haematol. 391 (2008).

Another approach in generating an immune response against cancer employs antigens from microbes that cause or contribute to the development of cancer. These vaccines have been used against cancers including hepatocellular carcinoma (hepatitis B virus, hepatitis C virus, *Opisthorchis viverrin*), lymphoma and nasoparyngeal carcinoma (Epstei-Barr virus), colorectal cancer, stomach cancer (*Helicobacter*

*pylori*), bladder cancer (*Schisosoma hematobium*), T-cell leukemia (human T-cell lymphtropic virus), cervical cancer (human papillomavirus), and others. To date, there have been clinical trials for vaccines targeting Bladder Cancer, Brain Tumors, Breast Cancer, Cervical Cancer, Kidney Cancer, Melanoma, Multiple Myeloma, Leukemia, Lung Cancer, Pancreatic Cancer, Prostate Cancer, and Solid Tumors. See Pardoll et al., ABELOFF'S CLIN. ONCOL. (4th ed., Churchill Livingstone, Philadelphia 2008); Sioud, 360 Methods Mol. Bio. 277 (2007); Pazdur et al., 30 J. Infusion Nursing 30(3):173 (2007); Parmiani et al., 178 J. Immunol. 1975 (2007); Lollini et al., 24 Trends Immunol. 62 (2003); Schlom et al., 13 Clin. Cancer Res. 3776 (2007); Banchereau et al., 392 Nature 245 (1998); Finn, 358 New Engl. J. Med. 2704 (2008); Curigliano et al., 7 Exp. Rev. Anticancer Ther. 1225 (2007). Marek's Disease virus, a herpes virus that causes tumors in poultry, has long been managed by vaccine. Thus, the present embodiments encompass both preventive or prophylactic anti-cancer immunogenic compositions and treatment/therapeutic cancer vaccines.

Contemplated proliferative diseases and cancers include AIDS related cancers, acoustic neuroma, acute lymphocytic leukemia, acute myeloid leukemia, adenocystic carcinoma, adrenocortical cancer, agnogenic myeloid metaplasia, alopecia, alveolar soft-part sarcoma, anal cancer, angiosarcoma, astrocytoma, ataxia-telangiectasia, basal cell carcinoma (skin), bladder cancer, bone cancers, bowel cancer, brain and CNS tumors, breast cancer, carcinoid tumors, cervical cancer, childhood brain tumours, childhood cancer, childhood leukemia, childhood soft tissue sarcoma, chondrosarcoma, choriocarcinoma, chronic lymphocytic leukemia, chronic myeloid leukemia, colorectal cancers, cutaneous t-cell lymphoma, dermatofibrosarcoma-protuberans, desmoplastic-small-round-cell-tumour, ductal carcinoma, endocrine cancers, endometrial cancer, ependymoma, esophageal cancer, Ewing's sarcoma, extra-hepatic bile duct cancer, eye cancer, including, e.g., eye melanoma and retinoblastoma, fallopian tube cancer, fanconi anemia, fibrosarcoma, gall bladder cancer, gastric cancer, gastrointestinal cancers, gastrointestinal-carcinoid-tumour, genitourinary cancers, germ cell tumors, gestational-trophoblastic disease, glioma, gynecological cancers, hematological malignancies, hairy cell leukemia, head and neck cancer, hepatocellular cancer, hereditary breast cancer, Hodgkin's disease, human papillomavirus-related cervical cancer, hydatidiform mole, hypopharynx cancer, islet cell cancer, Kaposi's sarcoma, kidney cancer, laryngeal cancer, leiomyosarcoma, leukemia, Li-Fraumeni syndrome, lip cancer, liposarcoma, lung cancer, lymphedema, lymphoma, non-Hodgkin's lymphoma, male breast cancer, malignant-rhabdoid-tumour-of-kidney, medulloblastoma, melanoma, Merkel cell cancer, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, Nijmegen breakage syndrome, non-melanoma skin cancer, non-small-cell-lung-cancer-(NSCLC), oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal-tumours, pituitary cancer, polycythemia vera, prostate cancer, renal cell carcinoma, retinoblastoma, rhabdomyosarcoma, Rothmund-Thomson syndrome, salivary gland cancer, sarcoma, Schwannoma, Sezary syndrome, skin cancer, small cell lung cancer (SCLC), small intestine cancer, soft tissue sarcoma, spinal cord tumours, squamous-cell-carcinoma-(skin), stomach cancer, synovial sarcoma, testicular cancer, thymus cancer, thyroid cancer, transitional-cell-cancer-(bladder), transitional-cell-cancer (renal-pelvis/ureter), trophoblastic cancer, urethral cancer, urinary system cancer, uterine sarcoma, uterus cancer, vaginal cancer, vulva cancer, Waldenstrom's-macroglobulinemia, and Wilms' tumor.

In some embodiments, an antigen for use in the immunogenic compositions as disclosed herein can include antigens of autoimmune diseases, e.g., they can be "self-antigens." Autoimmune diseases contemplated for diagnosis according to the assays described herein include, but are not limited to alopecia areata, ankylosing spondylitis, antiphospholipid syndrome, Addison's disease, aplastic anemia, multiple sclerosis, autoimmune disease of the adrenal gland, autoimmune hemolytic anemia, autoimmune hepatitis, autoimmune oophoritis and orchitis, Behçet's Disease, bullous pemphigoid, cardiomyopathy, celiac sprue-dermatitis, chronic fatigue syndrome, chronic inflammatory demyelinating syndrome (CFIDS), chronic inflammatory polyneuropathy, Churg-Strauss syndrome, cicatricial pemphigoid, CREST Syndrome, cold agglutinin disease, Crohn's disease, dermatitis herpetiformis, discoid lupus, essential mixed cryoglobulinemia, fibromyalgia, glomerulonephritis, Grave's disease, Guillain-Barre, Hashimoto's thyroiditis, idiopathic pulmonary fibrosis, idiopathic thrombocytopenia purpura (ITP), IgA nephropathy, insulin dependent diabetes (Type I), Lichen Planus, lupus, Meniere's Disease, mixed connective tissue disease, myasthenia gravis, myocarditis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjogren's syndrome, stiff-man syndrome, Takayasu arteritis, temporal arteritis/giant cell arteritis, ulcerative colitis, uveitis, Wegener's syndrome, vasculitis and vitiligo. It is generally important to assess the potential or actual CMI responsiveness in subjects having, or suspected of having or being susceptible to an autoimmune disease.

In some embodiments, an antigen for use in the immunogenic compositions as disclosed herein can be an antigen which is associated with an inflammatory disease or condition. Examples of inflammatory disease conditions where antigens may be useful include but are not limited to acne, angina, arthritis, aspiration pneumonia, empyema, gastroenteritis, necrotizing enterocolitis, pelvic inflammatory disease, pharyngitis, pleurisy, chronic inflammatory demyelinating polyneuropathy, chronic inflammatory demyelinating polyradiculoneuropathy, and chronic inflammatory demyelinating polyneuropathy, among others.

In some embodiments, an antigen can be an intact (i.e., an entire or whole) antigen, or a functional portion of an antigen that comprises more than one epitope. In some embodiments, an antigen is a peptide functional portion of an antigen. By "intact" in this context is meant that the antigen is the full length antigen as that antigen polypeptide occurs in nature. This is in direct contrast to delivery of only a small portion or peptide of the antigen. Delivering an intact antigen to a cell enables or facilitates eliciting an immune response to a full range of epitopes of the intact antigen, rather than just a single or selected few peptide epitopes. Accordingly, the methods and immunogenic compositions described herein encompass intact antigens associated with the polymer for a more sensitive and have higher specificity of immune response as compared to use of a single epitope peptide-based antigen.

Alternatively, in some embodiments, an intact antigen can be divided into many parts, depending on the size of the initial antigen. Typically, where a whole antigen is a multimer polypeptide, the whole protein can be divided into sub-units and/or domains where each individual sub-unit or domain of the antigen can be associated with the polymer according to the methods as disclosed herein. Alternatively, in some embodiments, an intact antigen can be divided into functional fragments, or parts, of the whole antigen, for example, at least two, or at least 3, or at least 4, or at least 5, or at least 6, or at least 7, or at least 8, or at least 9, or at least 10, or at least 11, or at least 12, or at least 13, or at least 15, or at least 20, or at least 25, or more than 25 portions (e.g., pieces or fragments), inclusive, and where each individual functional fragment of the antigen can be associated with the polymer according to the methods as disclosed herein.

The fragmentation or division of a full length antigen polypeptide can be an equal division of the full length antigen polypeptide, or alternatively, in some embodiments, the fragmentation is asymmetrical or unequal. As a non-limiting example, where an antigen is divided into two overlapping fragments, an antigen can be divided into fragments of approximately the same (equal) size, or alternatively one fragment can be about 45% of the whole antigen and the other fragment can be about 65%. As further non-limiting examples, a whole antigen can be divided into a combination of differently sized fragments, for example, where an antigen is divided into two fragments, fragments can be divided into about 40% and about 70%, or about 45% and about 65%; or about 35% and about 75%; or about 25% and about 85%, inclusive, of the whole antigen. Any combination of overlapping fragments of a full length whole antigen is encompassed for use in the generation of a panel of overlapping polypeptides of an antigen. As an illustrative example only, where a antigen is divided into 5 portions, the portions can divided equally (i.e., each overlapping fragment is about 21% to 25% of the entire full length if the antigen) or unequally (i.e., an antigen can be divided into the following five overlapping fragments; fragment 1 is about 25%, fragment 2 is about 5%, fragment 3 is about 35%, fragment 4 is about 10% and fragment 5 is about 25% of the size of the full length antigen, provided each fragment overlaps with at least one other fragment).

Typically, a panel of antigen portions can substantially cover the entire length of the whole (or intact) antigen polypeptide. Accordingly, in some embodiments, an immunogenic composition comprises a polymer with many different, and/or overlapping fragments of the same intact antigen. Overlapping protein fragments of a antigen can be produced much quicker and cheaper, and with increased stability as compared to the use of peptide antigens alone. Further in some embodiments, antigens which are polypeptides larger than simple peptides are preferred as conformation is important for epitope recognition, and the larger antigen polypeptides or fragments will provide a benefit over peptide fragments.

One of ordinary skill in the art can divide a whole antigen into overlapping proteins of an antigen to create a panel of polypeptides of the antigen. By way of an illustrative example only, the TB-specific antigen TB1 (CFP also known as culture filtrate-10 or CFP-10) can be divided into, for example at least seventeen portions to generate a panel of seventeen different polypeptides, each comprising a different but overlapping TB-specific antigen TB1 (CFP) fragment. Culture filtrate protein (CFP-10) (Genbank AAC83445) is a 10 kDa,100 amino acid residue protein fragment from *M. tuberculosis*. It is also known as L45 antigen homologous protein (LHP).

A target antigen for use in the methods and compositions described herein can be expressed by recombinant means, and can optionally include an affinity or epitope tag to facilitate purification, which methods are well-known in the art. Chemical synthesis of an oligopeptide, either free or conjugated to carrier proteins, can be used to obtain antigen of the invention. Oligopeptides are considered a type of polypeptide. An antigen can be expressed as a fusion with a complementary affinity molecule, e.g., but not limited to rhizavidin or a derivative or functional fragment thereof. Alternatively, it is also possible to prepare target antigen and then conjugate it to a complementary affinity molecule, e.g., but not limited to rhizavidin or a derivative or functional fragment thereof.

Polypeptides can also by synthesized as branched structures such as those disclosed in U.S. Pat. Nos. 5,229,490 and 5,390,111. Antigenic polypeptides include, for example, synthetic or recombinant B-cell and T-cell epitopes, universal T-cell epitopes, and mixed T-cell epitopes from one organism or disease and B-cell epitopes from another.

An antigen can obtained through recombinant means or chemical polypeptide synthesis, as well as antigen obtained from natural sources or extracts, can be purified by means of the antigen's physical and chemical characteristics, such as by fractionation or chromatography. These techniques are well-known in the art.

In some embodiments, an antigen can be solubilized in water, a solvent such as methanol, or a buffer. Suitable buffers include, but are not limited to, phosphate buffered saline $Ca^{2+}/Mg^{2+}$ free (PBS), normal saline (150 mM NaCl in water), and Tris buffer. Antigen not soluble in neutral buffer can be solubilized in 10 mM acetic acid and then diluted to the desired volume with a neutral buffer such as PBS. In the case of antigen soluble only at acid pH, acetate-PBS at acid pH can be used as a diluent after solubilization in dilute acetic acid. Glycerol can be a suitable non-aqueous solvent for use the compositions, methods and kits described herein.

Typically, when designing a protein vaccine against a pathogen, an extracellular protein or one exposed to the environment on a virus is often the ideal candidate as the antigen component in the vaccine. Antibodies generated against that extracellular protein become the first line of defense against the pathogen during infection. The antibodies bind to the protein on the pathogen to facilitate antibody opsonization and mark the pathogen for ingestion and destruction by a phagocyte such as a macrophage. Antibody opsonization can also kill the pathogen by antibody-dependent cellular cytotoxicity. The antibody triggers a release of lysis products from cells such as monocytes, neutrophils, eosinophils, and natural killer cells.

In one embodiment of the invention described herein, antigens for use in the compositions as disclosed herein all wild type proteins, as in the amino acid residues have the sequences found in naturally occurring viruses and have not been altered by selective growth conditions or molecular biological methods.

In one embodiment, the immunogenic compositions described as herein can comprise antigens which are glycosylated proteins. In other words, an antigen of interest can each be a glycosylated protein. In one embodiment of the immunogenic compositions as described herein, antigens, or antigen-fusion polypeptides are O-linked glycosylated. In another embodiment of the immunogenic compositions as described herein, antigens, or antigen-fusion polypeptides are N-linked glycosylated. In yet another embodiment of the immunogenic compositions as described herein, antigens, or antigen-fusion are both O-linked and N-linked glycosylated. In other embodiments, other types of glycosylations are possible, e.g., C-mannosylation. Glycosylation of proteins occurs predominantly in eukaryotic cells. N-glycosylation is important for the folding of some eukaryotic proteins, providing a co-translational and post-translational modification mechanism that modulates the structure and function of membrane and secreted proteins. Glycosylation is the enzymatic process that links saccharides to produce glycans, and attaches them to proteins and lipids. In N-glycosylation, glycans are attached to the amide nitrogen of asparagine side chain during protein translation. The three major saccharides forming glycans are glucose, mannose, and N-acetylglucosamine molecules. The N-glycosylation consensus is Asn-Xaa-Ser/Thr, where Xaa can be any of the known amino acids. O-linked glycosylation occurs at a later stage during protein processing, probably in the Golgi apparatus. In O-linked glycosylation, N-acetyl-galactosamine, O-fucose, O-glucose, and/or N-acetylglucosamine is added to serine or threonine residues. One skilled in the art can use bioinformatics software such as NetNGlyc 1.0 and NetOGlyc Prediction softwares from the Technical University of Denmark to find the N- and O-glycosylation sites in a polypeptide in the present invention. The NetNglyc server predicts N-Glycosylation sites in proteins using artificial neural networks that examine the sequence context of Asn-Xaa-Ser/Thr sequons. The NetNGlyc 1.0 and NetOGlyc 3.1 Prediction software can be accessed at the EXPASY website. In one embodiment, N-glycosylation occurs in the target antigen polypeptide of the fusion polypeptide described herein.

Affinity Molecule Pairs:

As disclosed herein, in some embodiments, an antigen is connected to a polymer via complementary affinity pairs. This connecting of the antigen to the polymer is mediated by the polymer being connected to a first affinity molecule, which associates a second (e.g., complementary) affinity molecule, which is attached to the antigen. An example complementary affinity pair is biotin/biotin-binding protein.

Exemplary examples of the affinity complementary affinity pairs include, but without limitation, biotin binding proteins or avidin-like proteins that bind to biotin. For example, where the first affinity binding molecule is biotin (which associates with the polymer), the complementary affinity molecule can be a biotin binding protein or an avidin-like protein or a derivative thereof, e.g., but not limited to, avidin, rhizavidin, or streptavidin or variants, derivatives or functional portions thereof.

In some embodiments, the first affinity binding molecule is biotin, a biotin derivative, or a biotin mimic, for example, but not limited to, amine-PEG3-biotin (((+)-biotinylation-3-6,9-trixaundecanediamine) or a derivative or functional fragment thereof. A specific biotin mimetic has a specific peptide motif containing sequence of $DX_aAX_bPX_c$ (SEQ ID NO:12), or $CDX_aAX_bPX_cCG$ (SEQ ID NO:13), where $X_a$ is R or L, $X_b$ is S or T, and $X_c$ is Y or W. These motifs can bind avidin and Neutravidin, but streptavidin. See, e.g., Gaj et al., 56 Prot. Express. Purif. 54 (2006).

The linkage of the first affinity molecule to the polymer, and the complementary affinity molecule to the antigen can be a non-covalent linkage, or a chemical mechanism, for instance covalent binding, affinity binding, intercalation, coordinate binding and complexation. Covalent binding provides for very stable binding, and is particularly well-suited for the present embodiments. Covalent binding can be achieved either by direct condensation of existing side chains or by the incorporation of external bridging molecules.

For example, in some embodiments, an antigen can be non-covalently bonded to one of the pairs in a complementary affixing pair. In alternative embodiments, an antigen can be covalently bonded or fused to one of the pairs in a complementary affixing pair. Methods for generation of fusion proteins are well known in the art, and are discussed herein.

In other embodiments, a first affinity binding molecule is linked to the polymer by a non-covalent bond, or by a covalent bond. In some embodiments, a cross-linking reagent is used to covalently bond the first affinity binding molecule to the polymer as disclosed herein.

In some embodiments, the first affinity binding molecule associates with the complementary affinity molecule by non-covalent bond association as known in the art, including, but not limited to, electrostatic interaction, hydrogen bound, hydrophobic interaction (i.e., van der Waals forces), hydrophilic interactions, and other non-covalent interactions. Other higher order interactions with intermediate moieties are also contemplated.

In some embodiments, the complementary affinity molecule is an avidin-related polypeptide. In specific embodiments, the complementary affinity molecule is rhizavidin, such as recombinant rhizavidin. In particular, the recombinant rhizavidin is a modified rhizavidin that can be expressed in E. coli with a high yield. The typical yield is >30 mg per liter of E. coli culture. Rhizavidin has a lower sequence homology to egg avidin (22.4% sequence identity and 35.0% similarity) compared with other avidin-like proteins. Use of the modified rhizavidin reduces the risk of the MAPS inducing an egg-related allergic reaction in a subject. Moreover, antibody to recombinant modified rhizavidin has no apparent cross-reactivity to egg avidin (and vice versa).

More specifically, some embodiments comprise a modified rhizavidin designed for recombinant expression in E. coli. The coding sequence for the rhizavidin gene was optimized using E. coli expression codons, to avoid any difficulty during expression in E. coli due to rare codons present in original gene. To simplify the construct, after a bioinformatics and structure-based analysis, the first 44 residues of full length rhizavidin were removed, as these were found to be unnecessary for the core structure and function. The correct folding of recombinant protein was improved by added an E. coli secretion signal sequence to the N-terminal of the shortened rhizavidin (45-179), to facilitate the translocation of recombinant protein into the periplasmic space of E. coli cells where the functionally important disulfide bond in rhizavidin can form correctly. The modified recombinant rhizavidin forms a dimer, compared with known avidin-like proteins which form tetramers, further improving expression of the recombinant rhizavidin-antigen fusion as a soluble protein in E. coli.

Moreover, as discussed in further detail elsewhere herein, to improve the expression and solubility of fusion antigens in E. coli, a flexible linker region was added between rhizavidin and the antigen protein. Additionally, based on the biotinformatics and structural analysis, different antigen constructs were cloned and expressed: either full length antigen, or the important functional domain, or chimera proteins were comprising with two different antigens.

Additional affinity pairs that may be useful in the methods and compositions described herein include antigen-antibody, metal/ion-metal/ion-binding protein, lipid/lipid binding protein, saccharide/saccharide binding protein, amino acid/peptide/amino acid or peptide binding protein, enzyme-substrate or enzyme-inhibitor, ligand-agonist/receptor, or biotin mimetic. When using alternative affinity pairs, alternative means of attaching the respective polymer and antigen may also be employed, such as in vitro enzymatic reactions rather than genetic fusion. More specifically, antigen-antibody affinity pair provides for a very strong and specific interaction. The antigen can be any epitope including protein, peptide, nucleic acid, lipid, poly/oligosaccharide, ion, etc. The antibody can be any type of immunoglobulin, or the Ag-binding portion of an immunoglobulin, such as a Fab fragment. Regarding metal/ion-metal/ion binding protein, examples include Ni NTA vs. histidine-tagged protein, or Zn vs. Zn binding protein. Regarding lipid/lipid binding protein, examples include cholesterol vs. cholesterol binding protein. Regarding saccharide/saccharide binding protein, examples include maltose vs. maltose binding protein, mannose/glucose/oligosaccharide vs. lectin. Enzyme-substrate/inhibitors include substrates from a wide range of substances, including protein, peptide, amino acid, lipid, sugar, or ions. The inhibitor can be the analog of the real substrate which can generally bind to the enzymes more tightly and even irreversibly. For example, trypsin vs. soy trypsin inhibitor. The inhibitor can be natural or synthetic molecule. Regarding other ligand/agonist-receptor, ligand can be from a wide range of substance, including protein, peptide, amino acid, lipid, sugar, ion, agonist can be the analog of the real ligand. Examples include the LPS vs. TLR4 interaction.

Cross-Linking Reagents:

Many bivalent or polyvalent linking agents are useful in coupling protein molecules to other molecules. For example, representative coupling agents can include organic compounds such as thioesters, carbodiimides, succinimide esters, disocyanates, glutaraldehydes, diazobenzenes and hexamethylene diamines. This listing is not intended to be exhaustive of the various classes of coupling agents known in the art but, rather, is exemplary of the more common coupling agents. See Killen & Lindstrom, 133 J. Immunol. 1335 (1984); Jansen et al., 62 Imm. Rev. 185 (1982); Vitetta et al.

In some embodiments, cross-linking reagents agents described in the literature are encompassed for use in the methods, immunogenic compositions and kits as disclosed herein. See, e.g., Ramakrishnan, et al., 44 Cancer Res. 201 (1984) (describing the use of MBS (M-maleimidobenzoyl-N-hydroxysuccinimide ester)); Umemoto et al., U.S. Pat. No. 5,030,719 (describing the use of a halogenated acetyl hydrazide derivative coupled to an antibody by way of an oligopeptide linker). Particular linkers include: (a) EDC (1-ethyl-3-(3-dimethylamino-propyl) carbodiimide hydrochloride; (b) SMPT (4-succinimidyloxycarbonyl-alpha-methyl-alpha-(2-pyridyl-dithio)-toluene (Pierce Chem. Co., Cat. (21558G); (c) SPDP (succinimidyl-6 [3-(2-pyridyldithio) propionamido]hexanoate (Pierce Chem. Co., Cat #21651G); (d) Sulfo-LC-SPDP (sulfosuccinimidyl 6 [3-(2-pyridyldithio)-propianamide]hexanoate (Pierce Chem. Co. Cat. #2165-G); and (f) sulfo-NHS (N-hydroxysulfo-succinimide: Pierce Chem. Co., Cat. #24510) conjugated to EDC.

The linkages or linking agents described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage can be cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

Exemplary cross-linking molecules for use in the methods and immunogenic compostions as disclosed herein include, but are not limited to those listed in Tables 3 and 4.

TABLE 3

Exemplary homobifunctional crosslinkers*

| Crosslinking Target | Crosslinker Reactive Groups, Features | Example Products |
|---|---|---|
| Amine-to-Amine | NHS esters | DSG; DSS; BS3; TSAT (trifunctional); Bioconjugate Toolkit Reagent Pairs |
|  | NHS esters, PEG spacer | BS(PEG)5; BS(PEG)9 |
|  | NHS esters, thiol-cleavable | DSP; DTSSP |
|  | NHS esters, misc-cleavable | DST; BSOCOES; EGS; Sulfo-EGS |
|  | Imidoesters | DMA; DMP; DMS |
|  | Imidoesters, thiol-cleavable | DTBP |
|  | Other | DFDNB; THPP (trifunctional); Aldehyde-Activated Dextran Kit |
| Sulfhydryl-to-Sulfhydryl | Maleimides | BMOE; BMB; BMH; TMEA (trifunctional) |
|  | Maleimides, PEG spacer | BM(PEG)2; BM(PEG)3 |
|  | Maleimides, cleavable | BMDB; DTME |
|  | Pyridyldithiols (cleavable) | DPDPB |
|  | Other | HBVS (vinylsulfone) |
| Nonselective | Aryl azides | BASED (thiol-cleavable) |

*crosslinking reagents that have the same type of reactive group at either end. Reagents are classified by what chemical groups they cross link (left column) and their chemical composition (middle column). Products are listed in order of increasing length within each cell.

TABLE 4

Exemplary heterobifunctional crosslinkers*

| Crosslinking Targets | Crosslinker Reactive Groups, Features | Example Products |
|---|---|---|
| Amine-to-Sulfhydryl | NHS ester/Maleimide | AMAS; BMPS; GMBS and Sulfo-GMBS; MBS and Sulfo-MBS; SMCC and Sulfo-SMCC; EMCS and Sulfo-EMCS; SMPB and Sulfo-SMPB; SMPH; LC-SMCC; Sulfo-KMUS |
|  | NHS ester/Maleimide, PEG spacer | SM(PEG)2; SM(PEG)4; SM(PEG)6; SM(PEG)8; SM(PEG)12; SM(PEG)24 |
|  | NHS ester/Pyridyldithiol, cleavable | SPDP; LC-SPDP and Sulfo-LC-SPDP; SMPT; Sulfo-LC-SMPT |
|  | NHS esters/Haloacetyl | SIA; SBAP; SIAB; Sulfo-SIAB |

TABLE 4-continued

Exemplary heterobifunctional crosslinkers*

| Crosslinking Targets | Crosslinker Reactive Groups, Features | Example Products |
|---|---|---|
| Amine-to-Nonselective | NHS ester/Aryl Azide | NHS-ASA<br>ANB-NOS Sulfo-HSAB<br>Sulfo-NHS-LC-ASA<br>SANPAH and Sulfo-SANPAH |
| | NHS ester/Aryl Azide, cleavable | Sulfo-SFAD; Sulfo-SAND; Sulfo-SAED |
| | NHS ester/Diazirine | SDA and Sulfo-SDA; LC-SDA and Sulfo-LC-SDA |
| | NHS ester/Diazirine, cleavable | SDAD and Sulfo-SDAD |
| Amine-to-Carboxyl | Carbodiimide | DCC; EDC |
| Sulfhydryl-to-Nonselective | Pyridyldithiol/Aryl Azide | APDP |
| Sulfhydryl-to-Carbohydrate | Maleimide/Hydrazide | BMPH; EMCH; MPBH; KMUH |
| | Pyridyldithiol/Hydrazide | BMPH; EMCH; MPBH; KMUH |
| Carbohydrate-to-Nonselective | Hydrazide/Aryl Azide | ABH |
| Hydroxyl-to-Sulfhydryl | Isocyanate/Maleimide | PMPI |
| Amine-to-DNA | NHS ester/Psoralen | SPB |

*crosslinking reagents that have the different reactive groups at either end. Reagents are classified by what chemical groups they cross link (left column) and their chemical composition (middle column). Products are listed in order of increasing length within each cell.

Co-Stimulatory Factor

In some embodiments, the immunogenic composition as disclosed herein comprises at least one co-stimulatory molecule. In some embodiments, the co-stimulatory factor is cross-linked to the polymer. In some embodiments, the co-stimulatory factor is associated to the polymer by a complementary affinity pair similar to as an antigen is associated with the polymer. In some embodiments, where the complementary affinity pair which links the co-stimulatory factor to the polymer is the same, or a different complementary affinity pair which links the antigen to the polymer.

In some embodiments, at least one, or at least 2, or at least 3, or at least 5, or at least 10, or at least 15, or at least 20, or at least 50, or at least 100, or more than about 100, inclusive, co-stimulatory factors can be associated with the polymer as disclosed herein. In some embodiments, the co-stimulatory factors can be the same co-stimulator factor, or they can be a variety of different co-stimulatory factors associated with the polymer.

In some embodiments, the co-stimulator factor is a ligand/agonist of Toll like receptors, e.g., but not limited to TLR1, TLR2, TLR3, TLR4, TLR5, TLR6, TLR7, TLR8, TLR9, TLR10, TLR11, etc. In some embodiments, a co-stimulator factor is a NOD ligand/agonist, or an activator/agonist of the inflammasome. Without wishing to be bound by theory, the inflammasome is a multiprotein oligomer consisting of caspase 1, PYCARD, NALP and sometimes caspase 5 or caspase 11 and promotes the maturation of inflammatory cytokines interleukin 1β and interleukin 18.

In some embodiments, a co-stimulator factor is a cytokine. In some embodiments, a cytokine is selected from the group consisting of: GM-CSF; IL-1α; IL-1β; IL-2; IL-3; IL-4; IL-5; IL-6; IL-7; IL-8; IL-10; IL-12; IL-23; IFN-α; IFN-β; IFN-β; IFN-γ; MIP-1α; MIP-1β; TGF-β; TNFα, and TNFβ. In some embodiments, the co-stimulatory factor is an adjuvant, which may be associated with the polymer, as just discussed, or may be added to the MAPS composition prior to or concurrent with administration to a subject. Adjuvants are further described elsewhere herein.

Production of Antigens and Antigens Fused to the Complementary Affinity Molecule Recombinant proteins may be conveniently expressed and purified by a person skilled in the art, or by using commercially available kits, for example PROBoND™ Purification System (Invitrogen Corp., Carlsbad, Calif.). In some embodiments, recombinant antigens can be synthesized and purified by protein purification methods using bacterial expression systems, yeast expression systems, baculovirus/insect cell expression system, mammalian cell expression systems, or transgenic plant or animal systems as known to persons of ordinary skill in the art.

The fusion polypeptides described herein can all be synthesized and purified by protein and molecular methods that are well known to one skilled in the art. Molecular biology methods and recombinant heterologous protein expression systems are used. For example, recombinant protein can be expressed in bacteria, mammalian, insect, yeast, or plant cells; or in transgenic plant or animal hosts.

In one embodiment, provided herein is an isolated polynucleotide encoding a fusion polypeptide or a non-fusion polypeptide described herein. Conventional polymerase chain reaction (PCR) cloning techniques can be used to construct a chimeric or fusion coding sequence encoding a fusion polypeptide as described herein. A coding sequence can be cloned into a general purpose cloning vector such as pUC19, pBR322, pBLUESCRIPT® vectors (Stratagene, Inc.) or pCR TOPO® (Invitrogen). The resultant recombinant vector carrying the nucleic acid encoding a polypeptide as described herein can then be used for further molecular biological manipulations such as site-directed mutagenesis to create a variant fusion polypeptide as described herein or can be subcloned into protein expression vectors or viral vectors for protein synthesis in a variety of protein expression systems using host cells selected from the group consisting of mammalian cell lines, insect cell lines, yeast, bacteria, and plant cells.

Each PCR primer should have at least 15 nucleotides overlapping with its corresponding templates at the region to be amplified. The polymerase used in the PCR amplification should have high fidelity such as PfuULTRA® polymerase (Stratagene) for reducing sequence mistakes during the PCR amplification process. For ease of ligating several separate PCR fragments together, for example in the construction of a fusion polypeptide, and subsequently inserting into a cloning vector, the PCR primers should also have distinct and unique restriction digestion sites on their flanking ends that do not anneal to the DNA template during PCR amplification. The choice of the restriction digestion sites for each pair of specific primers should be such that the fusion polypeptide coding DNA sequence is in-frame and will encode the fusion polypeptide from beginning to end with no stop codons. At the same time the chosen restriction digestion sites should not be found within the coding DNA sequence for the fusion polypeptide. The coding DNA sequence for the intended polypeptide can be ligated into cloning vector pBR322 or one of its derivatives, for amplification, verification of fidelity and authenticity of the chimeric coding sequence, substitutions/or specific site-directed mutagenesis for specific amino acid mutations and substitutions in the polypeptide.

Alternatively the coding DNA sequence for the polypeptide can be PCR cloned into a vector using for example, the TOPO® cloning method comprising topoisomerase-assisted TA vectors such as pCR®-TOPO, pCR®-Blunt II-TOPO, pENTR/D-TOPO®, and pENTR/SD/D-TOPO®. (Invitrogen, Inc., Carlsbad, Calif.). Both pENTR/D-TOPO®, and pENTR/SD/D-TOPO® are directional TOPO entry vectors which allow the cloning of the DNA sequence in the 5'→3' orientation into a GATEWAY® expression vector. Directional cloning in the 5'→3' orientation facilitates the unidirectional insertion of the DNA sequence into a protein expression vector such that the promoter is upstream of the 5' ATG start codon of the fusion polypeptide coding DNA sequence, enabling promoter driven protein expression. The recombinant vector carrying the coding DNA sequence for the fusion polypeptide can be transfected into and propagated in general cloning E. coli such as XL1Blue, SURE® (STRATAGENE®) and TOP-10 cells (Invitrogen).

One skilled in the art would be able to clone and ligate the coding region of the antigen of interest with the coding region of the complementary affinity molecule to construct a chimeric coding sequence for a fusion polypeptide comprising the antigen or a fragment thereof and the complementary affinity molecule of a derivative thereof using specially designed oligonucleotide probes and polymerase chain reaction (PCR) methodologies that are well known in the art. One skilled in the art would also be able to clone and ligate the chimeric coding sequence for a fusion protein into a selected vector, e.g., bacterial expression vector, an insect expression vector or baculovirus expression vector. The coding sequences of antigen and the target antigen polypeptide or fragment thereof should be ligated in-frame and the chimeric coding sequence should be ligated downstream of the promoter, and between the promoter and the transcription terminator. Subsequent to that, the recombinant vector is transfected into regular cloning E. coli, such as XL1Blue. Recombinant E. coli harboring the transfer vector DNA is then selected by antibiotic resistance to remove any E. coli harboring non-recombinant plasmid DNA. The selected transformant E. coli are grown and the recombinant vector DNA can be subsequently purified for transfection into S. frugiperda cells.

In some embodiments, the antigens as disclosed herein can comprise a signal peptide for translocation into periplasmic space of bacteria. The signal peptide is also called a leader peptide in the N-terminus, which may or may not be cleaved off after the translocation through the membrane. One example of a signal peptide is MKKIWLALAGLV-LAFSASA (SEQ ID NO:1) as disclosed herein. Another signal sequence is MAPFEPLASGILLLLWLIAPSRA (SEQ ID NO:14). Other examples of signal peptides can be found at SPdb, a Signal Peptide Database, which is found at the world wide web site of "proline.bic.nus.edu.sg/spdb/".

In some embodiments, where the antigen is fused to a complementary affinity protein, the signal sequence can be located at the N-terminal of the complementary affinity protein. For example, if an antigen is fused to an avidin-like protein, the signal sequence can be located at the N-terminal of the complementary affinity protein. In some embodiments, the signal sequence is cleaved off from the complementary affinity protein before the complementary affinity protein associates with the first affinity molecule.

In some embodiments, an antigen and/or complementary affinity protein as described herein lacks a signal sequence.

The polypeptides described herein can be expressed in a variety of expression host cells e.g., bacteria, yeasts, mammalian cells, insect cells, plant cells, algal cells such as Chlamadomonas, or in cell-free expression systems. In some embodiments the nucleic acid can be subcloned from the cloning vector into a recombinant expression vector that is appropriate for the expression of fusion polypeptide in bacteria, mammalian, insect, yeast, or plant cells or a cell-free expression system such as a rabbit reticulocyte expression system. Some vectors are designed to transfer coding nucleic acid for expression in mammalian cells, insect cells and year in one single recombination reaction. For example, some of the GATEWAY® (Invitrogen) destination vectors are designed for the construction of baculovirus, adenovirus, adeno-associated virus (AAV), retrovirus, and lentiviruses, which upon infecting their respective host cells, permit heterologous expression of fusion polypeptides in the appropriate host cells. Transferring a gene into a destination vector is accomplished in just two steps according to manufacturer's instructions. There are GATEWAY® expression vectors for protein expression in insect cells, mammalian cells, and yeast. Following transformation and selection in E. coli, the expression vector is ready to be used for expression in the appropriate host.

Examples of other expression vectors and host cells are the strong CMV promoter-based pcDNA3.1 (Invitrogen) and pCINEO vectors (Promega) for expression in mammalian cell lines such as CHO, COS, HEK-293, Jurkat, and MCF-7; replication incompetent adenoviral vector vectors pADENO-X™, pAd5F35, pLP-ADENO™-X-CMV (CLONTECH®), pAd/CMV/V5-DEST, pAd-DEST vector (Invitrogen) for adenovirus-mediated gene transfer and expression in mammalian cells; pLNCX2, pLXSN, and pLAPSN retrovirus vectors for use with the RETRO-X™ system from Clontech for retroviral-mediated gene transfer and expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells; adenovirus-associated virus expression vectors such as pAAV-MCS, pAAV-IRES-hrGFP, and pAAV-RC vector (Stratagene) for adeno-associated virus-mediated gene transfer and expression in mammalian cells; BACpak6 baculovirus (Clontech) and pFASTBAC™ HT (Invitrogen) for the expression in S. frugiperda 9 (Sf9), Sf11, Tn-368 and BTI-TN-5B4-1 insect cell lines; pMT/BiP/V5-His (Invitrogen) for the expression in Drosophila schneider S2 cells; Pichia expression vectors pPICZα, pPICZ, pFLDα and pFLD (Invitrogen) for expression in P. pastoris and vectors pMETα and pMET for expression in P. methanolica; pYES2/GS and pYD1 (Invitrogen) vectors for expression in yeast S. cerevisiae.

Recent advances in the large scale expression heterologous proteins in Chlamydomonas reinhardtii are described. Griesbeck., 34 Mol. Biotechnol. 213 (2006); Fuhrmann, 94 Methods Mol Med. 191 (2006). Foreign heterologous coding sequences are inserted into the genome of the nucleus, chloroplast and mitochondria by homologous recombination. The chloroplast expression vector p64 carrying the most versatile chloroplast selectable marker aminoglycoside adenyl transferase (aadA), which confer resistance to spectinomycin or streptomycin, can be used to express foreign protein in the chloroplast. The biolistic gene gun method can be used to introduce the vector in the algae. Upon its entry into chloroplasts, the foreign DNA is released from the gene gun particles and integrates into the chloroplast genome through homologous recombination.

Also included in the invention are complementary affinity molecule fused to an antigen. In some embodiments, the fusion construct can also optionally comprise purification tags, and/or secretion signal peptides. These fusion proteins may be produced by any standard method. For example, for production of a stable cell line expressing an antigen-complementary affinity molecule fusion protein, PCR-amplified antigen nucleic acids may be cloned into the restriction site of a derivative of a mammalian expression vector. For example, KA, which is a derivative of pcDNA3 (Invitrogen) contains a DNA fragment encoding an influenza virus hemagglutinin tag (HA). Alternatively, vector derivatives encoding other tags, such as c-myc or poly Histidine tags, can be used. The antigen-complementary affinity molecule fusion expression construct may be co-transfected, with a marker plasmid, into an appropriate mammalian cell line (e.g., COS, HEK293T, or NIH 3T3 cells) using, for example, LIPOFECTAMINE™ (Gibco-BRL, Gaithersburg, Md.) according to the manufacturer's instructions, or any other suitable transfection technique known in the art. Suitable transfection markers include, for example, β-galactosidase or green fluorescent protein (GFP) expression plasmids or any plasmid that does not contain the same detectable marker as the antigen-complementary affinity molecule fusion protein. The fusion protein expressing cells can be sorted and further cultured, or the tagged antigen-complementary affinity molecule fusion protein can be purified. In some embodiments, an antigen-complementary affinity molecule fusion protein is amplified with a signal peptide. In alternative embodiments, a cDNA encoding an antigen-complementary affinity molecule fusion protein can be amplified without the signal peptide and subcloned into a vector (pSecTagHis) having a strong secretion signal peptide. In another example, antigen-complementary affinity molecule fusion protein can have an alkaline phosphatase (AP) tag, or a histadine (His) tag for purification. Any method known to persons of ordinary skill in the art for protein purification of the antigen and/or antigen-complementary affinity molecule fusion protein is encompassed for use in the methods of the invention.

In some embodiments, any of the polypeptides described herein is produced by expression from a recombinant baculovirus vector. In another embodiment, any of the polypeptides described herein is expressed by an insect cell. In yet another embodiment, any of the polypeptides described herein is isolated from an insect cell. There are several benefits of protein expression with baculovirus in insect cells, including high expression levels, ease of scale-up, production of proteins with posttranslational modifications, and simplified cell growth. Insect cells do not require $CO_2$ for growth and can be readily adapted to high-density suspension culture for large-scale expression. Many of the post-translational modification pathways present in mammalian systems are also utilized in insect cells, allowing the production of recombinant protein that is antigenically, immunogenically, and functionally similar to the native mammalian protein.

Baculoviruses are DNA viruses in the family Baculoviridae. These viruses are known to have a narrow host-range that is limited primarily to Lepidopteran species of insects (butterflies and moths). The baculovirus Autographa californica Nuclear Polyhedrosis Virus (AcNPV), which has become the prototype baculovirus, replicates efficiently in susceptible cultured insect cells. AcNPV has a double-stranded closed circular DNA genome of about 130,000 base-pairs and is well characterized with regard to host range, molecular biology, and genetics. The Baculovirus Expression Vector System (BEVS) is a safe and rapid method for the abundant production of recombinant proteins in insect cells and insects. Baculovirus expression systems are powerful and versatile systems for high-level, recombinant protein expression in insect cells. Expression levels up to 500 mg/l have been reported using the baculovirus expression system, making it an ideal system for high-level expression. Recombinant baculoviruses that express foreign genes are constructed by way of homologous recombination between baculovirus DNA and chimeric plasmids containing the gene sequence of interest. Recombinant viruses can be detected by virtue of their distinct plaque morphology and plaque-purified to homogeneity.

Recombinant fusion proteins described herein can be produced in insect cells including, but not limited to, cells derived from the Lepidopteran species S. frugiperda. Other insect cells that can be infected by baculovirus, such as those from the species Bombyx mori, Galleria mellanoma, Trichplusia ni, or Lamanthria dispar, can also be used as a suitable substrate to produce recombinant proteins described herein. Baculovirus expression of recombinant proteins is well known in the art. See U.S. Pat. No. 4,745,051; No. 4,879,236; No. 5,179,007; No. 5,516,657; No. 5,571,709; No. 5,759,809. It will be understood by those skilled in the art that the expression system is not limited to a baculovirus expression system. What is important is that the expression system directs the N-glycosylation of expressed recombinant proteins. The recombinant proteins described herein can also be expressed in other expression systems such as Entomopox viruses (the poxviruses of insects), cytoplasmic polyhedrosis viruses (CPV), and transformation of insect cells with the recombinant gene or genes constitutive expression. A good number of baculovirus transfer vectors and the corresponding appropriately modified host cells are commercially available, for example, pAcGP67, pAcSECG2TA, pVL1392, pVL1393, pAcGHLT, and pAcAB4 from BD Biosciences; pBAC-3, pBAC-6, pBACgus-6, and pBACsurf-1 from NOVAGEN®, and pPolh-FLAG and pPolh-MAT from SIGMA ALDRICH®.

The region between the promoter and the transcriptional terminator can have multiple restriction enzyme digestion sites for facilitating cloning of the foreign coding sequence, in this instance, the coding DNA sequence for an antigen polypeptide, and a complementary affinity molecule. Additional sequences can be included, e.g., signal peptides and/or tag coding sequences, such as His-tag, MAT-Tag, FLAG tag, recognition sequence for enterokinase, honeybee melittin secretion signal, beta-galactosidase, glutathione S-transferase (GST) tag upstream of the MCS for facilitating the secretion, identification, proper insertion, positive selection of recombinant virus, and/or purification of the recombinant protein.

In some embodiments, the fusion protein can comprise an N-terminal signal sequence as disclosed herein. In some embodiments, the signal sequence is attached to the N-terminal of the complementary affinity molecule as disclosed herein.

In some embodiments, a fusion polypeptide as described herein has a spacer peptide, e.g., a 14-residue spacer (GSP-GISGGGGILE) (SEQ ID NO:15) separating antigen from the complementary affinity molecule. The coding sequence of such a short spacer can be constructed by annealing a complementary pair of primers. One of skill in the art can design and synthesize oligonucleotides that will code for the selected spacer. Spacer peptides should generally have non-polar amino acid residues, such as glycine and proline.

Standard techniques known to those of skill in the art can be used to introduce mutations (to create amino acid substitutions in an antigen polypeptide sequence of the fusion polypeptide described herein, e.g., in the antigen in the nucleotide sequence encoding the fusion polypeptide described herein, including, for example, site-directed mutagenesis and PCR-mediated mutagenesis. Preferably, the variant fusion polypeptide has less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions, inclusive, relative to the fusion polypeptides described herein.

Certain silent or neutral missense mutations can also be made in the DNA coding sequence that do not change the encoded amino acid sequence or the capability to promote transmembrane delivery. These types of mutations are useful to optimize codon usage, or to improve recombinant protein expression and production.

Specific site-directed mutagenesis of a coding sequence for the fusion polypeptide in a vector can be used to create specific amino acid mutations and substitutions. Site-directed mutagenesis can be carried out using, e.g., the QUICKCHANGE® site-directed mutagenesis kit from Stratagene according to the manufacturer's instructions.

In one embodiment, described herein are expression vectors comprising the coding DNA sequence for the polypeptides described herein for the expression and purification of the recombinant polypeptide produced from a protein expression system using host cells selected from, e.g., bacteria, mammalian, insect, yeast, or plant cells. The expression vector should have the necessary 5' upstream and 3' downstream regulatory elements such as promoter sequences, ribosome recognition and TATA box, and 3' UTR AAUAAA transcription termination sequence for efficient gene transcription and translation in its respective host cell. The expression vector is, preferably, a vector having the transcription promoter selected from a group consisting of CMV (cytomegalovirus) promoter, RSV (Rous sarcoma virus) promoter, β-actin promoter, SV40 (simian virus 40) promoter and muscle creatine kinase promoter, and the transcription terminator selected from a group consisting of SV40 poly(A) and BGH terminator; more preferably, an expression vector having the early promoter/enhancer sequence of cytomegalovirus and the adenovirus tripartite leader/intron sequence and containing the replication orgin and poly(A) sequence of SV40. The expression vector can have additional coding regions, such as those encoding, for example, 6X-histidine (SEQ ID NO: 28), V5, thioredoxin, glutathione-S-transferase, c-Myc, VSV-G, HSV, FLAG, maltose binding peptide, metal-binding peptide, HA and "secretion" signals (Honeybee melittin, α-factor, PHO, Bip), which can be incorporated into the expressed fusion polypeptide. In addition, there can be enzyme digestion sites incorporated after these coding regions to facilitate their enzymatic removal if they are not needed. These additional nucleic acids are useful for the detection of fusion polypeptide expression, for protein purification by affinity chromatography, enhanced solubility of the recombinant protein in the host cytoplasm, and/or for secreting the expressed fusion polypeptide out into the culture media or the spheroplast of the yeast cells. The expression of the fusion polypeptide can be constitutive in the host cells or it can be induced, e.g., with copper sulfate, sugars such as galactose, methanol, methylamine, thiamine, tetracycline, infection with baculovirus, and (isopropyl-beta-D-thiogalactopyranoside) IPTG, a stable synthetic analog of lactose.

In another embodiment, the expression vector comprising a polynucleotide described herein is a viral vector, such as adenovirus, adeno-associated virus (AAV), retrovirus, and lentivirus vectors, among others. Recombinant viruses provide a versatile system for gene expression studies and therapeutic applications.

In some embodiments, the fusion polypeptides described herein are expressed from viral infection of mammalian cells. The viral vectors can be, for example, adenovirus, adeno-associated virus (AAV), retrovirus, and lentivirus. A simplified system for generating recombinant adenoviruses is presented by He et al., 95 PNAS 2509 (1998). The gene of interest is first cloned into a shuttle vector, e.g., pAdTrack-CMV. The resultant plasmid is linearized by digesting with restriction endonuclease PmeI, and subsequently cotransformed into E. coli. BJ5183 cells with an adenoviral backbone plasmid, e.g. pADEASY-1 of Stratagene's ADEASY™ Adenoviral Vector System. Recombinant adenovirus vectors are selected for kanamycin resistance, and recombination confirmed by restriction endonuclease analyses. Finally, the linearized recombinant plasmid is transfected into adenovirus packaging cell lines, for example HEK 293 cells (E1-transformed human embryonic kidney cells) or 911 (E1-transformed human embryonic retinal cells). Fallaux, et al. 7 Human Gene Ther. 215 (1996). Recombinant adenovirus are generated within the HEK 293 cells.

Recombinant lentivirus has the advantage of delivery and expression of fusion polypeptides in dividing and non-dividing mammalian cells. The HIV-1 based lentivirus can effectively transduce a broader host range than the Moloney Leukemia Virus (MoMLV)-based retroviral systems. Preparation of the recombinant lentivirus can be achieved using, for example, the pLenti4/V5-DEST™, pLenti6/V5-DEST™ or pLenti vectors together with VIRAPOWER™ Lentiviral Expression systems from Invitrogen, Inc.

Recombinant adeno-associated virus (rAAV) vectors are applicable to a wide range of host cells including many different human and non-human cell lines or tissues. rAAVs are capable of transducing a broad range of cell types and transduction is not dependent on active host cell division. High titers, >$10^8$ viral particle/ml, are easily obtained in the supernatant and $10^{11}$-$10^{12}$ viral particle/ml with further concentration. The transgene is integrated into the host genome so expression is long term and stable.

Large scale preparation of AAV vectors is made by a three-plasmid cotransfection of a packaging cell line: AAV vector carrying the coding nucleic acid, AAV RC vector containing AAV rep and cap genes, and adenovirus helper plasmid pDF6, into 50×150 mm plates of subconfluent 293 cells. Cells are harvested three days after transfection, and viruses are released by three freeze-thaw cycles or by sonication.

AAV vectors can be purified by two different methods depending on the serotype of the vector. AAV2 vector is purified by the single-step gravity-flow column purification method based on its affinity for heparin. Auricchio et. al., 12 Human Gene Ther. 71 (2001); Summerford & Samulski, 72 J. Virol. 1438 (1998); Summerford & Samulski, 5 Nat. Med. 587 (1999). AAV2/1 and AAV2/5 vectors are currently purified by three sequential CsCl gradients.

Without wishing to be bound to theory, when proteins are expressed by a cell, including a bacterial cell, the proteins are targeted to a particular part in the cell or secreted from the cell. Thus, protein targeting or protein sorting is the mechanism by which a cell transports proteins to the appropriate positions in the cell or outside of it. Sorting targets can be the inner space of an organelle, any of several interior membranes, the cell's outer membrane, or its exterior via secretion. This delivery process is carried out based on information contained in the protein itself. Correct sorting is crucial for the cell; errors can lead to diseases.

With some exceptions, bacteria lack membrane-bound organelles as found in eukaryotes, but they may assemble proteins onto various types of inclusions such as gas vesicles and storage granules. Also, depending on the species of bacteria, bacteria may have a single plasma membrane (Gram-positive bacteria), or both an inner (plasma) membrane and an outer cell wall membrane, with an aqueous space between the two called the periplasm (Gram-negative bacteria). Proteins can be secreted into the environment, according to whether or not there is an outer membrane. The basic mechanism at the plasma membrane is similar to the eukaryotic one. In addition, bacteria may target proteins into or across the outer membrane. Systems for secreting proteins across the bacterial outer membrane may be quite complex and play key roles in pathogenesis. These systems may be described as type I secretion, type II secretion, etc.

In most Gram-positive bacteria, certain proteins are targeted for export across the plasma membrane and subsequent covalent attachment to the bacterial cell wall. A specialized enzyme, sortase, cleaves the target protein at a characteristic recognition site near the protein C-terminus, such as an LPXTG motif (SEQ ID NO:16) (where X can be any amino acid), then transfers the protein onto the cell wall. A system analogous to sortase/LPXTG (SEQ ID NO: 16), having the motif PEP-CTERM (SEQ ID NO:17), termed exosortase/PEP-CTERM (SEQ ID NO: 17), is proposed to exist in a broad range of Gram-negative bacteria.

Proteins with appropriate N-terminal targeting signals are synthesized in the cytoplasm and then directed to a specific protein transport pathway. During, or shortly after its translocation across the cytoplasmic membrane, the protein is processed and folded into its active form. Then the translocated protein is either retained at the periplasmic side of the cell or released into the environment. Since the signal peptides that target proteins to the membrane are key determinants for transport pathway specificity, these signal peptides are classified according to the transport pathway to which they direct proteins. Signal peptide classification is based on the type of signal peptidase (SPase) that is responsible for the removal of the signal peptide. The majority of exported proteins are exported from the cytoplasm via the general "Secretory (Sec) pathway". Most well known virulence factors (e.g. exotoxins of *Staphylococcus aureus*, protective antigen of *Bacillus anthracis*, lysteriolysin O of *Listeria monocytogenes*) that are secreted by Gram-positive pathogens have a typical N-terminal signal peptide that would lead them to the Sec-pathway. Proteins that are secreted via this pathway are translocated across the cytoplasmic membrane in an unfolded state. Subsequent processing and folding of these proteins takes place in the cell wall environment on the trans-side of the membrane. In addition to the Sec system, some Gram-positive bacteria also contain the Tat-system that is able to translocate folded proteins across the membrane. Pathogenic bacteria may contain certain special purpose export systems that are specifically involved in the transport of only a few proteins. For example, several gene clusters have been identified in mycobacteria that encode proteins that are secreted into the environment via specific pathways (ESAT-6) and are important for mycobacterial pathogenesis. Specific ATP-binding cassette (ABC) transporters direct the export and processing of small antibacterial peptides called bacteriocins. Genes for endolysins that are responsible for the onset of bacterial lysis are often located near genes that encode for holin-like proteins, suggesting that these holins are responsible for endolysin export to the cell wall. Wooldridge, BACT. SECREILD PROTS: SECRETORY MECHS. & ROLE IN PATHOGEN. (Caister Academic Press, 2009)

In some embodiments, the signal sequence useful in the present invention is OmpA Signal sequence, however any signal sequence commonly known by persons of ordinary skill in the art which allows the transport and secretion of antimicrobial agents outside the bacteriophage infected cell are encompassed for use in the present invention.

Signal sequence that direct secretion of proteins from bacterial cells are well known in the art, for example as disclosed in International application WO 2005/071088. For example, one can use some of the non-limited examples of signal peptide shown in Table 5, which can be attached to the amino-terminus or carboxyl terminus of the antimicrobial peptide (Amp) or antimicrobial polypeptide to be expressed by the antimicrobial-agent engineered bacteriophage, e.g., AMP-engineered bacteriophage. Attachment can be via fusion or chimera composition with selected antigen or antigen-complementary affinity molecule fusion protein resulting in the secretion from the bacterium infected with the antimicrobial-agent engineered bacteriophage, e.g. AMP-engineered bacteriophage.

TABLE 5

Example signal peptides to direct secretion of a protein or peptide antigen or antigen-complementary affinity molecule fusion protein of a bacterial cell

| Secretion Pathway | Signal Peptide Amino Acid sequence (NH$_2$—CO$_2$) | Gene | Genus/Species |
| --- | --- | --- | --- |
| secA1 | MKKIMLVITLILVSPIAQQTEAKD (SEQ ID NO: 18) | Hly (LLO) | *Listeria monocytogenes* |
|  | MKKKIISAILMSTVILSAAAPLSGVYADT (SEQ ID NO: 19) | Usp45 | *Lactococcus lactis* |
|  | MKKRKVLIPLMALSTILVSSTGNLEVIQAEV (SEQ ID NO: 20) | Pag (protective antigen) | *Bacillus anthracis* |
| secA2 | MNMKKATIAATAGIAVTAFAAPTIASAST (SEQ ID NO: 21) | Iap (invasion-associated protein p60) | *Listeria monocytogenes* |
|  | MQKTRKERILEALQEEKKNKKSKKFKTGATIAGVTAIATSITVPGIEVIVSADE (SEQ ID NO: 22) | NamA lmo2691 (autolysin) | *Listeria monocytogenes* |
|  | MKKLKMASCALVAGLMFSGLTPNAFAED (SEQ ID NO: 23) | *BA_0281 (NLP/P60 family) | *Bacillus anthracis* |

TABLE 5-continued

Example signal peptides to direct secretion of a protein or peptide antigen or antigen-complementary affinity molecule fusion protein of a bacterial cell

| Secretion Pathway | Signal Peptide Amino Acid sequence ($NH_2$–$CO_2$) | Gene | Genus/Species |
|---|---|---|---|
| | MAKKFNYKLPSMVALTLVGSA VTAHQVQAAE (SEQ ID NO: 24) | * atl (autolysin) | *Staphylococcus aureus* |
| Tat | MTDKKSENQTEKTETKENKGM TRREMLKLSAVAGTGIAVGATG LGTILNVVDQVDKALT (SEQ ID NO: 25) | lmo0367 | *Listeria monocytogenes* |
| | MAYDSRFDEWVQKLKEESFQN NTFDRRKFIQGAGKIAGLGLGLT IAQSVGAFG (SEQ ID NO: 26) | PhoD (alkaline phosphatase) | *Bacillus subtillis* |

The polypeptides as described herein, e.g., antigens or antigen-complementary affinity molecule fusion protein can be expressed and purified by a variety methods known to one skilled in the art, for example, the fusion polypeptides described herein can be purified from any suitable expression system. Fusion polypeptides can be purified to substantial purity by standard techniques, including selective precipitation with such substances as ammonium sulfate; column chromatography, immunopurification methods, and others; which are well-known in the art. See, e.g., Scopes, PROTEIN PURIFICATION: PRINCIPLES & PRACTICE (1982); U.S. Pat. No. 4,673,641.

A number of procedures can be employed when recombinant proteins are purified. For example, proteins having established molecular adhesion properties can be reversibly fused to the protein of choice. With the appropriate ligand, the protein can be selectively adsorbed to a purification column and then freed from the column in a relatively pure form. The fused protein is then removed by enzymatic activity. Finally, the protein of choice can be purified using affinity or immunoaffinity columns.

After the protein is expressed in the host cells, the host cells can be lysed to liberate the expressed protein for purification. Methods of lysing the various host cells are featured in "Sample Preparation-Tools for Protein Research" EMD Bioscience and in the Current Protocols in Protein Sciences (CPPS). An example purification method is affinity chromatography such as metal-ion affinity chromatograph using nickel, cobalt, or zinc affinity resins for histidine-tagged fusion polypeptides. Methods of purifying histidine-tagged recombinant proteins are described by Clontech using their TALON® cobalt resin and by NOVAGEN® in their pET system manual, 10th edition. Another preferred purification strategy is immuno-affinity chromatography, for example, anti-myc antibody conjugated resin can be used to affinity purify myc-tagged fusion polypeptides. When appropriate protease recognition sequences are present, fusion polypeptides can be cleaved from the histidine or myc tag, releasing the fusion polypeptide from the affinity resin while the histidine-tags and myc-tags are left attached to the affinity resin.

Standard protein separation techniques for purifying recombinant and naturally occurring proteins are well known in the art, e.g., solubility fractionation, size exclusion gel filtration, and various column chromatography.

Solubility Fractionation

Often as an initial step, particularly if the protein mixture is complex, an initial salt fractionation can separate many of the unwanted host cell proteins (or proteins derived from the cell culture media) from the protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Exclusion Filtration

The molecular weight of the protein of choice can be used to isolate it from proteins of greater and lesser size using ultrafiltration through membranes of different pore size (for example, AMICON® or MILLIPORE® membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The protein of choice can also be separated from other proteins on the basis of its size, net surface charge, hydrophobicity, and affinity for ligands. In addition, antibodies raised against recombinant or naturally occurring proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech). For example, an antigen polypeptide can be purified using a PA63 heptamer affinity column. Singh et al., 269, J. Biol. Chem. 29039 (1994).

In some embodiments, a combination of purification steps comprising, for example: (a) ion exchange chromatography, (b) hydroxyapatite chromatography, (c) hydrophobic interaction chromatography, and (d) size exclusion chromatography can be used to purify the fusion polypeptides described herein.

Cell-free expression systems are also contemplated. Cell-free expression systems offer several advantages over traditional cell-based expression methods, including the easy modification of reaction conditions to favor protein folding, decreased sensitivity to product toxicity and suitability for high-throughput strategies such as rapid expression screening or large amount protein production because of reduced reaction volumes and process time. The cell-free expression system can use plasmid or linear DNA. Moreover, improvements in translation efficiency have resulted in yields that exceed a milligram of protein per milliliter of reaction mix. Commercially available cell-free expression systems include the TNT coupled reticulocyte lysate Systems (Promega) which uses rabbit reticulocyte-based in vitro system.

Formulations of an Immune Composition and Methods of Use

Specific embodiments of the present invention provide for use of the immunogenic compositions as disclosed herein to elicit an immune response in an animal. More specifically, the compositions elicit both humoral and cellular immunity, and in many instance mucosal immunity. Embodiments of the present invention provide at least partial protection from or partial improvement after infection by, in particular, pneumococcus. Pneumococci cause a number of diseases, such as meningitis, pneumonia, bacteremia, and otitis media. Almost one million children die of pneumococcal diseases worldwide every year. *S. pneumoniae* have been studied extensively, and at least some of the genomes sequenced. See, e.g., U.S. Pat. No. 7,141,418. Although antibodies to the capsular polysaccharides, which define the known serotypes, confer serotype-specific protection, other protective mechanisms of immunity have been described. See Malley et al., 88 J. Mol. Med. 135 (2010). These other protective mechanisms include, but are not limited to, antibodies to noncapsular antigens and T cell responses to pneumococcal constituents. The application of protein-polysaccharide conjugate vaccine, PCV7, has reduced diseases significantly. Black et al., 24(S2) Vaccine 79 (2006); Hansen et al., 25 Pediatr. Infect. Dis. J. 779 (2006)). Yet, recent studies have shown that the lack of other serotypes in PCV7 has resulted in emerging replacement pneumococcal serotypes. Pichichero & Casey, 26(S10) Pediatr. Infect. Dis. J. S12 (2007).

Certain pneumococcal antigens common to all serotypes of the species have been shown to have immunoprotective potential despite the encapsulation, e.g., the surface proteins PspA, PspC, PsaA and the cytotoxin pneumolysin or pneumolysoid mutants (Basset et al., 75 Infect. Immun. 5460 (2007); Briles et al., 18 Vaccine 1707 (2000)); the use of genomics and mutational libraries has identified several dozen additional species-common proteins (Hava & Camilli, 45 Mol. Microbiol. 1389 (2002); Wizemann et al., 60 Infect. Immun. 1593 (2001)). Immunity has been induced by individual antigens in animal models (Alexander et al., 62 Infect. Immun. 5683 (1994); Balachandran et al., 70 Infect. Immun. 2526 (2002); Chung et al., 170 J. Immunol. 1958 (2003); Glover et al., 76 Infect. Immun. 2767 (2008); Wu et al., 175 J. Infect. Dis. 839 (1997)), but no vaccine based on a common antigen has been approved for human use to date.

In one embodiment, provided herein is a method of vaccinating a mammal comprising administering the immunogenic composition comprising at least one, or multiple antigens attached to at least one type of polymer scaffold, e.g., a polysaccharide or carbohydrate polymer for use in eliciting an immune response to the one or more antigens attached to the polymer when administered to a subject. In some embodiments, the immune response is a humoral and/or cellular immune response.

Accordingly, one aspect of the present invention relates to methods to elicit an immune response in a subject, comprising administering to the subject an immunogenic composition comprising at least one type of the polymer, e.g., a polysaccharide, at least one antigen, and at least one complementary affinity-molecule pair comprising (i) a first affinity molecule which associates with the polymer, e.g., a polysaccharide, and (ii) a complementary affinity molecule which associates with the antigen, to attach the antigen to the polymer, e.g., a polysaccharide, (e.g., the first affinity molecule associates with the complementary affinity molecule to link the antigen to the polymer, e.g., polysaccharide).

Accordingly, one aspect of the present invention relates to methods to elicit a humoral and/or cellular immunity to multiple antigens at the same time, e.g., where the immunogenic composition administered to the subject comprises a polymer comprising at least 1, or at least 2, or a more, e.g., a plurality of the same or different antigens.

One aspect of the present invention relates to a method of immunization or vaccinating a subject, e.g., a bird or a mammal, e.g., a human against a pathogen comprises administering an immune composition as disclosed herein comprising at least one antigen derived from one or more pathogens. In some embodiments, a subject can be immunized against at least 1, or at least 2, or at least 2, or at least 3, or at least 5, or at least 10, or at least 15, or at least about 20, or at least 50, or at least about 100, or more than 100 different pathogens at the same time, where the polymer of the immunogenic composition as the corresponding different antigens attached.

In some embodiments, a subject can be administered several different immunogenic compositions as disclosed herein, for example, a subject can be administered a composition comprising a polymer with an antigen, or a plurality of antigens, e.g., antigens A, B, C, and D etc., and also administered a composition comprising a polymer comprising a different antigen, or a different set of antigens, e.g., antigens W, X, Y, and Z etc. Alternatively, a subject can be administered a composition comprising a polymer A with an antigen, or a plurality of antigens, e.g., antigens A, B, C, and D, etc., and also administered a composition comprising a polymer B comprising the same e.g., antigens A, B, C, and D etc., or a different set of antigens. It is envisioned that the present invention provides a methods for the immunization of a subject with as many antigens as desired, e.g., with a variety of different immunogenic complexes as described herein, to enable immunization with as many as 100 or more antigens.

In one embodiment, the immunogenic compositions as described herein comprise a pharmaceutically acceptable carrier. In another embodiment, the immunogenic composition composition described herein is formulated for administering to a bird, mammal, or human, as or in a vaccine. Suitable formulations can be found in, for example, Remington's Pharmaceutical Sciences (2006), or Introduction to Pharmaceutical Dosage Forms (4th ed., Lea & Febiger, Philadelphia, 1985).

In one embodiment, the immunogenic compositions as described herein comprise pharmaceutically acceptable carriers that are inherently nontoxic and nontherapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. For all administrations, conventional depot forms are suitably used. Such forms include, for example, microcapsules, nano-capsules, liposomes, plasters, inhalation forms, nose sprays, sublingual tablets, and sustained release preparations. For examples of sustained release compositions, see U.S. Pat. Nos. 3,773,919, 3,887,699, EP 58,481A, EP 158, 277A, Canadian Patent No. 1176565; Sidman et al., 22 Biopolymers 547 (1983); Langer et al., 12 Chem. Tech. 98 (1982). The proteins will usually be formulated at a concentration of about 0.1 mg/ml to 100 mg/ml per application per patient.

In one embodiment, other ingredients can be added to vaccine formulations, including antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

In some embodiments, the present MAPS immunogen compositions are administered with at least one adjuvant. Adjuvants are a heterogeneous group of substances that enhance the immunological response against an antigen that is administered simultaneously. In some instances, adjuvants improve the immune response so that less vaccine is needed. Adjuvants serve to bring the antigen—the substance that stimulates the specific protective immune response—into contact with the immune system and influence the type of immunity produced, as well as the quality of the immune response (magnitude or duration). Adjuvants can also decrease the toxicity of certain antigens; and provide solubility to some vaccine components. Almost all adjuvants used today for enhancement of the immune response against antigens are particles or form particles together with the antigen. In the book VACCINE DESIGN—SUBUNIT & ADJUVANT APPROACH (Powell & Newman, Eds., Plenum Press, 1995), many known adjuvants are described both regarding their immunological activity and regarding their chemical characteristics. The type of adjuvants that do not form particles are a group of substances that act as immunological signal substances and that under normal conditions consist of the substances that are formed by the immune system as a consequence of the immunological activation after administration of particulate adjuvant systems.

Adjuvants for immunogenic compositions and vaccines are well known in the art. Examples include, but not limited to, monoglycerides and fatty acids (e.g. a mixture of monoolein, oleic acid, and soybean oil); mineral salts, e.g., aluminium hydroxide and aluminium or calcium phosphate gels; oil emulsions and surfactant based formulations, e.g., MF59 (microfluidised detergent stabilised oil-in-water emulsion), QS21 (purified saponin), AS02 [SBAS2] (oil-in-water emulsion+MPL+QS-21), MPL-SE, Montanide ISA-51 and ISA-720 (stabilised water-in-oil emulsion); particulate adjuvants, e.g., virosomes (unilamellar liposomal vehicles incorporating influenza haemagglutinin), ASO4 ([SBAS4] Al salt with MPL), ISCOMS (structured complex of saponins and lipids), polylactide co-glycolide (PLG); microbial derivatives (natural and synthetic), e.g., monophosphoryl lipid A (MPL), Detox (MPL+M. Phlei cell wall skeleton), AGP [RC-529] (synthetic acylated monosaccharide), Detox-PC, DC_Chol (lipoidal immunostimulators able to self-organize into liposomes), OM-174 (lipid A derivative), CpG motifs (synthetic oligonucleotides containing immunostimulatory CpG motifs), or other DNA structures, modified LT and CT (genetically modified bacterial toxins to provide non-toxic adjuvant effects); endogenous human immunomodulators, e.g., hGM-CSF or hIL-12 (cytokines that can be administered either as protein or plasmid encoded), Immudaptin (C3d tandem array), MoGM-CSF, TiterMax-G, CRL-1005, GERBU, TERamide, PSC97B, Adjumer, PG-026, GSK-I, GcMAF, B-alethine, MPC-026, Adjuvax, CpG ODN, Betafectin, Alum, and MF59 and inert vehicles, such as gold particles. Additional adjuvants are known in the art, see, e.g., U.S. Pat. No. 6,890,540; U. S. Patent Pub. No. 2005; 0244420; PCT/SE97/01003.

In some embodiments an adjuvant is a particulate and can have a characteristic of being slowly biodegradable. Care must be taken to ensure that that the adjuvant do not form toxic metabolites. Preferably, in some embodiments, such adjuvants can be matrices used are mainly substances originating from a body. These include lactic acid polymers, poly-amino acids (proteins), carbohydrates, lipids and biocompatible polymers with low toxicity. Combinations of these groups of substances originating from a body or combinations of substances originating from a body and biocompatible polymers can also be used. Lipids are the preferred substances since they display structures that make them biodegradable as well as the fact that they are a critical element in all biological membranes.

In one embodiment, the immunogenic compositions as described herein for administration must be sterile for administration to a subject. Sterility is readily accomplished by filtration through sterile filtration membranes (e.g., 0.2 micron membranes), or by gamma irradiation.

In some embodiments, the immunogenic compositions described herein further comprise pharmaceutical excipients including, but not limited to biocompatible oils, physiological saline solutions, preservatives, carbohydrate, protein, amino acids, osmotic pressure controlling agents, carrier gases, pH-controlling agents, organic solvents, hydrophobic agents, enzyme inhibitors, water absorbing polymers, surfactants, absorption promoters and anti-oxidative agents. Representative examples of carbohydrates include soluble sugars such as hydropropyl cellulose, carboxymethyl cellulose, sodium carboxyl cellulose, hyaluronic acid, chitosan, alginate, glucose, xylose, galactose, fructose, maltose, saccharose, dextran, chondroitin sulfate, etc. Representative examples of proteins include albumin, gelatin, etc. Representative examples of amino acids include glycine, alanine, glutamic acid, arginine, lysine, and their salts. Such pharmaceutical excipients are well-known in the art.

In some embodiments, the immunogenic MAPS composition is administered in combination with other therapeutic ingredients including, e.g., γ-interferon, cytokines, chemotherapeutic agents, or anti-inflammatory, or anti-viral agents. In some embodiments, the immunogenic composition as disclosed herein can be administered with one or more co-stimulatory molecules and/or adjuvants as disclosed herein.

In some embodiments, the immunogenic composition is administered in a pure or substantially pure form, but may be administered as a pharmaceutical composition, formulation or preparation. Such formulation comprises MAPS described herein together with one or more pharmaceutically acceptable carriers and optionally other therapeutic ingredients. Other therapeutic ingredients include compounds that enhance antigen presentation, e.g., gamma interferon, cytokines, chemotherapeutic agents, or anti-inflammatory agents. The formulations can conveniently be presented in unit dosage form and may be prepared by methods well known in the pharmaceutical art. For example, Plotkin and Mortimer, in VACCINES (2nd ed., W.B. Saunders Co., 1994) describes vaccination of animals or humans to induce an immune response specific for particular pathogens, as well as methods of preparing antigen, determining a suitable dose of antigen, and assaying for induction of an immune response.

Formulations suitable for intravenous, intramuscular, intranasal, oral, sublingual, vaginal, rectal, subcutaneous, or intraperitoneal administration conveniently comprise sterile aqueous solutions of the active ingredient with solutions which are preferably isotonic with the blood of the recipient. Such formulations may be conveniently prepared by dissolving solid active ingredient in water containing physiologically compatible substances such as sodium chloride (e.g., 0.1M-2.0 M), glycine, and the like, and having a buffered pH compatible with physiological conditions to produce an aqueous solution, and rendering the solution sterile. These may be present in unit or multi-dose containers, for example, sealed ampoules or vials.

Liposomal suspensions can also be used as pharmaceutically acceptable carriers. These can be prepared according to methods known to those skilled in the art, for example, as described in U.S. Pat. No. 4,522,811.

Formulations for an intranasal delivery are described in U.S. Pat. Nos. 5,427,782; 5,843,451; 6,398,774.

The formulations of the immunogenic compositions can incorporate a stabilizer. Illustrative stabilizers are polyethylene glycol, proteins, saccharide, amino acids, inorganic acids, and organic acids which may be used either on their own or as admixtures. Two or more stabilizers may be used in aqueous solutions at the appropriate concentration and/or pH. The specific osmotic pressure in such aqueous solution is generally in the range of 0.1-3.0 osmoses, preferably in the range of 0.80-1.2. The pH of the aqueous solution is adjusted to be within the range of pH 5.0-9.0, preferably within the range of pH 6-8.

When oral preparations are desired, the immunogenic compositions can be combined with typical carriers, such as lactose, sucrose, starch, talc magnesium stearate, crystalline cellulose, methyl cellulose, carboxymethyl cellulose, glycerin, sodium alginate or gum arabic among others.

In some embodiments, the immunogenic compositions as described herein can be administered intravenously, intranasally, intramuscularly, subcutaneously, intraperitoneally, sublingually, vaginal, rectal or orally. In some embodiments, the route of administration is oral, intranasal, subcutaneous, or intramuscular. In some embodiments, the route of administration is intranasal administration.

Vaccination can be conducted by conventional methods. For example, an immunogenic compositions can be used in a suitable diluent such as saline or water, or complete or incomplete adjuvants. The immunogenic composition can be administered by any route appropriate for eliciting an immune response. The immunogenic composition can be administered once or at periodic intervals until an immune response is elicited. Immune responses can be detected by a variety of methods known to those skilled in the art, including but not limited to, antibody production, cytotoxicity assay, proliferation assay and cytokine release assays. For example, samples of blood can be drawn from the immunized mammal, and analyzed for the presence of antibodies against the antigens of the immunogenic composition by ELISA (see de Boer et. al., 115 Arch Virol. 147 (1990) and the titer of these antibodies can be determined by methods known in the art.

The precise dose to be employed in the formulation will also depend on the route of administration and should be decided according to the judgment of the practitioner and each patient's circumstances. For example, a range of 25 µg-900 µg total protein can be administered monthly for three months.

Ultimately, the attending physician will decide the amount of immunogenic composition or vaccine composition to administer to particular individuals. As with all immunogenic compositions or vaccines, the immunologically effective amounts of the immunogens must be determined empirically. Factors to be considered include the immunogenicity, whether or not the immunogen will be complexed with or covalently attached to an adjuvant or carrier protein or other carrier, routes of administrations and the number of immunizing dosages to be administered. Such factors are known in the vaccine art and it is well within the skill of immunologists to make such determinations without undue experimentation.

Kits

The present invention also provides for kits for producing an immunogenic composition as disclosed herein which is useful for an investigator to tailor an immunogenic composition with their preferred antigens, e.g., for research purposes to assess the effect of an antigen, or a combination of antigens on immune response. Such kits can be prepared from readily available materials and reagents. For example, such kits can comprise any one or more of the following materials: a container comprising a polymer, e.g., a polysaccharide, cross-linked with a plurality of first affinity molecules; and a container comprising a complementary affinity molecule which associates with the first affinity molecule, wherein the complementary affinity molecule associates with an antigen.

In another embodiment, the kit can comprise a container comprising a polymer, e.g., a polysaccharide, a container comprising a plurality of first affinity molecules, and a container comprising a cross-linking reagent for cross-linking the first affinity molecules to the polymer.

In some embodiments, the kit further comprises a means to attach the complementary affinity molecule to the antigen, where the means can be by a cross-linking reagent or by some intermediary fusion protein. In some embodiments, the kit can comprise at least one co-stimulation factor which can be added to the polymer. In some embodiments, the kit comprises a cross-linking reagent, for example, but not limited to, CDAP (1-cyano-4-dimethylaminopyridinium tetrafluoroborate), EDC (1-Ethyl-3-[3-dimethylaminopropyl] carbodiimide hydrochloride), sodium cyanoborohydride; cyanogen bromide; ammonium bicarbonate/iodoacetic acid for linking the co-factor to the polymer.

A variety of kits and components can be prepared for use in the methods described herein, depending upon the intended use of the kit, the particular target antigen and the needs of the user.

In one embodiment, an immunogenic composition or vaccine composition as described herein, when administered to mice, can provoke an immune response that prevents a disease symptom in at least 20% of animals challenged with 5 $LD_{50}$ of the immunogenic composition comprising antigens to which the disease symptom is prevented. Methods of vaccination and challenging an immunized animal are known to one skilled in the art. For example, a 10 µg aliquot of an immunogenic composition or vaccine composition as disclosed herein can be prepared in 100 µl PBS and/or with addition of incomplete Freund's adjuvant and injected intramuscularly per mouse per vaccination. Alternatively, parenteral, intraperitoneal and footpad injections can be used. Volumes of footpad injections are reduced to 50 µl. Mice can be immunized with an immunogenic composition or vaccine composition as disclosed herein on three separate occasions with several days, e.g., 14 days interval in between.

Efficacy of vaccination can be tested by challenge with the pathogen. Seven days after the last dose of an immunogenic composition, the immunized mice are challenged intranasally with a pathogenic organism from which the antigen was derived. Ether anaesthetized mice (10 g to 12 g) can be infected intranasally with 50 µl of PBS-diluted allantoic fluid containing 5 $LD_{50}$ of the pathogenic organism. Protection can be measured by monitoring animal survival and body weight, which is assessed throughout an observation period of 21 days. Severely affected mice are euthanized. One $LD_{50}$ of A/Mallard/Pennsylvania/10218/84 is equal to 100-1000 the Tissue Culture Infectious Dose50 (TCID50) assay.

In other embodiments, the immunized mice can be challenged with a variety of different pathogenic organisms, e.g., different pathogenic organisms from which each of the antigens attached to the polymer are derived. For example, of an immunogenic composition comprises five different antigens attached to the polymer, e.g., polysaccharide, where each antigen is derived from five different pathogenic organisms, the immunized mice can be challenged with each of the five different pathogenic organisms, either sequentially (in any order) or concurrently. One skilled in the art would be able to determine the $LD_{50}$ for each pathogenic organism used to challenge the immunized mice by methods known in the art. See, e.g., LaBarre & Lowy, 96 J. Virol. Meths. 107 (2001); Golub, 59J. Immunol. 7 (1948).

Although the foregoing invention has been described in some detail by way of illustration and example for purposes of clarity of understanding it will be readily apparent to one of ordinary skill in the art in light of the teachings of this invention that certain changes and modifications may be made thereto without departing from the spirit or scope of the appended claims. The following is meant to be illustrative of the present invention; however, the practice of the invention is not limited or restricted in any way by the examples.

EXAMPLES

The examples presented herein relate to methods to generate an immunogenic complex as described herein and methods and compositions thereof. In particular, the examples relate to methods to produce a multiple antigen presentation (MAP) complex as disclosed herein, and methods of use to generate an immune response in a subject.

Example 1

Construction of Recombinant Rhizavidin and Rhizavidin-Antigen Fusion Proteins

The recombinant Rhizavidin (rRhavi) used in these studies is an N-terminal modified version that contains only the residues 45 to 179 of the wild type protein. To optimize the expression level of rRhavi in *E. coli*, the gene sequence that encodes Rhizavidin polypeptides (45-179) was re-designed by using *E. coli*-preferred expression codons, then synthesized and cloned into the PET21b vector. To facilitate the correct folding and obtain a high yield of soluble recombinant protein, a DNA sequence encoding an *E. coli* periplasmic localization signal sequence (19 amino acids, MKKIWLALAGLVLAFSASA, SEQ ID NO:1) was introduced at the 5' end of the synthetic gene of rRhavi. This signal sequence is predicted to be deleted automatically from the recombinant protein after its targeting to the periplasm of *E. coli* during the process of expression.

To construct a Rhizavidin-antigen fusion protein, a DNA sequence encoding a flexible linker region consisting of seven amino acids (GGGGSSS, SEQ ID NO:27) was directly inserted into the 3' end of the synthetic rRhavi gene, to help stablize the fusion protein. The genes encoding candidate antigens (full length or desired fragment) were amplified from the genomic DNA of interested pathogens by routine PCR procedures and inserted into the rRhavi expression vector just beyond the linker region.

For protein expression, the plasmids containing target constructs were transformed into *E. coli* strain BL21 (DE3) using standard heat-shock procedure. A single colony was picked freshly from the plate (or a glycerol stock was used later) and inoculated into 30 ml Luria-Bertani (LB) medium containing Ampicillin (Amp+) for an overnight culture at 37° C. On day 2, a 5 ml starting culture was inoculated into 1 liter of LB medium/Amp+ and grown at 37° C. until $OD_{600}$=1 was reached. After cooling the medium to 16° C., 0.2 mM final concentration of IPTG was added into the cultures for an overnight induction.

Proteins were purified from the periplasmic fraction using a modified osmotic shock protocol. Briefly, the bacterial cells from the 6 liter culture were collected and resuspended in 120 ml buffer containing 30 mM Tris (pH 8.0), 20% sucrose and 1 mM EDTA. After stiffing at room temperature for 20 mM, the cells were re-pelleted by centrifugation at 10,000 rpm for 10 mM. The supernatant was collected as fraction 1, and the cells were resuspended in 80 ml ice cold solution containing 5 mM $MgCl_2$, proteinase inhibitor and DNase. After stiffing at 4° C. for 20 mM, the mixture was subjected to centrifugation at 13,000 rpm for 20 mM and the supernatant was collected as fraction 2. After adding a final concentration of 150 mM NaCl, 10 mM $MgCl_2$ and 10 mM Imidazole, the supernatant combining fraction 1 and fraction 2 was applied onto a Ni-NTA column. The proteins eluted from the Ni-NTA column were further purified by gel-filtration using superdex 200 column running on AKTA purifier. The peak fractions containing target protein were pooled and concentrated. The protein concentration was measured by using BCA protein assay kit from Bio-Rad. Purified proteins were aliquoted, flash-frozen in liquid nitrogen and kept at −80° C. for future use.

Example 2

Biotinylation of Polysaccharide

The biotinylation of polysaccharides was done by using 1-cyano-4-dimethylaminopyridinium tetrafluoroborate (CDAP) as the activation reagent. Briefly, the polysaccharides were dissolved in LPS-free water at 10 mg/ml (or other concentration as indicated). At t=0, a volume of CDAP (freshly made at 100 mg/ml in acetonitrile) was slowly added to the polysaccharide solution at a ratio of 1-2 mg CDAP/mg polysaccharide, while vortexing. Thirty seconds later, a volume of 0.2 M triethylamine (TEA) was added (equal or double to the volume of CDAP, depending on the different types of polysaccharide) to raise the pH. At 2.5 mM, a volume of biotin derivative (EZ-Link Amine-PEG3-Biotin from Pierce, solubilized at 20 mg/ml in LPS-free water) was added to a final ratio of 1-1.5 mg biotin/mg polysaccharide for an overnight coupling at 4° C. (or 1-3 hr coupling at 25° C.). On day 2, 50 mM final concentration of glycine or serine was added to terminate the reaction and then the mixture was desalted by passage over a column or dialyzed against a large volume of PBS to remove free biotin derivatives. The biotin content in the biotinylated polysaccharide was measured by using the biotin quantification kit from Pierce and the polysaccharide concentration was determined by the anthrone assay.

Example 3

Assembly and Purification of MAPS

To assemble a MAPS complex, a volume of biotinylated polysaccharide was mixed with the candidate rRhavi-antigen fusion proteins in a desired ratio and then incubated at 4° C. or 25° C. overnight. After incubation, the mixture was centrifuged at 13,200 rpm for 3 min to remove the insoluble aggregates. The supernatant was applied to the gel-filtration chromatography, using superpose-6 or sperdex-200 column, with PBS, Tris buffer, or saline as the running solution. The peak fractions containing large molecular weight complex were collected and concentrated. The protein contents and the ratio of different antigens in MAPS complex was tested by SDS-PAGE with Coomassie blue staining, and the protein/polysaccharide ratio of MAPS was determined by using BCA protein assay kit and the anthrone assay.

Example 4

Immunization; Antibody and Cytokine Analysis; Challenge in Mice

All immunogenic compositions and vaccines were prepared the day before immunization. Pneumococcal whole cell vaccine, MAPS or an equimolar mixture containing all the specific antigens, rhizavidin, polysaccharide and biotin were diluted using saline to indicated concentration, and then mixed with $Al(OH)_3$ in a 15 ml conical tube for adsorption overnight at 4° C.

C57BL/6J mice (Jackson Laboratories, Bar Harbor, Me.) were used in all immunization experiments. The age at time of first immunization was between 4-6 weeks. Gently restrained, non-anesthetized mice received 3 subcutaneous injections of 200 µl of adjuvant with or without indicated amount of antigen in the lower part of the back at 2-week intervals. Blood was drawn 2 weeks after the second and/or the third immunization, and assayed for antibody and for cytokine production in vitro after stimulation with pneumococcal whole cell antigen (WCA), TB extract, or particular protein antigen.

Challenge was performed 2 weeks after the last immunization or bleeding. In NP colonization model, mice were intranasally challenged with $2 \times 10^7$ colony-forming units (CFU) of serotype 6B strain 0603 in 20 µl of PBS. To determine the presence and degree of NP colonization, an upper respiratory culture was done 10 days later by instilling sterile saline retrograde through the transected trachea, collecting the first 6 drops (about 0.1 ml) from the nostrils, and plating neat or diluted samples on blood agar plates containing 2.5 µg gentamicin/ml.

In aspiration-sepsis challenge model, mice were gently anesthetized with isoflorane, held supine, and given a 100 µg intranasal inoculation containing $10^6$ CFU of pneumococci serotype 3 strain WU-2. Mice were monitored twice daily and sacrificed by $CO_2$ inhalation and terminal exsanguination when demonstrating signs of illness, following which a blood culture was obtained.

Assays for murine antibodies to WCA or different protein antigens were done in Immulon 2 HB 96-microwell plates (Thermo Scientific, Waltham, Mass.) coated with WCA (100 µg protein/ml PBS) or with protein antigens (1 µg of protein/ml PBS). Plates were blocked with 1% BSA in PBS. Antibody diluted in PBS-T was added and incubated at room temperature for 2 hr. Plates were washed with PBS-T, and secondary HRP-conjugated antibody to mouse immunoglobulin G (from Sigma) was added and incubated at room temperature for one hour. The plates were washed and developed with SureBlue TMB Microwell Peroxidase Substrate (KPL, Gaithersburg, Md.).

For cytokine stimulation, the stimulants were diluted in stimulation medium (DMEM (BioWhittaker, Walkersville, Md.) containing 10% low-endotoxin defined FBS (Hyclone, Logan, Utah), 50 µM 2-mercaptoethanol (Sigma) and ciprofloxacin (10 µg/ml, Cellgro, Manassas, Va.)), at a concentration of 1 µg/ml-10 µg/ml for all protein antigens, or for pneumococcal WCA. 25 µl of heparinized blood was added to 225 µl DMEM medium with/without stimulants and cultured at 37° C. for 6 days. Supernatants were collected following centrifugation and stored at −80° C. until analyzed by ELISA for IL-17A or IFN-γ concentration (R&D Systems, Minneapolis, Minn.).

For stimulation of splenocytes, mouse splenocytes were isolated, resuspended in stimulation medium, and then seeded in 48-well plate ($3 \times 10^6$ cells/well, in 300 µl of volume). After incubation at 37° C. for 2 hr, stimuli were added at indicated concentration, for stimulation at 37° C. for 3 days. Supernatants were collected following centrifugation and stored at −80° C. until analyzed by ELISA for IL-17A or IFN-γ concentration Antibody and IL-17A concentrations and NP colonization densities were compared by the Mann-Whitney U test using PRISM (version 4.0a for Macintosh, GraphPad Software, Inc). Differences in survival were analyzed with the Kaplan-Meier test, using PRISM as well.

We claim:

1. An immunogenic composition comprising an immunologically effective amount of at least one antigenic polysaccharide, an immunologically effective amount of one to ten different peptide or polypeptide antigens, and one to ten different pairs of affinity molecules, wherein each pair comprises a first affinity molecule and a second affinity molecule complementary to the first affinity molecule, wherein in each pair:

the first affinity molecule is associated with the at least one antigenic polysaccharide, and the complementary second affinity molecule is covalently attached to one of the peptide or polypeptide antigens to form a fusion protein, and the first affinity molecule non-covalently associates with the complementary second affinity molecule to link the respective peptide or polypeptide antigen and the at least one antigenic polysaccharide; and wherein the immunogenic composition, upon administration to a subject, elicits (i) an immune response to the at least one antigenic polysaccharide, and (ii) an immune response to at least one of the one to ten different peptide or polypeptide antigens, in the subject.

2. The immunogenic composition of claim 1, wherein the first affinity molecule is cross-linked or covalently bonded to the antigenic polysaccharide.

3. The immunogenic composition of claim 2, wherein the first affinity molecule is cross-linked to the antigenic polysaccharide using a cross-linking reagent selected from any in the group consisting of: CDAP (1-cyano-4-dimethylaminopyridinium tetrafluoroborate); EDC (1-Ethyl-3-[3-dimethylaminopropyl] carbodiimide hydrochloride); sodium cyanoborohydride; cyanogen bromide; and ammonium bicarbonate/iodoacetic acid.

4. The immunogenic composition of claim 1, wherein the pair(s) of the affinity molecules is/are each independently selected from the group consisting of: biotin/biotin-binding protein, antibody/antigen, enzyme/substrate, receptor/ligand, metal/metal-binding protein, carbohydrate/carbohydrate binding protein, lipid/lipid-binding protein, and His tag/His tag-binding substance.

5. The immunogenic composition of claim 1, wherein the first affinity molecule is biotin or a derivative or mimic molecule thereof.

6. The immunogenic composition of claim 1, wherein the complementary second affinity molecule is a biotin-binding protein, or an avidin-like protein or a derivative or functional portion thereof.

7. The immunogenic composition of claim 6, wherein the avidin-like protein is selected from the group consisting of: rhizavidin, avidin, streptavidin, and a homologue or derivative thereof.

8. The immunogenic composition of claim 1, wherein the antigenic polysaccharide is a branched chain polysaccharide or a straight chain polysaccharide.

9. The immunogenic composition of claim 1, comprising two to ten different peptide or polypeptide antigens, wherein the peptide or polypeptide antigens are selected from the group consisting of: different peptides or polypeptides; different variants of the same peptide or polypeptide; and different domains or portions of the same peptide or polypeptide.

10. The immunogenic composition of claim 1, further comprising a flexible linker peptide attached to the peptide or polypeptide antigens, wherein the flexible linker peptide attaches the peptide or polypeptide antigens to the complementary second affinity molecule.

11. The immunogenic composition of claim 1, wherein at least one of the peptide or polypeptide antigen is from a pathogenic organism, or a cancer or tumor.

12. The immunogenic composition of claim 1, wherein at least one of the peptide or polypeptide antigens is selected from the group consisting of: tuberculosis antigens; *Staphylococcus aureus* antigens; *Acinetobacter* antigens; enteric Gram-negative bacterial antigens; nonenteric Gram-negative bacterial antigens; Gram-positive bacterial antigens; toxoids, toxins or toxin portions; fungal antigens; viral antigens; cancer or tumor antigens; and combinations thereof.

13. The immunogenic composition of claim 1, wherein the antigenic polysaccharide is selected from the group consisting of: polysaccharides, oligosaccharides, or lipopolysaccharides from Gram-positive bacteria; polysaccharides, oligosaccharides, or lipopolysaccharides from Gram-negative bacteria; other bacterial capsular or cell wall polysaccharides; fungal polysaccharides; viral polysaccharides; and polysaccharides derived from cancer or tumor cells.

14. The immunogenic composition of claim 1, further comprising at least one co-stimulation factor associated with the antigenic polysaccharide or at least one of the peptide or polypeptide antigens.

15. The immunogenic composition of claim 14, wherein the co-stimulation factor is selected from the group consisting of: a Toll-like receptor ligand/agonist, a NOD ligand/agonist, and an activator/agonist of an inflammasome.

16. The immunogenic composition of claim 1, further comprising at least one adjuvant.

17. A method for inducing an immune response in a subject to at least one antigen, comprising administering to the subject a composition of claim 1.

18. The method of claim 17, wherein the immune response is an antibody or B cell response.

19. The method of claim 17, wherein the immune response is a CD4+ T cell response, including Th1, Th2, or Th17 response, or a CD8+ T cell response, or CD4+/CD8+ T cell response.

20. The method of claim 17, wherein the immune response is:
an antibody or B cell response; and
a T cell response.

21. The method of claim 17, wherein the immune response is to at least one antigenic polysaccharide or at least one peptide or polypeptide antigen.

22. The method of claim 17, wherein the immune response is an antibody or B cell response to at least one antigenic polysaccharide and a CD4+ T cell response, including Th 1, Th2, or Th 17 response, or a CD8+ T cell response, or CD4+/CD8+ T cell response to at least one peptide or polypeptide antigen.

23. The method of claim 17, wherein the immune response is an antibody or B cell response to at least one antigenic polysaccharide, and an antibody or B cell response and a CD4+ T cell response, including Th1, Th2, or Th 17 response, or a CD8+ T cell response, or CD4+/CD8+ T cell response to at least one peptide or polypeptide antigen.

24. The immunogenic composition of claim 12, wherein the enteric Gram-negative bacterial antigens are selected from the group of: E. coli antigens, *Salmonella* antigens, *Enterobacter* antigens, *Klebsiella* antigens, *Citrobacter* antigens, *Serratia* antigens, *Clostridia* antigens, *Shigella* antigens, *Campylobacter* antigens, *Vibrio cholera* antigens, and combinations thereof.

25. The immunogenic composition of claim 12, wherein the nonenteric Gram-negative bacterial antigens are selected from the group of: *Pertussis* antigens, Meningococcal antigens, *Haemophilus* antigens, *Pseudomonas* antigens, and combinations thereof.

26. The immunogenic composition of claim 12, wherein the Gram-positive bacterial antigens are pneumococcal antigens or anthrax antigens.

27. The immunogenic composition of claim 12, wherein the viral antigens are HIV antigens, or seasonal or epidemic influenza antigens.

28. The immunogenic composition of claim 13, wherein the antigenic polysaccharide is selected from the group consisting of: *Salmonella typhi* Vi capsular polysaccharides; *Salmonella* polysaccharides; pneumococcal polysaccharides; *Haemophili* polysaccharides; Meningococcal polysaccharides; *Staphylococcus aureus* polysaccharides; *Bacillus anthracis* polysaccharides; *Streptococcus* polysaccharides; *Pseudomonas* polysaccharides; *Cryptococcus* polysaccharides; and viral glycoproteins.

29. The immunogenic composition of claim 28, wherein the antigenic polysaccharide is selected from the group consisting of: *Salmonella typhi* Vi capsular polysaccharides; pneumococcal capsular polysaccharides; pneumococcal cell wall polysaccharides; *Staphylococcus aureus* capsular polysaccharides; *Haemophilus influenzae* Type b (Hib) polysaccharides; Gp A *Streptococcus* polysaccharides; and Gp B *Streptococcus* polysaccharides.

30. The immunogenic composition of claim 1, comprising five to ten different peptide or polypeptide antigens, wherein the peptide or polypeptide antigens are selected from the group consisting of: different peptides or polypeptides; different variants of the same peptide or polypeptide; and different domains or portions of the same peptide or polypeptide.

31. The immunogenic composition of claim 1, comprising two to ten different peptide or polypeptide antigens, wherein at least two different peptide or polypeptide antigens are linked to the same antigenic polysaccharide.

32. The immunogenic composition of claim 1, comprising at least two different antigenic polysaccharides and two to ten different peptide or polypeptide antigens, wherein at least two different peptide or polypeptide antigens are each linked to a different antigenic polysaccharide.

33. The immunogenic composition of claim 1, wherein the complementary second affinity molecule is covalently attached to a fusion protein comprising two or more peptide or polypeptide antigens.

34. An immunogenic composition comprising:
- an immunologically effective amount of at least one antigenic polysaccharide, and
- an immunologically effective amount of one to ten different peptide or polypeptide antigens,
- wherein the at least one antigenic polysaccharide is cross-linked or covalently bonded to biotin, and the one to ten peptide or polypeptide antigens are associated with at least one rhizavidin peptide, derivative, or functional portion thereof, and
- wherein the one to ten peptide or polypeptide antigens and the at least one antigenic polysaccharide are linked by a non-covalent, affinity interaction between the biotin and the rhizavidin peptide, derivative, or functional portion thereof; and
- wherein the immunogenic composition, upon administration to a subject, elicits (i) an immune response to the at least one antigenic polysaccharide, and (ii) an immune response to at least one of the one to ten different peptide or polypeptide antigens, in the subject.

35. The immunogenic composition of claim 1, wherein the immune response to the at least one antigenic polysaccharide and/or to at least one of the one to ten different peptide or polypeptide antigens comprises an antibody or B cell response.

36. The immunogenic composition of claim 1, wherein the immune response to the at least one antigenic polysaccharide and/or to at least one of the one to ten different peptide or polypeptide antigens comprises a T cell response.

37. The immunogenic composition of claim 1, wherein the immune response to the at least one antigenic polysaccharide and/or to at least one of the one to ten different peptide or polypeptide antigens comprises a CD4+ T cell response, including Th1, Th2, or Th17 response, or a CD8+ T cell response, or a CD4+/CD8+ T cell response.

38. The immunogenic composition of claim 1, wherein the immune response to the at least one antigenic polysaccharide and/or to at least one of the one to ten different peptide or polypeptide antigens comprises:
- an antibody or B cell response; and
- a T cell response.

39. The immunogenic composition of claim 1, wherein the immunogenic composition, upon administration to a subject, elicits at least (i) an antibody or B cell response to the at least one antigenic polysaccharide, and (ii) an antibody or B cell response to at least one of the one to ten different peptide or polypeptide antigens, in the subject.

40. The immunogenic composition of claim 1, wherein the immunogenic composition, upon administration to a subject, elicits at least (i) an antibody or B cell response to the at least one antigenic polysaccharide, and (ii) an antibody or B cell response and a CD4+ T cell response, including Th1, Th2, or Th17 response, or a CD8+ T cell response, or a CD4+/CD8+ T cell response to at least one of the one to ten different peptide or polypeptide antigen, in the subject.

41. The immunogenic composition of claim 1, wherein the immunogenic composition, upon administration to a subject, elicits at least (i) an antibody or B cell response to the at least one antigenic polysaccharide, and (ii) a CD4+ T cell response, including Th1, Th2, or Th17 response, or a CD8+ T cell response, or a CD4+/CD8+ T cell response to at least one of the one to ten different peptide or polypeptide antigens, in the subject.

42. The method of claim 17, further comprising administering to the subject a therapeutic agent.

* * * * *

SEQUENCE LISTING

```
<160> NUMBER OF SEQ ID NOS: 31

<210> SEQ ID NO 1
<211> LENGTH: 19
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 1

Met Lys Lys Ile Trp Leu Ala Leu Ala Gly Leu Val Leu Ala Phe Ser
1               5                   10                  15

Ala Ser Ala

<210> SEQ ID NO 2
<211> LENGTH: 20
<212> TYPE: PRT
<213> ORGANISM: Chlamyidia trachomatis

<400> SEQUENCE: 2

Asn Val Thr Gln Asp Leu Thr Ser Ser Thr Ala Lys Leu Glu Cys Thr
1               5                   10                  15

Gln Asp Leu Ile
            20

<210> SEQ ID NO 3
<211> LENGTH: 20
<212> TYPE: PRT
<213> ORGANISM: Chlamyidia trachomatis

<400> SEQUENCE: 3

Ala Lys Leu Glu Cys Thr Gln Asp Leu Ile Ala Gln Gly Lys Leu Ile
1               5                   10                  15

Val Thr Asn Pro
            20

<210> SEQ ID NO 4
<211> LENGTH: 9
<212> TYPE: PRT
<213> ORGANISM: Chlamyidia trachomatis

<400> SEQUENCE: 4

Ser Asn Leu Lys Arg Met Gln Lys Ile
1               5

<210> SEQ ID NO 5
<211> LENGTH: 9
<212> TYPE: PRT
<213> ORGANISM: Chlamyidia trachomatis

<400> SEQUENCE: 5

Ala Ala Leu Tyr Ser Thr Glu Asp Leu
1               5

<210> SEQ ID NO 6
<211> LENGTH: 9
<212> TYPE: PRT
<213> ORGANISM: Chlamyidia trachomatis

<400> SEQUENCE: 6

Phe Gln Glu Lys Asp Ala Asp Thr Leu
1               5

<210> SEQ ID NO 7
<211> LENGTH: 9
<212> TYPE: PRT
<213> ORGANISM: Chlamyidia trachomatis

<400> SEQUENCE: 7
```

```
Gln Ser Val Asn Glu Leu Val Tyr Val
1               5

<210> SEQ ID NO 8
<211> LENGTH: 9
<212> TYPE: PRT
<213> ORGANISM: Chlamyidia trachomatis

<400> SEQUENCE: 8

Leu Glu Phe Ala Ser Cys Ser Ser Leu
1               5

<210> SEQ ID NO 9
<211> LENGTH: 9
<212> TYPE: PRT
<213> ORGANISM: Chlamyidia trachomatis

<400> SEQUENCE: 9

Ser Gln Ala Glu Gly Gln Tyr Arg Leu
1               5

<210> SEQ ID NO 10
<211> LENGTH: 9
<212> TYPE: PRT
<213> ORGANISM: Chlamyidia trachomatis

<400> SEQUENCE: 10

Gly Gln Ser Val Asn Glu Leu Val Tyr
1               5

<210> SEQ ID NO 11
<211> LENGTH: 9
<212> TYPE: PRT
<213> ORGANISM: Chlamyidia trachomatis

<400> SEQUENCE: 11

Gln Ala Val Leu Leu Leu Asp Gln Ile
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Arg or Leu
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (6)..(6)
<223> OTHER INFORMATION: Tyr or Trp

<400> SEQUENCE: 12

Asp Xaa Ala Xaa Pro Xaa
1               5

<210> SEQ ID NO 13
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Arg or Leu
<220> FEATURE:
<221> NAME/KEY: MOD_RES
<222> LOCATION: (5)..(5)
<223> OTHER INFORMATION: Ser or Thr
<220> FEATURE:
<221> NAME/KEY: MOD_RES
<222> LOCATION: (7)..(7)
<223> OTHER INFORMATION: Tyr or Trp

<400> SEQUENCE: 13

Cys Asp Xaa Ala Xaa Pro Xaa Cys Gly
1               5

<210> SEQ ID NO 14
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Met Ala Pro Phe Glu Pro Leu Ala Ser Gly Ile Leu Leu Leu Leu Trp
1               5                   10                  15

Leu Ile Ala Pro Ser Arg Ala
            20

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Ser Pro Gly Ile Ser Gly Gly Gly Gly Gly Ile Leu Glu
1               5                   10

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 16

Leu Pro Xaa Thr Gly
1               5

<210> SEQ ID NO 17
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17
```

```
Pro Glu Pro
1

<210> SEQ ID NO 18
<211> LENGTH: 24
<212> TYPE: PRT
<213> ORGANISM: Listeria monocytogenes

<400> SEQUENCE: 18

Met Lys Lys Ile Met Leu Val Ile Thr Leu Ile Leu Val Ser Pro Ile
1               5                   10                  15

Ala Gln Gln Thr Glu Ala Lys Asp
            20

<210> SEQ ID NO 19
<211> LENGTH: 29
<212> TYPE: PRT
<213> ORGANISM: Lactococcus lactis

<400> SEQUENCE: 19

Met Lys Lys Lys Ile Ile Ser Ala Ile Leu Met Ser Thr Val Ile Leu
1               5                   10                  15

Ser Ala Ala Ala Pro Leu Ser Gly Val Tyr Ala Asp Thr
            20                  25

<210> SEQ ID NO 20
<211> LENGTH: 31
<212> TYPE: PRT
<213> ORGANISM: Bacillus anthracis

<400> SEQUENCE: 20

Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala Glu Val
            20                  25                  30

<210> SEQ ID NO 21
<211> LENGTH: 29
<212> TYPE: PRT
<213> ORGANISM: Listeria monocytogenes

<400> SEQUENCE: 21

Met Asn Met Lys Lys Ala Thr Ile Ala Ala Thr Ala Gly Ile Ala Val
1               5                   10                  15

Thr Ala Phe Ala Ala Pro Thr Ile Ala Ser Ala Ser Thr
            20                  25

<210> SEQ ID NO 22
<211> LENGTH: 54
<212> TYPE: PRT
<213> ORGANISM: Listeria monocytogenes

<400> SEQUENCE: 22

Met Gln Lys Thr Arg Lys Glu Arg Ile Leu Glu Ala Leu Gln Glu Glu
1               5                   10                  15

Lys Lys Asn Lys Lys Ser Lys Lys Phe Lys Thr Gly Ala Thr Ile Ala
            20                  25                  30

Gly Val Thr Ala Ile Ala Thr Ser Ile Thr Val Pro Gly Ile Glu Val
        35                  40                  45

Ile Val Ser Ala Asp Glu
    50
```

```
<210> SEQ ID NO 23
<211> LENGTH: 28
<212> TYPE: PRT
<213> ORGANISM: Bacillus anthracis

<400> SEQUENCE: 23

Met Lys Lys Leu Lys Met Ala Ser Cys Ala Leu Val Ala Gly Leu Met
1               5                   10                  15

Phe Ser Gly Leu Thr Pro Asn Ala Phe Ala Glu Asp
            20                  25

<210> SEQ ID NO 24
<211> LENGTH: 31
<212> TYPE: PRT
<213> ORGANISM: Staphylococcus aureus

<400> SEQUENCE: 24

Met Ala Lys Lys Phe Asn Tyr Lys Leu Pro Ser Met Val Ala Leu Thr
1               5                   10                  15

Leu Val Gly Ser Ala Val Thr Ala His Gln Val Gln Ala Ala Glu
            20                  25                  30

<210> SEQ ID NO 25
<211> LENGTH: 59
<212> TYPE: PRT
<213> ORGANISM: Listeria monocytogenes

<400> SEQUENCE: 25

Met Thr Asp Lys Lys Ser Glu Asn Gln Thr Glu Lys Thr Glu Thr Lys
1               5                   10                  15

Glu Asn Lys Gly Met Thr Arg Arg Glu Met Leu Lys Leu Ser Ala Val
            20                  25                  30

Ala Gly Thr Gly Ile Ala Val Gly Ala Thr Gly Leu Gly Thr Ile Leu
        35                  40                  45

Asn Val Val Asp Gln Val Asp Lys Ala Leu Thr
    50                  55

<210> SEQ ID NO 26
<211> LENGTH: 53
<212> TYPE: PRT
<213> ORGANISM: Bacillus subtillis

<400> SEQUENCE: 26

Met Ala Tyr Asp Ser Arg Phe Asp Glu Trp Val Gln Lys Leu Lys Glu
1               5                   10                  15

Glu Ser Phe Gln Asn Asn Thr Phe Asp Arg Arg Lys Phe Ile Gln Gly
            20                  25                  30

Ala Gly Lys Ile Ala Gly Leu Gly Leu Gly Leu Thr Ile Ala Gln Ser
        35                  40                  45

Val Gly Ala Phe Gly
    50

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27
```

```
Gly Gly Gly Gly Ser Ser Ser
1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 28

His His His His His His
1               5

<210> SEQ ID NO 29
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Met Lys Lys Ile Trp Leu Ala Leu Ala Gly Leu Val Leu Ala Phe Ser
1               5                   10                  15

Ala Ser Ala Ala Gln Asp Pro
            20

<210> SEQ ID NO 30
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Gly Gly Gly Ser Ser Ser Val Asp Lys Leu Ala Ala Ala Leu Glu
1               5                   10                  15

His His His His His His
            20

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Leu Glu His His His His His His
1               5
```